US010443049B2

(12) United States Patent
Batlle et al.

(10) Patent No.: US 10,443,049 B2
(45) Date of Patent: Oct. 15, 2019

(54) ACTIVE LOW MOLECULAR WEIGHT VARIANTS OF ANGIOTENSIN CONVERTING ENZYME 2 (ACE2)

(71) Applicant: Northwestern University, Evanston, IL (US)

(72) Inventors: Daniel Batlle, Chicago, IL (US); Jan Wysocki, Chicago, IL (US)

(73) Assignee: Northwestern University, Evanston, IL (US)

( * ) Notice: Subject to any disclaimer, the term of this patent is extended or adjusted under 35 U.S.C. 154(b) by 71 days.

(21) Appl. No.: 15/878,823

(22) Filed: Jan. 24, 2018

(65) Prior Publication Data

US 2018/0230447 A1    Aug. 16, 2018

Related U.S. Application Data

(60) Provisional application No. 62/449,857, filed on Jan. 24, 2017.

(51) Int. Cl.

| | |
|---|---|
| *C12N 9/48* | (2006.01) |
| *A61K 47/68* | (2017.01) |
| *C07K 14/765* | (2006.01) |
| *A61K 47/60* | (2017.01) |
| *A61K 38/48* | (2006.01) |
| *A61K 47/69* | (2017.01) |
| *C07K 14/315* | (2006.01) |

(52) U.S. Cl.
CPC .......... *C12N 9/485* (2013.01); *A61K 38/4813* (2013.01); *A61K 47/60* (2017.08); *A61K 47/68* (2017.08); *A61K 47/6929* (2017.08); *C07K 14/315* (2013.01); *C07K 14/765* (2013.01); *C12Y 304/17023* (2013.01); *C07K 2319/21* (2013.01); *C07K 2319/30* (2013.01); *C07K 2319/31* (2013.01); *C07K 2319/70* (2013.01)

(58) Field of Classification Search
None
See application file for complete search history.

(56) References Cited

U.S. PATENT DOCUMENTS 6,884,771 B1    4/2005 Acton et al.

FOREIGN PATENT DOCUMENTS

WO    2011039096 A1    4/2011

OTHER PUBLICATIONS

Xiao et al. (Characterization of Angiotensin-Converting Enzyme 2 Ectodomain Shedding from Mouse Proximal Tubular Cells, PloS one, vol. 9, Issue 1, Jan. 2014) (Year: 2014).*

Haas M, Moolenaar F, Meijer DK and de Zeeuw D. Specific drug delivery to the kidney. Cardiovascular drugs and therapy. 2002;16:489-96.
Haber PK, Ye M, Wysocki J, Maier C, Haque SK and Batlle D. Angiotensin-converting enzyme 2-independent action of presumed angiotensin-converting enzyme 2 activators: studies in vivo, ex vivo, and in vitro. Hypertension. 2014;63:774-82.
Harlan SM, Heinz-Taheny KM, Sullivan JM, Wei T, Baker He, Jaqua DL, Qi Z, Cramer MS, Shiyanova TL, Breyer MD and Heuer JG. Progressive Renal Disease Established by Renin-Coding Adeno-Associated Virus-Driven Hypertension in Diverse Diabetic Models. J Am Soc Nephrol. 2017.
Haschke M, Schuster M, Poglitsch M, Loibner H, Salzberg M, Bruggisser M, Penninger J and Krahenbuhl S. Pharmacokinetics and pharmacodynamics of recombinant human angiotensin-converting enzyme 2 in healthy human subjects. Clinical pharmacokinetics. 2013;52:783-92.
Haymann JP, Levraud JP, Bouet S, Kappes V, Hagege J, Nguyen G, Xu Y, Rondeau E and Sraer JD. Characterization and localization of the neonatal Fc receptor in adult human kidney. J Am Soc Nephrol. 2000;11:632-9.
Hudkins KL, Pichaiwong W, Wietecha T, Kowalewska J, Banas MC, Spencer MW, Muhlfeld A, Koelling M, Pippin JW, Shankland SJ, Askari B, Rabaglia ME, Keller MP, Attie AD and Alpers CE. BTBR Ob/Ob mutant mice model progressive diabetic nephropathy. J Am Soc Nephrol. 2010;21:1533-42.
Ingelfinger JR, Zuo WM, Fon EA, Ellison KE and Dzau VJ. In situ hybridization evidence for angiotensinogen messenger RNA in the rat proximal tubule. An hypothesis for the intrarenal renin angiotensin system. The Journal of clinical investigation. 1990;85:417-23.
Ingert C, Grima M, Michel B, Barthelmebs M and Imbs JL. [Renal tissue angiotensins during converting enzyme inhibition of angiotensin I in spontaneously hypertensive rat]. Archives des maladies du coeur et des vaisseaux. 1997;90:1135-41.
Jevsevar S, Kunstelj M and Porekar VG. PEGylation of therapeutic proteins. Biotechnology journal. 2010;5:113-28.
Jiang F, Yang J, Zhang Y, Dong M, Wang S, Zhang Q, Liu FF, Zhang K and Zhang C. Angiotensin-converting enzyme 2 and angiotensin 1-7: novel therapeutic targets. Nature reviews Cardiology. 2014;11:413-26.

(Continued)

*Primary Examiner* — Suzanne M Noakes
*Assistant Examiner* — Jae W Lee
(74) *Attorney, Agent, or Firm* — Quarles & Brady LLP; M. Scott McBride

(57) ABSTRACT

Disclosed are variants of ACE2, pharmaceutical compositions comprising the variants of ACE2, and treatment methods for reducing Angiotensin II (1-8) plasma levels and/or increasing Angiotensin (1-7) plasma levels in a subject in need thereof. The disclosed variants of ACE2 may include polypeptide fragments of ACE2 having ACE2 activity for converting AngII(1-8) to Ang(1-7). Suitable subjects suitable for the disclosed methods of treatment may include subjects having or at risk for developing diabetic and non-diabetic chronic kidney disease, acute renal failure and its prevention, chronic kidney disease, severe hypertension, scleroderma and its skin, pulmonary, kidney and hypertensive complications, malignant hypertension, renovascular hypertension secondary to renal artery stenosis, idiopathic pulmonary fibrosis, liver fibrosis such as in liver cirrhosis patients, an aortic aneurysm, cardiac fibrosis and remodeling, left ventricular hypertrophy, and an acute stroke.

18 Claims, 10 Drawing Sheets

Specification includes a Sequence Listing.

(56) References Cited

OTHER PUBLICATIONS

Kamiyama M, Zsombok A and Kobori H. Urinary angiotensinogen as a novel early biomarker of intrarenal renin-angiotensin system activation in experimental type 1 diabetes. Journal of pharmacological sciences. 2012;119:314-23.
Kanwar YS and Farquhar MG. Anionic sites in the glomerular basement membrane. In vivo and in vitro localization to the laminae rarae by cationic probes. The Journal of cell biology. 1979;81:137-53.
Kanwar YS and Farquhar MG. Presence of heparan sulfate in the glomerular basement membrane. Proceedings of the National Academy of Sciences of the United States of America. 1979;76:1303-7.
Kobori H, Harrison-Bernard LM and Navar LG. Urinary excretion of angiotensinogen reflects intrarenal angiotensinogen production. Kidney international. 2002;61:579-585.
Kok RJ, Grijpstra F, Walthuis RB, Moolenaar F, de Zeeuw D and Meijer DK. Specific delivery of captopril to the kidney with the prodrug captopril-lysozyme. The Journal of pharmacology and experimental therapeutics. 1999;288:281-5.
Komine N, Khang S, Wead LM, Blantz RC and Gabbai FB. Effect of combining an ACE inhibitor and an angiotensin II receptor blocker on plasma and kidney tissue angiotensin II levels. American journal of kidney diseases : the official journal of the National Kidney Foundation. 2002;39:159-64.
Kontermann RE. Strategies for extended serum half-life of protein therapeutics. Current opinion in biotechnology. 2011;22:868-76.
Levy OE, Jodka CM, Ren SS, Mamedova L, Sharma A, Samant M, D'Souza LJ, Soares CJ, Yuskin DR, Jin LJ, Parkes DG, Tatarkiewicz K and Ghosh SS. Novel exenatide analogs with peptidic albumin binding domains: potent anti-diabetic agents with extended duration of action. PloS one. 2014;9:e87704.
Lewis EJ, Hunsicker LG, Clarke WR, Berl T, Pohl MA, Lewis JB, Ritz E, Atkins RC, Rohde R and Raz I. Renoprotective effect of the angiotensin-receptor antagonist irbesartan in patients with nephropathy due to type 2 diabetes. The New England journal of medicine. 2001;345:851-60.
Lewis EJ, Hunsicker LG, Bain RP and Rohde RD. The effect of angiotensin-converting-enzyme inhibition on diabetic nephropathy. The Collaborative Study Group. The New England journal of medicine. 1993;329:1456-62.
Li M, Liu K, Michalicek J, Angus JA, Hunt JE, Dell'Italia LJ, Feneley MP, Graham RM and Husain A. Involvement of chymase-mediated angiotensin II generation in blood pressure regulation. The Journal of clinical investigation. 2004;114:112-20.
Liu P, Wysocki J, Serfozo P, Ye M, Souma T, D B and J. J. A Fluorometric Method of Measuring Carboxypeptidase Activities for Angiotensin II and Apelin 13. Scientific Reports. 2017.
Lo C-S, Chang S-Y, Chenier I, Filep JG, Ingelfinger JR, Zhang SL and Chan JSD. Heterogeneous Nuclear Ribonucleoprotein F Suppresses Angiotensinogen Gene Expression and Attenuates Hypertension and Kidney Injury in Diabetic Mice. Diabetes. 2012;61:2597-2608.
Lorenz JN. Chymase: the other ACE? Am J Physiol Renal Physiol. 2010;298:F35-6.
Macdougall IC, Gray SJ, Elston O, Breen C, Jenkins B, Browne J and Egrie J. Pharmacokinetics of novel erythropoiesis stimulating protein compared with epoetin alfa in dialysis patients. J Am Soc Nephrol. 1999;10:2392-5.
Maier C, Schadock I, Haber PK, Wysocki J, Ye M, Kanwar Y, Flask CA, Yu X, Hoit BD, Adams GN, Schmaier AH, Bader M and Batlle D. Prolylcarboxypeptidase deficiency is associated with increased blood pressure, glomerular lesions, and cardiac dysfunction independent of altered circulating and cardiac angiotensin II. Journal of molecular medicine (Berlin, Germany). 2017.
Mezzano SA, Ruiz-Ortega M and Egido J. Angiotensin II and Renal Fibrosis. Hypertension. 2001;38:635-638.

Mills KT, Kobori H, Hamm LL, Alper AB, Khan IE, Rahman M, Navar LG, Liu Y, Browne GM, Batuman V, He J and Chen J. Increased urinary excretion of angiotensinogen is associated with risk of chronic kidney disease. Nephrology Dialysis Transplantation. 2012;27:3176-3181.
Moestrup SK and Verroust PJ. Megalin- and cubilin-mediated endocytosis of protein-bound vitamins, lipids, and hormones in polarized epithelia. Annual review of nutrition. 2001;21:407-28.
Mori J, Patel VB, Ramprasath T, Alrob OA, DesAulniers J, Scholey JW, Lopaschuk GD and Oudit GY. Angiotensin 1-7 mediates renoprotection against diabetic nephropathy by reducing oxidative stress, inflammation, and lipotoxicity. Am J Physiol Renal Physiol. 2014;306:F812-21.
Nadarajah R, Milagres R, Dilauro M, Gutsol A, Xiao F, Zimpelmann J, Kennedy C, Wysocki J, Batlle D and Burns KD. Podocyte-specific overexpression of human angiotensin-converting enzyme 2 attenuates diabetic nephropathy in mice. Kidney Int. 2012;82:292-303.
Nagasu H, Satoh M, Kiyokage E, Kidokoro K, Toida K, Channon KM, Kanwar YS, Sasaki T and Kashihara N. Activation of endothelial NAD(P)H oxidase accelerates early glomerular injury in diabetic mice. Lab Invest. 2016;96:25-36.
Nakagawa T, Sato W, Glushakova O, Heinig M, Clarke T, Campbell-Thompson M, Yuzawa Y, Atkinson MA, Johnson RJ and Croker B. Diabetic endothelial nitric oxide synthase knockout mice develop advanced diabetic nephropathy. Journal of the American Society of Nephrology : JASN. 2007;18:539-50.
Nilvebrant J and Hober S. The albumin-binding domain as a scaffold for protein engineering. Computational and structural biotechnology journal. 2013;6:e201303009.
Nguyen MT, Han J, Ralph DL, Veiras LC and McDonough AA. Short-term nonpressor angiotensin II infusion stimulates sodium transporters in proximal tubule and distal nephron. Physiological reports. 2015;3.
Okada H. A Look at Transactivation of the EGF Receptor by Angiotensin II. J Am Soc Nephrol. 2012;23:183-5.
Oudit GY, Herzenberg AM, Kassiri Z, Wong D, Reich H, Khokha R, Crackower MA, Backx PH, Penninger JM and Scholey JW. Loss of angiotensin-converting enzyme-2 leads to the late development of angiotensin II-dependent glomerulosclerosis. The American journal of pathology. 2006;168:1808-20.
Palazzo V, Provenzano A, Becherucci F, Sansavini G, Mazzinghi B, Orlandini V, Giunti L, Roperto RM, Pantaleo M, Artuso R, Andreucci E, Bargiacchi S, Traficante G, Stagi S, Murer L, Benetti E, Emma F, Giordano M, Rivieri F, Colussi G, Penco S, Manfredini E, Caruso MR, Garavelli L, Andrulli S, Vergine G, Miglietti N, Mancini E, Malaventura C, Percesepe A, Grosso E, Materassi M, Romagnani P and Giglio S. The genetic and clinical spectrum of a large cohort of patients with distal renal tubular acidosis. Kidney international. 2017.
Park CH and Maack T. Albumin absorption and catabolism by isolated perfused proximal convoluted tubules of the rabbit. The Journal of clinical investigation. 1984;73:767-77.
Park S, Bivona BJ, Kobori H, Seth DM, Chappell MC, Lazartigues E and Harrison-Bernard LM. Major role for ACE-independent intrarenal ANG II formation in type II diabetes. Am J Physiol Renal Physiol. 2010;298:F37-48.
Peti-Peterdi J, Kang JJ and Toma I. Activation of the renal renin-angiotensin system in diabetes—new concepts. Nephrology Dialysis Transplantation. 2008;23:3047-3049.
Price DA, Porter LE, Gordon M, Fisher ND, De'Oliveira JM, Laffel LM, Passan DR, Williams GH and Hollenberg NK. The paradox of the low-renin state in diabetic nephropathy. J Am Soc Nephrol. 1999;10:2382-91.
Quaggin SE and Coffman TM. Toward a mouse model of diabetic nephropathy: is endothelial nitric oxide synthase the missing link? Journal of the American Society of Nephrology : JASN. 2007;18:364-6.
Raij L. The pathophysiologic basis for blocking the renin-angiotensin system in hypertensive patients with renal disease. Am J Hypertens. 2005;18:95s-99s.

(56) References Cited

OTHER PUBLICATIONS

Rennke HG, Cotran RS and Venkatachalam MA. Role of molecular charge in glomerular permeability. Tracer studies with cationized ferritins. The Journal of cell biology. 1975;67:638-46.
Roig E, Perez-Villa F, Morales M, Jimenez W, Orus J, Heras M and Sanz G. Clinical implications of increased plasma angiotensin II despite ACE inhibitor therapy in patients with congestive heart failure. European heart journal. 2000;21:53-7.
Rosenberg ME, Smith LJ, Correa-Rotter R and Hostetter TH. The paradox of the renin-angiotensin system in chronic renal disease. Kidney Int. 1994;45:403-10.
Ross MJ and Nangaku M. ACE2 as therapy for glomerular disease: the devil is in the detail. Kidney International. 2017;91:1269-1271.
Russo LM, Sandoval RM, McKee M, Osicka TM, Collins AB, Brown D, Molitoris BA and Comper WD. The normal kidney filters nephrotic levels of albumin retrieved by proximal tubule cells: retrieval is disrupted in nephrotic states. Kidney Int. 2007;71:504-13.
Saito A, Sato H, Iino N and Takeda T. Molecular mechanisms of receptor-mediated endocytosis in the renal proximal tubular epithelium. Journal of biomedicine & biotechnology. 2010;2010:403272.
Salem ES, Grobe N and Elased KM. Insulin treatment attenuates renal ADAM17 and ACE2 shedding in diabetic Akita mice. Am J Physiol Renal Physiol. 2014;306:F629-39.
Sand KMK, Dalhus B, Christianson GJ, Bern M, Foss S, Cameron J, Sleep D, Bjørås M, Roopenian DC, Sandlie I and Andersen JT. Dissection of the Neonatal Fc Receptor (FcRn)-Albumin Interface Using Mutagenesis and Anti-FcRn Albumin-blocking Antibodies. The Journal of biological chemistry. 2014;289:17228-17239.
Sandoval RM, Wagner MC, Patel M, Campos-Bilderback SB, Rhodes GJ, Wang E, Wean SE, Clendenon SS and Molitoris BA. Multiple factors influence glomerular albumin permeability in rats. J Am Soc Nephrol. 2012;23:447-57.
Santos RA, Ferreira AJ, Verano-Braga T and Bader M. Angiotensin-converting enzyme 2, angiotensin-(1-7) and Mas: new players of the renin-angiotensin system. The Journal of endocrinology. 2013;216:R1-r17.
Sarav M, Wang Y, Hack BK, Chang A, Jensen M, Bao L and Quigg RJ. Renal FcRn reclaims albumin but facilitates elimination of IgG. J Am Soc Nephrol. 2009;20:1941-52.
Schellenberger V, Wang CW, Geething NC, Spink BJ, Campbell A, To W, Scholle MD, Yin Y, Yao Y, Bogin O, Cleland JL, Silverman J and Stemmer WP. A recombinant polypeptide extends the in vivo half-life of peptides and proteins in a tunable manner. Nat Biotechnol. 2009;27:1186-90.
Schelling JR, Hanson AS, Marzec R and Linas SL. Cytoskeleton-dependent endocytosis is required for apical type 1 angiotensin II receptor-mediated phospholipase C activation in cultured rat proximal tubule cells. J Clin Invest. 1992;90:2472-80.
Schulte S. Half-life extension through albumin fusion technologies. Thrombosis research. 2009;124 Suppl 2:S6-8.
Shariat-Madar Z, Mahdi F and Schmaier AH. Identification and characterization of prolylcarboxypeptidase as an endothelial cell prekallikrein activator. J Biol Chem. 2002;277:17962-9.
Sharman DC, Morris AD and Struthers AD. Gradual reactivation of vascular angiotensin I to angiotensin II conversion during chronic ACE inhibitor therapy in patients with diabetes mellitus. Diabetologia. 2007;50:2061-6.
Shiigai T and Shichiri M. Late escape from the antiproteinuric effect of ace inhibitors in nondiabetic renal disease. American journal of kidney diseases : the official journal of the National Kidney Foundation. 2001;37:477-83.
Simões e Silva AC and Teixeira MM. ACE inhibition, ACE2 and angiotensin-(1?7) axis in kidney and cardiac inflammation and fibrosis. Pharmacological Research. 2016;107:154-162.
Simoes e Silva AC, Silveira KD, Ferreira AJ and Teixeira MM. ACE2, angiotensin-(1-7) and Mas receptor axis in inflammation and fibrosis. British journal of pharmacology. 2013;169:477-92.
Soler MJ, Wysocki J, Ye M, Lloveras J, Kanwar Y and Batlle D. ACE2 inhibition worsens glomerular injury in association with increased ACE expression in streptozotocin-induced diabetic mice. Kidney Int. 2007;72:614-23.
Spiekermann et al., Receptor-mediated immunoglobulin G transport across mucosal barriers in adult life: functional expression of FcRn in the mammalian lung. J. Exp. Med. Aug. 5, 2002;196(3)-10.
Strohl WR. Fusion Proteins for Half-Life Extension of Biologics as a Strategy to Make Biobetters. BioDrugs : clinical immunotherapeutics, biopharmaceuticals and gene therapy. 2015;29:215-39.
Sung SH, Ziyadeh FN, Wang A, Pyagay PE, Kanwar YS and Chen S. Blockade of vascular endothelial growth factor signaling ameliorates diabetic albuminuria in mice. J Am Soc Nephrol. 2006;17:3093-104.
Sun L, Xiao L, Nie J, Liu F, Ling G, Zhu X, Tang W, Chen W, Xia Y, Zhan M, Ma M, Peng Y, Liu H, Liu Y and Kanwar YS. p66Shc mediates high-glucose and angiotensin II-induced oxidative stress renal tubular injury via mitochondrial-dependent apoptotic pathway. Am J Physiol Renal Physiol. 2010;299:F1014-25.
Suzuki T, Ishii-Watabe A, Tada M, Kobayashi T, Kanayasu-Toyoda T, Kawanishi T and Yamaguchi T. Importance of neonatal FcR in regulating the serum half-life of therapeutic proteins containing the Fc domain of human IgG1: a comparative study of the affinity of monoclonal antibodies and Fc-fusion proteins to human neonatal FcR. Journal of immunology (Baltimore, Md : 1950). 2010;184:1968-76.
Suzuki Y, Ruiz-Ortega M, Lorenzo O, Ruperez M, Esteban V and Egido J. Inflammation and angiotensin II. The International Journal of Biochemistry & Cell Biology. 2003;35:881-900.
Tom B, Garrelds IM, Scalbert E, Stegmann AP, Boomsma F, Saxena PR and Danser AH. ACE-versus chymase-dependent angiotensin II generation in human coronary arteries: a matter of efficiency? Arteriosclerosis, thrombosis, and vascular biology. 2003;23:251-6.
Towler P, Staker B, Prasad SG, Menon S, Tang J, Parsons T, Ryan D, Fisher M, Williams D, Dales NA, Patane MA and Pantoliano MW. ACE2 X-ray structures reveal a large hinge-bending motion important for inhibitor binding and catalysis. J Biol Chem. 2004;279:17996-8007.
Urata H, Boehm KD, Philip A, Kinoshita A, Gabrovsek J, Bumpus FM and Husain A. Cellular localization and regional distribution of an angiotensin II-forming chymase in the heart. The Journal of clinical investigation. 1993;91:1269-81.
Urata H, Healy B, Stewart RW, Bumpus FM and Husain A. Angiotensin II-forming pathways in normal and failing human hearts. Circ Res. 1990;66:883-90.
Urata H, Kinoshita A, Misono KS, Bumpus FM and Husain A. Identification of a highly specific chymase as the major angiotensin II-forming enzyme in the human heart. J Biol Chem. 1990;265:22348-57.
Van den Meiracker AH, Man in 't Veld AJ, Admiraal PJ, Ritsema van Eck HJ, Boomsma F, Derkx FH and Schalekamp MA. Partial escape of angiotensin converting enzyme (ACE) inhibition during prolonged ACE inhibitor treatment: does it exist and does it affect the antihypertensive response? Journal of hypertension. 1992;10:803-12.
Van de Wal RM, Plokker HW, Lok DJ, Boomsma F, van der Horst FA, van Veldhuisen DJ, van Gilst WH and Voors AA. Determinants of increased angiotensin II levels in severe chronic heart failure patients despite ACE inhibition. International journal of cardiology. 2006;106:367-72.
Velez JC. Prolyl carboxypeptidase: a forgotten kidney angiotensinase. Focus on "Identification of prolyl carboxypeptidase as an alternative enzyme for processing of renal angiotensin II using mass spectrometry". American journal of physiology Cell physiology. 2013;304:C939-40.
Vickers C, Hales P, Kaushik V, Dick L, Gavin J, Tang J, Godbout K, Parsons T, Baronas E, Hsieh F, Acton S, Patane M, Nichols A and Tummino P. Hydrolysis of biological peptides by human angiotensin-converting enzyme-related carboxypeptidase. J Biol Chem. 2002;277:14838-43.
Wei CC, Hase N, Inoue Y, Bradley EW, Yahiro E, Li M, Naqvi N, Powell PC, Shi K, Takahashi Y, Saku K, Urata H, Dell'italia LJ and Husain A. Mast cell chymase limits the cardiac efficacy of Ang I-converting enzyme inhibitor therapy in rodents. The Journal of clinical investigation. 2010;120:1229-39.

(56) References Cited

OTHER PUBLICATIONS

Welches WR, Santos RA, Chappell MC, Brosnihan KB, Greene LJ and Ferrario CM. Evidence that prolyl endopeptidase participates in the processing of brain angiotensin. Journal of hypertension. 1991;9:631-8.

Wysocki J, Garcia-Halpin L, Ye M, Maier C, Sowers K, Burns KD and Batlle D. Regulation of urinary ACE2 in diabetic mice. Am J Physiol Renal Physiol. 2013;305:F600-11.

Wysocki J, Goodling A, Burgaya M, Whitlock K, Ruzinski J, Batlle D and Afkarian M. Urine RAS components in mice and people with type 1 diabetes and chronic kidney disease. Am J Physiol Renal Physiol. 2017:ajprenal 00074 2017.

Wysocki J RJ, Afkarian M, Batlle D . . . Urinary prorenin is increased in patients with type 1 diabetes and nephropathy. ASN. 2016;Kidney Week.

Wysocki J, Ye M and Batlle D. Plasma and Kidney Angiotensin Peptides: Importance of the Aminopeptidase A/Angiotensin III Axis. Am J Hypertens. 2015;28:1418-26.

Wysocki J, Ye M, Khattab AM, Fogo A, Martin A, David NV, Kanwar Y, Osborn M and Batlle D. Angiotensin-converting enzyme 2 amplification limited to the circulation does not protect mice from development of diabetic nephropathy. Kidney Int. 2017;91:1336-1346.

Wysocki J, Ye M, Rodriguez E, Gonzalez-Pacheco FR, Barrios C, Evora K, Schuster M, Loibner H, Brosnihan KB, Ferrario CM, Penninger JM and Batlle D. Targeting the degradation of angiotensin II with recombinant angiotensin-converting enzyme 2: prevention of angiotensin II-dependent hypertension. Hypertension. 2010;55:90-8.

Wysocki J, Ye M, Soler MJ, Gurley SB, Xiao HD, Bernstein KE, Coffman TM, Chen S and Batlle D. ACE and ACE2 activity in diabetic mice. Diabetes. 2006;55:2132-9.

Yamada K, Iyer SN, Chappell MC, Ganten D and Ferrario CM. Converting enzyme determines plasma clearance of angiotensin-(1-7). Hypertension. 1998;32:496-502.

Ye M WJ, Khattab A, Issa H, Gutterman M, Molitch M, Batlle D . . . Urinary Angiotensinogen (AOG) is Increased in Type I Diabetes with Microalbuminuria. 2016.

Ye M, Wysocki J, Gonzalez-Pacheco FR, Salem M, Evora K, Garcia-Halpin L, Poglitsch M, Schuster M and Batlle D. Murine recombinant angiotensin-converting enzyme 2: effect on angiotensin II-dependent hypertension and distinctive angiotensin-converting enzyme 2 inhibitor characteristics on rodent and human angiotensin-converting enzyme 2. Hypertension. 2012;60:730-40.

Ye M, Wysocki J, Naaz P, Salabat MR, LaPointe MS and Batlle D. Increased ACE 2 and decreased ACE protein in renal tubules from diabetic mice: a renoprotective combination? Hypertension. 2004;43:1120-5.

Ye M, Wysocki J, William J, Soler MJ, Cokic I and Batlle D. Glomerular localization and expression of Angiotensin-converting enzyme 2 and Angiotensin-converting enzyme: implications for albuminuria in diabetes. J Am Soc Nephrol. 2006;17:3067-75.

Ying T, Chen W, Feng Y, Wang Y, Gong R and Dimitrov DS. Engineered soluble monomeric IgG1 CH3 domain: generation, mechanisms of function, and implications for design of biological therapeutics. J Biol Chem. 2013;288:25154-64.

Zatz R, Dunn BR, Meyer TW, Anderson S, Rennke HG and Brenner BM. Prevention of diabetic glomerulopathy by pharmacological amelioration of glomerular capillary hypertension. The Journal of clinical investigation. 1986;77:1925-30.

Zhang MZ, Wang S, Yang S, Yang H, Fan X, Takahashi T and Harris RC. Role of blood pressure and the renin-angiotensin system in development of diabetic nephropathy (DN) in eNOS−/− db/db mice. Am J Physiol Renal Physiol. 2012;302:F433-8.

Zhao HJ, Wang S, Cheng H, Zhang MZ, Takahashi T, Fogo AB, Breyer MD and Harris RC. Endothelial nitric oxide synthase deficiency produces accelerated nephropathy in diabetic mice. J Am Soc Nephrol. 2006;17:2664-9.

Zhou P, Sun X and Zhang Z. Kidney-targeted drug delivery systems. Acta Pharmaceutica Sinica B. 2014;4:37-42.

Afkarian M, Hirsch IB, Tuttle KR, Greenbaum C, Himmelfarb J and de Boer IH. Urinary excretion of RAS, BMP, and WNT pathway components in diabetic kidney disease. Physiological reports. 2014;2:e12010.

Akilesh S, Huber TB, Wu H, Wang G, Hartleben B, Kopp JB, Miner JH, Roopenian DC, Unanue ER and Shaw AS. Podocytes use FcRn to clear IgG from the glomerular basement membrane. Proceedings of the National Academy of Sciences of the United States of America. 2008;105:967-72.

Andersen JT, Dalhus B, Cameron J, Daba MB, Plumridge A, Evans L, Brennan SO, Gunnarsen KS, Bjoras M, Sleep D and Sandlie I. Structure-based mutagenesis reveals the albumin-binding site of the neonatal Fc receptor. Nature communications. 2012;3:610.

Anderson S, Jung FF and Ingelfinger JR. Renal renin-angiotensin system in diabetes: functional, immunohistochemical, and molecular biological correlations. Am J Physiol. 1993;265:F477-86.

Anderson S, Rennke HG and Brenner BM. Therapeutic advantage of converting enzyme inhibitors in arresting progressive renal disease associated with systemic hypertension in the rat. Journal of Clinical Investigation. 1986;77:1993-2000.

Athyros VG, Mikhailidis DP, Kakafika AI, Tziomalos K and Karagiannis A. Angiotensin II reactivation and aldosterone escape phenomena in renin-angiotensin-aldosterone system blockade: is oral renin inhibition the solution? Expert opinion on pharmacotherapy. 2007;8:529-35.

Baggish AL and Boucher CA. Radiopharmaceutical agents for myocardial perfusion imaging. Circulation. 2008;118:1668-74.

Bae EH, Fang F, Williams VR, Konvalinka A, Zhou X, Patel VB, Song X, John R, Oudit GY, Pei Y and Scholey JW. Murine recombinant angiotensin-converting enzyme 2 attenuates kidney injury in experimental Alport syndrome. Kidney Int. 2017.

Batlle D, Soler MJ, and Wysocki, New aspects of the renin-angiotensin system: angiontensin-converting enzyme 2—a potential target for treatment of hypertension and diabetic nephropathy, Curr. Opin Nephrol. Hypertens. May 2008; 17 (3):250-7.

Batlle D, Wysocki J, Soler MJ and Ranganath K. Angiotensin-converting enzyme 2: enhancing the degradation of angiotensin II as a potential therapy for diabetic nephropathy. Kidney Int. 2012;81:520-8.

Becker BN, Cheng H-f, Hammond TG and Harris RC. The Type 1 Angiotensin II Receptor Tail Affects Receptor Targeting, Internalization, and Membrane Fusion Properties. Molecular Pharmacology. 2004;65:362.

Benigni A, Cassis P and Remuzzi G. Angiotensin II revisited: new roles in inflammation, immunology and aging. EMBO Molecular Medicine. 2010;2:247-57.

Berry C. Clinical implications of increased plasma angiotensin II concentrations despite ACE inhibitor therapy in patients with congestive heart failure: the issue of non-compliance with therapy. European heart journal. 2000;21:1484-5.

Biollaz J, Schelling JL, Jacot Des Combes B, Brunner DB, Desponds G, Brunner HR, Ulm EH, Hichens M and Gomez HJ. Enalapril maleate and a lysine analogue (MK-521) in normal volunteers; relationship between plasma drug levels and the renin angiotensin system. British journal of clinical pharmacology. 1982;14:363-8.

Bitonti et al., Pulmonary delivery of an erythropoietin Fc fusion protein in non-human primates through an immunoglobulin transport pathway. Proc. Natl. Acad. Sci. USA Jun. 29, 2004; 101(26):9763-8.

Border WA and Noble NA. Interactions of Transforming Growth Factor-β and Angiotensin II in Renal Fibrosis. Hypertension. 1998;31:181-188.

Brasen JC, Burford JL, McDonough AA, Holstein-Rathlou NH and Peti-Peterdi J. Local pH domains regulate NHE3-mediated Na(+) reabsorption in the renal proximal tubule. Am J Physiol Renal Physiol. 2014;307:F1249-62.

Brenner BM, Cooper ME, de Zeeuw D, Keane WF, Mitch WE, Parving HH, Remuzzi G, Snapinn SM, Zhang Z and Shahinfar S. Effects of losartan on renal and cardiovascular outcomes in patients with type 2 diabetes and nephropathy. The New England journal of medicine. 2001;345:861-9.

(56) References Cited

OTHER PUBLICATIONS

Brosius FC, 3rd, Alpers CE, Bottinger EP, Breyer MD, Coffman TM, Gurley SB, Harris RC, Kakoki M, Kretzler M, Leiter EH, Levi M, McIndoe RA, Sharma K, Smithies O, Susztak K, Takahashi N and Takahashi T. Mouse models of diabetic nephropathy. J Am Soc Nephrol. 2009;20:2503-12.
Caliceti P and Veronese FM. Pharmacokinetic and biodistribution properties of poly(ethylene glycol)-protein conjugates. Advanced drug delivery reviews. 2003;55:1261-77.
Campbell DJ. The site of angiotensin production. Journal of hypertension. 1985;3:199-207.
Carney EF. Diabetic nephropathy: Renoprotective effects of angiotensin 1-7. Nature reviews Nephrology. 2014;10:240.
Chaudhury C, Brooks CL, Carter DC, Robinson JM and Anderson CL. Albumin binding to FcRn: distinct from the FcRn—IgG interaction. Biochemistry. 2006;45:4983-90.
Cheng HF, Becker BN, Burns KD and Harris RC. Angiotensin II upregulates type-1 angiotensin II receptors in renal proximal tubule. Journal of Clinical Investigation. 1995;95:2012-2019.
Chen J, Chen JK, Nagai K, Plieth D, Tan M, Lee TC, Threadgill DW, Neilson EG and Harris RC. EGFR Signaling Promotes TGFβ-Dependent Renal Fibrosis. J Am Soc Nephrol. 2012;23:215-24.
Christensen EI and Birn H. Megalin and cubilin: multifunctional endocytic receptors. Nature reviews Molecular cell biology. 2002;3:256-66.
Christlieb AR, Kaldany A and D'Elia JA. Plasma renin activity and hypertension in diabetes mellitus. Diabetes. 1976;25:969-74.
Comper WD and Glasgow EF. Charge selectivity in kidney ultrafiltration. Kidney Int. 1995;47:1242-51.
Cosgrove D, Meehan DT, Grunkemeyer JA, Kornak JM, Sayers R, Hunter WJ and Samuelson GC. Collagen COL4A3 knockout: a mouse model for autosomal Alport syndrome. Genes & development. 1996;10:2981-92.
Crowley SD, Gurley SB, Herrera MJ, Ruiz P, Griffiths R, Kumar AP, Kim HS, Smithies O, Le TH and Coffman TM. Angiotensin II causes hypertension and cardiac hypertrophy through its receptors in the kidney. Proceedings of the National Academy of Sciences of the United States of America. 2006;103:17985-90.
Culver S, Li C and Siragy HM. Intrarenal Angiotensin-Converting Enzyme: the Old and the New. Current hypertension reports. 2017;19:80.
Dickson LE, Wagner MC, Sandoval RM and Molitoris BA. The proximal tubule and albuminuria: really! J Am Soc Nephrol. 2014;25:443-53.
Dolman ME, Harmsen S, Storm G, Hennink WE and Kok RJ. Drug targeting to the kidney: Advances in the active targeting of therapeutics to proximal tubular cells. Advanced drug delivery reviews. 2010;62:1344-57.
Durvasula RV, Petermann AT, Hiromura K, Blonski M, Pippin J, Mundel P, Pichler R, Griffin S, Couser WG and Shankland SJ. Activation of a local tissue angiotensin system in podocytes by mechanical strain. Kidney Int. 2004;65:30-9.
Durvasula RV and Shankland SJ. Activation of a local renin angiotensin system in podocytes by glucose. Am J Physiol Renal Physiol. 2008;294:F830-9.
Ferrario CM, Jessup J, Chappell MC, Averill DB, Brosnihan KB, Tallant EA, Diz DI and Gallagher PE. Effect of angiotensin-converting enzyme inhibition and angiotensin II receptor blockers on cardiac angiotensin-converting enzyme 2. Circulation. 2005;111:2605-10.
Fisher ND, Price DA, Litchfield WR, Williams GH and Hollenberg NK. Renal response to captopril reflects state of local renin system in healthy humans. Kidney Int. 1999;56:635-41.
Fogo AB. Renal fibrosis and the renin-angiotensin system. Advances in nephrology from the Necker Hospital. 2001;31:69-87.
Franssen EJ, Koiter J, Kuipers CA, Bruins AP, Moolenaar F, de Zeeuw D, Kruizinga WH, Kellogg RM and Meijer DK. Low molecular weight proteins as carriers for renal drug targeting. Preparation of drug-protein conjugates and drug-spacer derivatives and their catabolism in renal cortex homogenates and lysosomal lysates. J Med Chem. 1992;35:1246-59.
Franssen EJ, van Amsterdam RG, Visser J, Moolenaar F, de Zeeuw D and Meijer DK. Low molecular weight proteins as carriers for renal drug targeting: naproxen-lysozyme. Pharmaceutical research. 1991;8:1223-30.
Giani JF, Janjulia T, Kamat N, Seth DM, Blackwell WL, Shah KH, Shen XZ, Fuchs S, Delpire E, Toblli JE, Bernstein KE, McDonough AA and Gonzalez-Villalobos RA. Renal angiotensin-converting enzyme is essential for the hypertension induced by nitric oxide synthesis inhibition. J Am Soc Nephrol. 2014;25:2752-63.
Gonzalez AA, Green T, Luffman C, Bourgeois CRT, Gabriel Navar L and Prieto MC. Renal medullary cyclooxygenase-2 and (pro)renin receptor expression during angiotensin II-dependent hypertension. Am J Physiol Renal Physiol. 2014;307:F962-70.
Gonzalez-Villalobos RA, Janjoulia T, Fletcher NK, Giani JF, Nguyen MT, Riquier-Brison AD, Seth DM, Fuchs S, Eladari D, Picard N, Bachmann S, Delpire E, Peti-Peterdi J, Navar LG, Bernstein KE and McDonough AA. The absence of intrarenal ACE protects against hypertension. The Journal of clinical investigation. 2013;123:2011-23.
Goorno WE, Rector FC, Jr. and Seldin DW. Relation of renal gluconeogenesis to ammonia production in the dog and rat. The American journal of physiology. 1967;213:969-74.
Grima M, Ingert C, Michel B, Barthelmebs M and Imbs JL. Renal tissue angiotensins during converting enzyme inhibition in the spontaneously hypertensive rat. Clinical and experimental hypertension (New York, NY : 1993). 1997;19:671-85.
Grobe JL, Mecca AP, Lingis M, Shenoy V, Bolton TA, Machado JM, Speth RC, Raizada MK and Katovich MJ. Prevention of angiotensin II-induced cardiac remodeling by angiotensin-(1-7). American journal of physiology Heart and circulatory physiology. 2007;292:H736-42.
Grobe N, Weir NM, Leiva O, Ong FS, Bernstein KE, Schmaier AH, Morris M and Elased KM. Identification of prolyl carboxypeptidase as an alternative enzyme for processing of renal angiotensin II using mass spectrometry. American journal of physiology Cell physiology. 2013;304:C945-53.
Guo Y, Yuan H, Claudio NM, Kura S, Shakerdge N, Mempel TR, Bacskai BJ and Josephson L. PEG-like nanoprobes: multimodal, pharmacokinetically and optically tunable nanomaterials. PloS one. 2014;9:e95406.
Gurley SB and Coffman TM. The renin-angiotensin system and diabetic nephropathy. Seminars in nephrology. 2007;27:144-52.
Gurley SB, Riquier ADM, Schnermann J, Sparks MA, Allen AM, Haase VH, Snouwaert JN, Le TH, McDonough AA, Koller BH and Coffman TM. AT(1A) Angiotensin Receptors in the Renal Proximal Tubule Regulate Blood Pressure. Cell metabolism. 2011;13:469-75.
Sun, Y., et al., "Cationic Nanoparticles Directly Bind Angiotensin-Converting Enzyme 2 and Induce Acute Lung Injury in Mice", Part. Fibre. Toxicol., 2015, vol. 12, No. 4, pp. 1-13.
International Search Report and Written Opinion for PCT/US2018/014991 dated Apr. 12, 2018.

* cited by examiner

SEQUENCE LISTING

```
<160> NUMBER OF SEQ ID NOS: 9

<210> SEQ ID NO 1
<211> LENGTH: 805
<212> TYPE: PRT
<213> ORGANISM: Homo sapiens

<400> SEQUENCE: 1

Met Ser Ser Ser Ser Trp Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
                100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
        130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
                180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
        210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285
```

-continued

```
Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
690                 695                 700
```

-continued

```
Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
            725                 730                 735

Pro Pro Val Ser Ile Trp Leu Ile Val Phe Gly Val Met Gly Val
            740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
            805
```

<210> SEQ ID NO 2
<211> LENGTH: 805
<212> TYPE: PRT
<213> ORGANISM: Mus musculus

<400> SEQUENCE: 2

```
Met Ser Ser Ser Ser Trp Leu Leu Leu Ser Leu Val Ala Val Thr Thr
1               5                   10                  15

Ala Gln Ser Leu Thr Glu Glu Asn Ala Lys Thr Phe Leu Asn Asn Phe
            20                  25                  30

Asn Gln Glu Ala Glu Asp Leu Ser Tyr Gln Ser Ser Leu Ala Ser Trp
            35                  40                  45

Asn Tyr Asn Thr Asn Ile Thr Glu Glu Asn Ala Gln Lys Met Ser Glu
    50                  55                  60

Ala Ala Ala Lys Trp Ser Ala Phe Tyr Glu Glu Gln Ser Lys Thr Ala
65                  70                  75                  80

Gln Ser Phe Ser Leu Gln Glu Ile Gln Thr Pro Ile Ile Lys Arg Gln
            85                  90                  95

Leu Gln Ala Leu Gln Gln Ser Gly Ser Ser Ala Leu Ser Ala Asp Lys
            100                 105                 110

Asn Lys Gln Leu Asn Thr Ile Leu Asn Thr Met Ser Thr Ile Tyr Ser
        115                 120                 125

Thr Gly Lys Val Cys Asn Pro Lys Asn Pro Gln Glu Cys Leu Leu Leu
    130                 135                 140

Glu Pro Gly Leu Asp Glu Ile Met Ala Thr Ser Thr Asp Tyr Asn Ser
145                 150                 155                 160

Arg Leu Trp Ala Trp Glu Gly Trp Arg Ala Glu Val Gly Lys Gln Leu
            165                 170                 175

Arg Pro Leu Tyr Glu Glu Tyr Val Val Leu Lys Asn Glu Met Ala Arg
            180                 185                 190

Ala Asn Asn Tyr Asn Asp Tyr Gly Asp Tyr Trp Arg Gly Asp Tyr Glu
        195                 200                 205

Ala Glu Gly Ala Asp Gly Tyr Asn Tyr Asn Arg Asn Gln Leu Ile Glu
    210                 215                 220

Asp Val Glu Arg Thr Phe Ala Glu Ile Lys Pro Leu Tyr Glu His Leu
225                 230                 235                 240

His Ala Tyr Val Arg Arg Lys Leu Met Asp Thr Tyr Pro Ser Tyr Ile
            245                 250                 255

Ser Pro Thr Gly Cys Leu Pro Ala His Leu Leu Gly Asp Met Trp Gly
            260                 265                 270
```

```
Arg Phe Trp Thr Asn Leu Tyr Pro Leu Thr Val Pro Phe Ala Gln Lys
            275                 280                 285

Pro Asn Ile Asp Val Thr Asp Ala Met Met Asn Gln Gly Trp Asp Ala
    290                 295                 300

Glu Arg Ile Phe Gln Glu Ala Glu Lys Phe Phe Val Ser Val Gly Leu
305                 310                 315                 320

Pro His Met Thr Gln Gly Phe Trp Ala Asn Ser Met Leu Thr Glu Pro
                325                 330                 335

Ala Asp Gly Arg Lys Val Val Cys His Pro Thr Ala Trp Asp Leu Gly
            340                 345                 350

His Gly Asp Phe Arg Ile Lys Met Cys Thr Lys Val Thr Met Asp Asn
        355                 360                 365

Phe Leu Thr Ala His His Glu Met Gly His Ile Gln Tyr Asp Met Ala
370                 375                 380

Tyr Ala Arg Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Pro Ser Asp Phe Gln Glu Asp Ser
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Arg Gly Glu Ile Pro Lys Glu Gln Trp Met Lys Lys Trp Trp Glu Met
465                 470                 475                 480

Lys Arg Glu Ile Val Gly Val Val Glu Pro Leu Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Ile Tyr Gln Phe Gln Phe Gln Glu Ala
        515                 520                 525

Leu Cys Gln Ala Ala Lys Tyr Asn Gly Ser Leu His Lys Cys Asp Ile
530                 535                 540

Ser Asn Ser Thr Glu Ala Gly Gln Lys Leu Leu Lys Met Leu Ser Leu
545                 550                 555                 560

Gly Asn Ser Glu Pro Trp Thr Lys Ala Leu Glu Asn Val Val Gly Ala
                565                 570                 575

Arg Asn Met Asp Val Lys Pro Leu Leu Asn Tyr Phe Gln Pro Leu Phe
            580                 585                 590

Asp Trp Leu Lys Glu Gln Asn Arg Asn Ser Phe Val Gly Trp Asn Thr
        595                 600                 605

Glu Trp Ser Pro Tyr Ala Asp Gln Ser Ile Lys Val Arg Ile Ser Leu
    610                 615                 620

Lys Ser Ala Leu Gly Ala Asn Ala Tyr Glu Trp Thr Asn Asn Glu Met
625                 630                 635                 640

Phe Leu Phe Arg Ser Ser Val Ala Tyr Ala Met Arg Lys Tyr Phe Ser
                645                 650                 655

Ile Ile Lys Asn Gln Thr Val Pro Phe Leu Glu Glu Asp Val Arg Val
            660                 665                 670

Ser Asp Leu Lys Pro Arg Val Ser Phe Tyr Phe Phe Val Thr Ser Pro
        675                 680                 685
```

Gln Asn Val Ser Asp Val Ile Pro Arg Ser Glu Val Glu Asp Ala Ile
690                 695                 700

Arg Met Ser Arg Gly Arg Ile Asn Asp Val Phe Gly Leu Asn Asp Asn
705                 710                 715                 720

Ser Leu Glu Phe Leu Gly Ile His Pro Thr Leu Glu Pro Pro Tyr Gln
                725                 730                 735

Pro Pro Val Thr Ile Trp Leu Ile Ile Phe Gly Val Val Met Ala Leu
            740                 745                 750

Val Val Val Gly Ile Ile Ile Leu Ile Val Thr Gly Ile Lys Gly Arg
                755                 760                 765

Lys Lys Lys Asn Glu Thr Lys Arg Glu Glu Asn Pro Tyr Asp Ser Met
770                 775                 780

Asp Ile Gly Lys Gly Glu Ser Asn Ala Gly Phe Gln Asn Ser Asp Asp
785                 790                 795                 800

Ala Gln Thr Ser Phe
                805

<210> SEQ ID NO 3
<211> LENGTH: 619
<212> TYPE: PRT
<213> ORGANISM: Homo sapiens

<400> SEQUENCE: 3

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
        260                 265                 270

Arg Phe Trp Thr Asn Leu Tyr Ser Leu Thr Val Pro Phe Gly Gln Lys
    275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
        340                 345                 350

Lys Gly Asp Phe Arg Ile Leu Met Cys Thr Lys Val Thr Met Asp Asp
    355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
        420                 425                 430

Glu Thr Glu Ile Asn Phe Leu Leu Lys Gln Ala Leu Thr Ile Val Gly
    435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
        500                 505                 510

Ile Arg Tyr Tyr Thr Arg Thr Leu Tyr Gln Phe Gln Phe Gln Glu Ala
    515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
        580                 585                 590

Thr Trp Leu Lys Asp Gln Asn Lys Asn Ser Phe Val Gly Trp Ser Thr
    595                 600                 605

Asp Trp Ser Pro Tyr Ala Asp Gln Ser Ile Lys
    610                 615

<210> SEQ ID NO 4
<211> LENGTH: 605
<212> TYPE: PRT
<213> ORGANISM: Homo sapiens

<400> SEQUENCE: 4

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
                100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
                180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
        210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
                260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415
```

```
His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly
        595                 600                 605

<210> SEQ ID NO 5
<211> LENGTH: 46
<212> TYPE: PRT
<213> ORGANISM: Artificial
<220> FEATURE:
<223> OTHER INFORMATION: Variant of Streptococcal G-protein albumin
      binding domain III

<400> SEQUENCE: 5

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 6
<211> LENGTH: 232
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 7
<211> LENGTH: 107
<212> TYPE: PRT
<213> ORGANISM: Homo sapien

<400> SEQUENCE: 7

Gly Gln Pro Arg Glu Pro Gln Val Tyr Thr Ser Pro Pro Ser Arg Asp
1               5                   10                  15

Glu Leu Thr Lys Asn Gln Val Ser Leu Arg Cys His Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Lys Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 8
<211> LENGTH: 107
<212> TYPE: PRT
<213> ORGANISM: Artificial
<220> FEATURE:
<223> OTHER INFORMATION: Modified amino acid sequence of the monomeric,
      disulfide-stabilized mCH3 fragment of human IgG

<400> SEQUENCE: 8

Gly Gln Cys Arg Glu Pro Gln Val Tyr Thr Ser Pro Pro Ser Arg Asp
1               5                   10                  15

Glu Leu Thr Lys Asn Gln Val Ser Leu Arg Cys His Val Lys Gly Phe
            20                  25                  30

Tyr Pro Ser Asp Ile Ala Val Glu Trp Glu Ser Asn Gly Gln Pro Glu
        35                  40                  45

```
Asn Asn Tyr Lys Thr Thr Lys Pro Val Leu Asp Ser Asp Gly Ser Phe
    50              55                  60

Phe Leu Tyr Ser Lys Leu Thr Val Asp Lys Ser Arg Trp Gln Gln Gly
65              70                  75                      80

Asn Val Phe Ser Cys Ser Val Met His Glu Cys Leu His Asn His Tyr
                85              90                  95

Thr Gln Lys Ser Leu Ser Leu Ser Pro Gly Lys
                100             105

<210> SEQ ID NO 9
<211> LENGTH: 205
<212> TYPE: PRT
<213> ORGANISM: Homo sapiens

<400> SEQUENCE: 9

Leu Glu Lys Cys Cys Ala Ala Asp Pro His Glu Cys Tyr Ala Lys
1               5                   10                  15

Val Phe Asp Glu Phe Lys Pro Leu Val Glu Glu Pro Gln Asn Leu Ile
            20                  25                  30

Lys Gln Asn Cys Glu Leu Phe Glu Gln Leu Gly Glu Tyr Lys Phe Gln
            35                  40                  45

Asn Ala Leu Leu Val Arg Tyr Thr Lys Lys Val Pro Gln Val Ser Thr
    50              55                  60

Pro Thr Leu Val Glu Val Ser Arg Asn Leu Gly Lys Val Gly Ser Lys
65              70                  75                      80

Cys Cys Lys His Pro Glu Ala Lys Arg Met Pro Cys Ala Glu Asp Cys
                85                  90                  95

Leu Ser Val Phe Leu Asn Gln Leu Cys Val Leu His Glu Lys Thr Pro
                100                 105                 110

Val Ser Asp Arg Val Thr Lys Cys Cys Thr Glu Ser Leu Val Asn Gly
            115                 120                 125

Arg Pro Cys Phe Ser Ala Leu Glu Val Asp Glu Thr Tyr Val Pro Lys
    130                 135                 140

Glu Phe Asn Ala Glu Thr Phe Thr Phe His Ala Asp Ile Cys Thr Leu
145                 150                 155                 160

Ser Glu Lys Glu Arg Gln Ile Lys Lys Gln Thr Ala Leu Val Glu Leu
                165                 170                 175

Val Lys His Lys Pro Lys Ala Thr Lys Glu Gln Leu Lys Ala Val Met
            180                 185                 190

Asp Asp Phe Ala Ala Phe Val Glu Lys Cys Cys Lys Ala
            195                 200                 205
```

ACTIVE LOW MOLECULAR WEIGHT VARIANTS OF ANGIOTENSIN CONVERTING ENZYME 2 (ACE2)

CROSS-REFERENCE TO RELATED PATENT APPLICATIONS

This application claims the benefit of priority under 35 U.S.C. § 119(e) to U.S. Provisional Application No. 62/449,857, filed on Jan. 24, 2017, the content of which is incorporated herein by reference in its entirety.

STATEMENT REGARDING FEDERALLY SPONSORED RESEARCH OR DEVELOPMENT

This invention was made with government support under grant number R01 DK080089 awarded by the National Institutes of Health. The government has certain rights in the invention.

BACKGROUND

The field of the invention relates to angiotensin converting enzyme 2 (ACE2) and variants of ACE2 for reducing plasma levels of Angiotensin II (1-8) and/or for increasing plasma levels of Angiotensin (1-7) in a subject in need thereof. The disclosed variants of ACE2 may include fragments of ACE2 having ACE2 biological activity for converting AngII (1-8) to Ang (1-7) and having a lower molecular weight than full-length ACE2, which normally is not filtered through the glomerulus and which lower molecular weight permits the fragments of ACE2 to be filtered through the glomerulus. The disclosed variants of ACE2 may be useful for treating conditions that include but are not limited to diabetic and non-diabetic chronic kidney disease, acute renal failure and its prevention, chronic kidney disease, glomerulonephritis, severe hypertension, scleroderma and its skin, pulmonary, kidney and hypertensive complications, malignant hypertension, renovascular hypertension secondary to renal artery stenosis, idiopathic pulmonary fibrosis, liver fibrosis such as in liver cirrhosis patients, an aortic aneurysm, cardiac fibrosis and remodeling, left ventricular hypertrophy, and an acute stroke.

Activation of the renin angiotensin system (RAS) plays a major role in the pathogenesis of hypertension, cardiovascular disease, diabetic kidney disease and the progression of CKD to ESRD[1-3]. Moreover, in acute renal failure the RAS is also activated[4-7]. There is a need for new approaches to counteract RAS over-activity that expand and improve on the existing approaches based primarily on blocking formation of Ang II formation or blocking the action of Ang II. We have been at the forefront of proposing therapies aimed at promoting the degradation of Ang II[8-13]. An important biological effect of ACE2 is to convert AngII(1-8) to Ang (1-7), a process that tends to lower AngII(1-8) and therefore prevents the potentially detrimental actions of this peptide. In addition, Ang(1-7) is formed as a result of Ang II(1-8) cleavage and this peptide, by directly activating the Mas receptor, has tissue protective functions that are generally opposite to those of AngII(1-8). Indeed, there is increasing evidence that Ang(1-7) has a vast array of potential therapeutic applications and this also emphasizes the importance of Ang(1-7) forming enzymes as potential therapeutic targets with the dual advantage of degrading Ang II and forming Ang(1-7).

Years ago we and others have purified and produced murine ACE2 as a way to circumvent the immunogenicity[14] that we observed in our initial studies using for the first time human ACE2 given to mice with hypertension induced by AngII infusions[13]. In recent studies we examined the kidney effects of murine recombinant ACE2 given to mice with streptozotocin-induced diabetic kidney disease. (See Wysocki et al., Angiotensin-converting enzyme 2 amplification limited to circulation does not protect mice from development of diabetic nephropathy," Kidney Int. 2016 Dec. 4. Pii: S0085-2538(16)30565-8, the content of which is incorporated herein by reference in its entirety). Two approaches were used in this study: amplification of circulating ACE2 by intraperitoneal daily injections for 4 weeks and by ACE2 gene delivery[15]. Delivery of ACE2 using minicircles resulted in a long-term sustained and profound increase in serum ACE2 activity and enhanced ability to metabolize an acute Ang II(1-8) load. In mice with STZ-induced diabetes pretreated with minicircle ACE2, ACE2 protein in plasma increased markedly and this was associated with a more than 100-fold increase in serum ACE2 activity. However, minicircle ACE2 did not result in changes in urinary ACE2 activity as compared to untreated diabetic mice. Albuminuria, glomerular mesangial expansion, glomerular cellularity and glomerular size, were all increased to a similar extent in minicircle ACE2-treated and untreated diabetic mice, as compared to non-diabetic controls[10]. Thus, a profound augmentation of ACE2 confined to the circulation failed to ameliorate the glomerular lesions and hyperfiltration characteristic of early diabetic kidney disease despite months of sustained very high plasma ACE2 levels. These findings emphasize the importance of targeting the kidney rather than the circulatory renin angiotensin system to combat early stages of diabetic kidney disease and kidney disease in general. The large molecular size of recombinant ACE2 renders it non-filterable by a normal glomerulus or in early forms of kidney disease, a time critical to intervene to prevent disease progression In more advanced glomerular kidney disease, by contrast, we have been able to show that infused rACE2 can be recovered in the urine[10]. At this late stage of advanced disease, it is difficult to reverse kidney alterations and reverse fibrosis. Therefore, to circumvent this limitation we designed shorter forms of ACE2 that are much more suitable to treat kidney disease and provide better tissue penetration to other organs such as lungs and the heart.

Based on our findings we have created forms of ACE2 of shorter molecular size that are deliverable to the kidney prior to the development of marked alterations in glomerular permeability and better delivered to the kidney in all instances. ACE2 is typically observed as a 110 kD protein which is not filterable by the kidney and appears in the urine as a shedding product from the renal apical tubular membrane of the kidney where ACE2 is abundantly expressed[9-11,16]. We have developed smaller molecular weight recombinant ACE2 proteins that are very active. This means that they retain full activity and potential therapeutic use when the goal is to increase ACE2 activity not only in the systemic circulation, just like it is done by the already available human recombinant intact ACE2, but also rather they are unique in that their smaller size makes them deliverable to the kidney by glomerular filtration and thus better for the treatment of kidney disease and tissue penetration of other organs as well.

We have shown that decreasing the size of ACE2 renders it easily filterable through the glomerular barrier in states of mild increases in glomerular permeability, such as acute kidney injury or in early phases of diabetic kidney disease i.e. microalbuminuric stage. The overarching goal is to develop a form of shorter ACE2 that can be delivered easily to the kidney and therefore combat kidney disease This approach is distinctive and complimentary to currently used ACE inhibitors and AT1 blockers. We postulate that enhancing the degradation of Ang II offers the distinctive advantage of leading to the formation of Ang 1-7, a renoprotective peptide, and is also a more natural physiologic approach than blocking the formation or action of Ang II or its receptors as currently done with existing agents. As a way to increase tubular reabsorption of the short ACE2 fragments filterable through the glomerulus and therefore enhance their kidney uptake, the short ACE2 fragments will be conjugated to low molecular fusion polypeptides. These fusion polypeptides include, but are not limited to, Fc (constant fragment of human IgG), the DIII domain of human serum albumin and lysozyme. All of those polypeptides have been shown to be reabsorbed on apical surface of the kidney tubules by receptor-mediated endocytosis. The subject matter of this application is discussed further herein.

SUMMARY

Disclosed are variants of ACE2, pharmaceutical compositions comprising the variants of ACE2, and treatment methods for reducing Angiotensin II (1-8) plasma levels and/or increasing Angiotensin (1-7) plasma levels in a subject in need thereof. The disclosed variants of ACE2 may include polypeptide fragments of ACE2 having ACE2 activity for converting AngII(1-8) to Ang(1-7). The polypeptide fragments of ACE2 preferably have a molecular weight that is low enough such that the polypeptide fragments of ACE2 can be filtered through the glomerulus and delivered to the kidney. In some embodiments, the polypeptide fragments have a molecular weight of less than a 70 kD, we have best studied a compound that we term A1-619 with a molecular weight of 69 kD and one that we term 1-605 with a molecular weight of about 65 kD, 60 kD, 55 kD, or 50 kD. In the disclosed methods, the subject is administered the variant of ACE2 or a pharmaceutic composition comprising the variant of ACE2 in a suitable pharmaceutical carrier. Subjects suitable for the disclosed methods of treatment may include subjects having or at risk for developing diabetic and non-diabetic chronic kidney disease, acute renal failure and its prevention, chronic kidney disease, glomerulonephritis, severe hypertension, scleroderma and its skin, pulmonary, kidney and hypertensive complications, malignant hypertension, renovascular hypertension secondary to renal artery stenosis, idiopathic pulmonary fibrosis, liver fibrosis such as in liver cirrhosis patients, an aortic aneurysm, cardiac fibrosis and remodeling, left ventricular hypertrophy, and an acute stroke.

Figure 1:
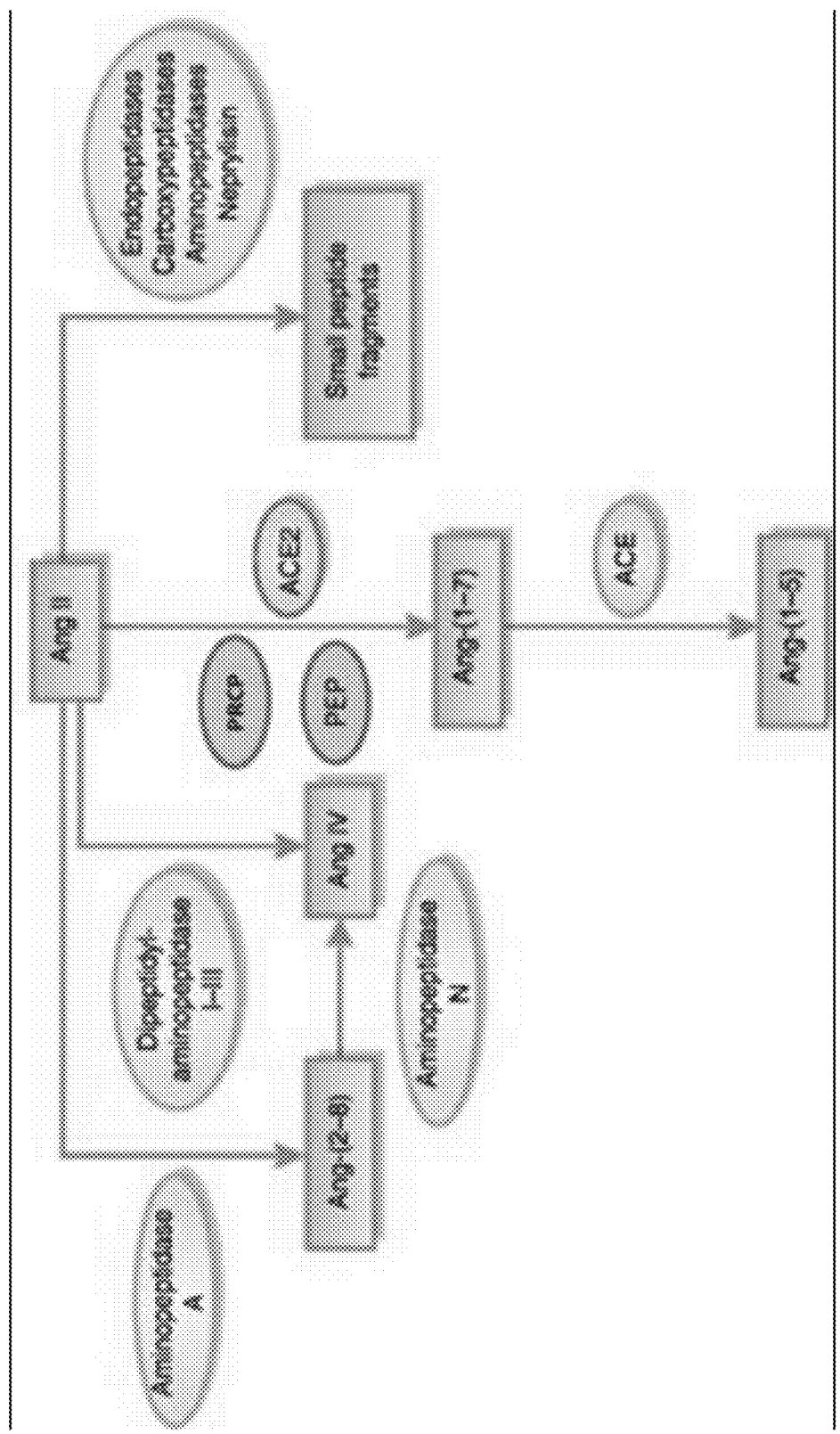
FIG. 1. Angiotensin II (Ang II) degradation pathways. Scheme of the enzymes involved in the metabolism of Ang peptides. Ang II is degraded by ACE2, PRCP and PEP to form Ang-(1-7), which subsequently can be degraded by ACE to form Ang-(1-5). Other pathways of Ang II degradation include aminopeptidase A to Ang-(2-8), dipeptidyl-aminopeptidase I-III to Ang IV, and neprilysin and peptidases to small peptide products. Batlle et al.[3].
Figure 2:
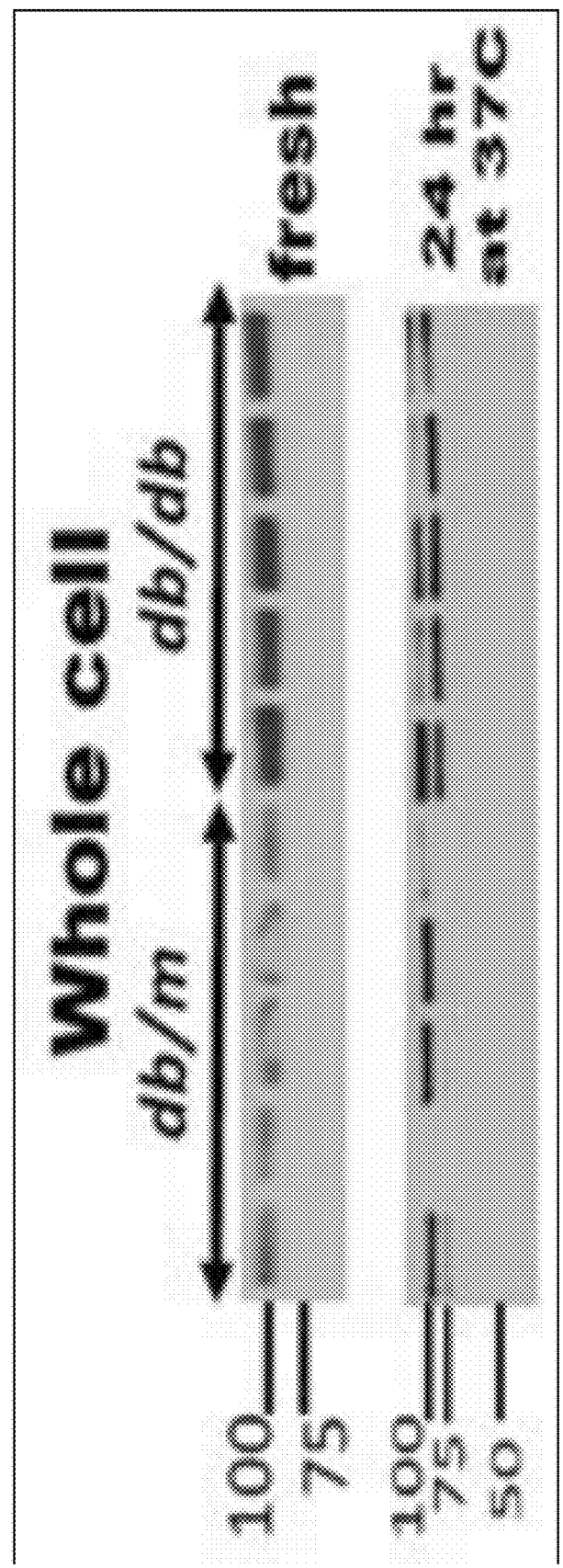
FIG. 2. (Upper panel) Freshly isolated whole kidney cortex lysates collected from db/m and db/db mice (n=5 in each group) were probed in Western blot with ACE2 specific antibody showing a single immunoreactive band at ~110 kD. (Lower panel) Whole kidney lysates were incubated for 24 hours at 37 C and then subjected to Western blot analysis. A second ACE2 immunoreactive band at around 75 kD appeared while the ~110 kD band gradually goes away.
Figure 3:
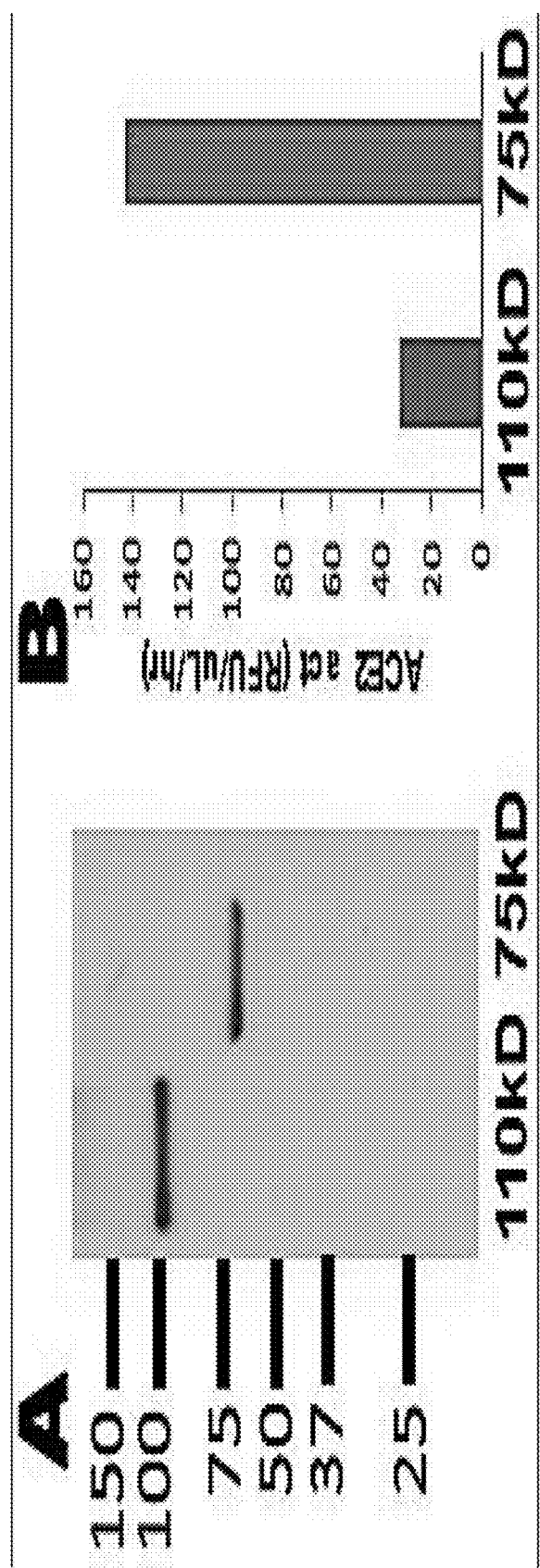
FIG. 3. In two concentrated ultrafiltration fractions of WT mouse urine probed with ACE2-specific antibody in WB (Panel A), ACE2 enzyme activity was measured (Panel B). The concentrated fraction containing the 75 kD ACE2 protein (blue bar) had higher ACE2 activity than the fraction containing the 110 kD protein concentrated to the same proportional volume as the 75 kD fraction.

The disclosed peptides may include an N-terminal esterification (e.g., a phosphoester modification) or a pegylation modification, for example, to enhance plasma stability (e.g. resistance to exopeptidases) and/or to reduce immunogenicity.

A "deletion" refers to a change in a reference amino acid sequence (e.g., SEQ ID NO:1 or SEQ ID NO:2) that results in the absence of one or more amino acid residues. A deletion removes at least 1, 2, 3, 4, 5, 10, 20, 50, 100, or 200 amino acids residues or a range of amino acid residues bounded by any of these values (e.g., a deletion of 5-10 amino acids). A deletion may include an internal deletion or a terminal deletion (e.g., an N-terminal truncation or a C-terminal truncation of a reference polypeptide). A "variant" of a reference polypeptide sequence may include a deletion relative to the reference polypeptide sequence. For example, SEQ ID NO:3 (amino acids 1-619) and SEQ ID NO:4 (amino acids 1-605) include C-terminal deletions relative to reference sequence SEQ ID NO:1 (amino acids 1-805).

The words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues or a range of amino acid residues bounded by any of these values (e.g., an insertion or addition of 5-10 amino acids). A "variant" of a reference polypeptide sequence may include an insertion or addition relative to the reference polypeptide sequence.

A "fusion polypeptide" refers to a polypeptide comprising at the N-terminus, the C-terminus, or at both termini of its amino acid sequence a heterologous amino acid sequence, for example, a heterologous amino acid sequence that extends the half-life of the fusion polypeptide in serum. A "variant" of a reference polypeptide sequence may include a fusion polypeptide comprising the reference polypeptide.

A "fragment" is a portion of an amino acid sequence which is identical in sequence to but shorter in length than a reference sequence (e.g., SEQ ID NO:1 or SEQ ID NO:2). A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, or 500 contiguous amino acid residues of a reference polypeptide; or a fragment may comprise no more than 5, 10, 15, 20, 25, 30, 40, 50, 60, 70, 80, 90, 100, 150, 250, or 500 contiguous amino acid residues of a reference polypeptide; or a fragment may comprise a range of contiguous amino acid residues of a reference polypeptide bounded by any of these values (e.g., 40-80 contiguous amino acid residues). Fragments may be preferentially selected from certain regions of a molecule. The term "at least a fragment" encompasses the full length polypeptide. A "variant" of a reference polypeptide sequence may include a fragment of the reference polypeptide sequence. For example, SEQ ID NO:3 (amino acids 1-619) and SEQ ID NO:4 (amino acids 1-605) comprise fragments of reference sequence SEQ ID NO:1 (amino acids 1-805).

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 100, at least 150, at least 200, at least 250, at least 300, at least 350, at least 400, at least 450, at least 500, at least 550, at least 600, at least 650, or at least 700 contiguous amino acid residues; or a fragment of no more than 15, 20, 30, 40, 50, 100, 150, 200, 250, 300, 350, 400, 450, 500, 550, 600, 650, or 700 amino acid residues; or over a range bounded by any of these values (e.g., a range of 500-600 amino acid residues) Such lengths are exemplary only, and it is understood that any fragment length supported by the sequences shown herein, in the tables, figures or Sequence Listing, may be used to describe a length over which percentage identity may be measured.

In some embodiments, a "variant" of a particular polypeptide sequence may be defined as a polypeptide sequence having at least 20% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides, or range of percentage identity bounded by any of these values (e.g., range of percentage identity of 80-99%).

The disclosed methods of treatment and pharmaceutical composition utilize and/or include angiotensin converting enzyme 2 (ACE2) or variants thereof such as fragments of ACE2. The nucleotide sequence of the human ACE2 gene is available from the National Center for Biotechnology Information of the National Institutes of Health. The location of the human ACE2 gene is provided as NC_000023.11 (15494525 ... 15602069, complement). ACE2, isoform 1, is a transmembrane protein which is expressed first as a precursor polypeptide having the amino acid sequence (SEQ ID NO:1). The mouse (*Mus musculus*) homolog of ACE2 has the following amino acid sequence (SEQ ID NO:2):

Amino acids 1-17 are a leader peptide which is cleaved from mature ACE2. Amino acids 18-740 are extracellular. Amino acids 741-761 form a helical transmembrane sequence. Amino acids 762-805 are cytoplasmic. Natural variants of ACE2 are contemplated herein and may include the natural variant K26R and the natural variant N638S. Natural isoforms of ACE2 also are contemplated herein include isoform 2 having the following differences relative to isoform 1: F555L and Δ556-805. The variants of ACE2 disclosed herein, including fragments of ACE2, may have or lack one or more of these amino acid sequences of ACE2.

Fusion polypeptides of ACE2 or variants thereof are disclosed herein. The fusion polypeptide of ACE2 or a variant thereof may include the amino acid sequence of ACE2 or a variant thereof (e.g., the amino acid sequence of a fragment of ACE2) fused to a heterologous amino acid sequence. Preferably, the heterologous amino acid sequence increases the half-life of the fusion polypeptide in plasma.

The disclosed fusion polypeptides may comprise the amino acid sequence of ACE2 or a variant thereof (e.g., the amino acid sequence of a fragment of ACE2) fused directly to a heterologous amino acid sequence or fused via a linker sequence. Suitable linker sequences may include amino acid sequences of 5, 6, 7, 8, 9, 10, 11, 12, 13, 14, or 15 amino acids or more, or a range bounded by any of these values (e.g., a linker of 5-15 amino acids). In some embodiments, the linker sequence comprises only glycine and serine residues.

Fusion polypeptides disclosed herein include the amino acid sequence of ACE2 or a variant thereof fused to the amino acid sequence of an antibody or to one or more fragments of an antibody, for example, the Fc portion of an antibody (constant fragment of human IgG) which preferably is devoid of its hinge region to prevent dimerization of the fusion polypeptide (e.g., SEQ ID NO:6). Fusion of short ACE2 with Fc (e.g., SEQ ID NO:6) or the monomeric CH3 Fc derivate (e.g., SEQ ID NO:7 or SEQ ID NO:8) can enable its delivery through a functional FcRn-dependent transport pathway in the lung that can be used locally for more efficient administration in the treatment of lung fibrosis. Fusion polypeptides disclosed herein include also include the amino acid sequence of ACE2 or a variant thereof fused to serum albumin or a fragment thereof, for example domain III of human serum albumin or a fragment thereof (e.g., SEQ ID NO:9). Fusion polypeptides disclosed herein include the amino acid sequence of ACE2 or a variant thereof fused to streptococcal protein G or a fragment thereof such as the C-terminal albumin binding domain 3 (ABD3) of streptococcal protein G (e.g., ABD3 from strain G148 or the ABD035 derivative (SEQ ID NO:5). (See, e.g., Nilvebrant et al., Comput. Struct. Biotechnol. J. 2013, Volume No:6, Issue: 7, Mar. 2013, pages 1-8; the content of which is incorporated herein by reference in its entirety).

Fusion polypeptide disclosed herein may include an amino acid tag sequence, for example, which may be utilized for purifying and or identifying the fusion polypeptide. Suitable amino acid tag sequences may include, but are not limited to, histidine tag sequences comprising 5-10 histidine residues.

ACE2 is a carboxypeptidase which catalyzes the conversion of angiotensin I to angiotensin 1-9, a protein of unknown function, and catalyzes the conversion of angiotensin II (1-8) to angiotensin (1-7) (EC:3.4.17.23), which is a vasodilator. ACE2 also catalyzes the hydrolysis of apelin-13 and dynorphin-13. ACE2 also is the cellular receptor for sudden acute respiratory syndrome (SARS) coronavirus/SARS-CoV and human coronavirus NL63/HCoV-NL63. The variants of ACE2 disclosed herein, including fragments of ACE2, may have or lack one or more of these enzymatic activities of ACE2.

In catalyzing the conversion of angiotensin II (1-8) to angiotensin (1-7), ACE2 catalyzes the following reaction: angiotensin II (1-8)+$H_2O$=angiotensin (1-7)+L-phenylalanine, which removes the C-terminal phenylalanine of angiotensin II (1-8). ACE2 has cofactor binding sites for $Zn^{2+}$ and $Cl^-$. The Michaelis constants ($K_m$) for these reactions are as follows: $K_m$=6.9 μM for angiotensin I; $K_m$=2 μM for angiotensin II; $K_m$=6.8 μM for apelin-13; and $K_m$=5.5 μM for dynorphin-13. The optimum pH for these reactions is 6.5 in the presence of 1 M NaCl, but ACE2 is active at pH 6-9. ACE2 is activated by halide ions chloride and fluoride, but not bromide. ACE2 is inhibited by MLN-4760, cFP_Leu, and EDTA, but not by the ACE inhibitors linosipril, captopril and enalaprilat. The variants of ACE2 disclosed herein, including fragments of ACE2, may have or lack one or more of these enzymatic activities of ACE2. In some embodiments, the variants of ACE2 disclosed herein, including fragments of ACE2, may have a Michaelis constant for one or more of the reactions above which is ±50% of the Michaelis constant for ACE2.

ACE2 exhibits molecular functions that may include: carboxypeptidase activity, endopeptidase activity, glycoprotein binding activity, metallocarboxypeptidase activity, virus receptor binding activity, and zinc ion binding activity. The variants of ACE2 disclosed herein, including fragments of ACE2, have at least one, cleavage of Angiotensin II, but likely all of the molecular and enzymatic functions of ACE2.

Key structure features of ACE2 may include one or more of the following: amino acid position 169—chloride binding site; amino acid position 273—substrate binding site; amino acid position 345 substrate binding site; amino acid position 346—substrate binding site via a carbonyl oxygen; amino acid position 371—substrate binding site; amino acid position 374—metal binding site (e.g., $Zn^{2+}$); amino acid position 375—active site; amino acid position 378—catalytic metal binding site (e.g. $Zn^{2+}$); amino acid position 402—catalytic metal binding site (e.g. $Zn^{2+}$); amino acid position 477—chloride binding site; amino acid position 481—chloride binding site; amino acid position 505—active site; and amino acid position 515 substrate binding site. The variants of ACE2 disclosed herein, including fragments of ACE2, may have or lack one or more of these structural features of ACE2.

Key structure features of ACE2 may include one or more of the following: amino acid positions 23-52—helix; amino acid positions 56-77; amino acid positions 78-82—turn; amino acid positions 85-87—helix; amino acid positions 91-100—helix; amino acid positions 104-107—helix; amino acid positions 110-129—helix; amino acid positions 131-134—beta strand; amino acid positions 137-143—beta strand; amino acid positions 144-146—turn; amino acid positions 148-154—helix; amino acid positions 158-171—helix; amino acid positions 173-193—helix; amino acid positions 196-198—beta strand; amino acid positions 199-204—helix; amino acid positions 205-207—turn; amino acid positions 213-215—turn; amino acid positions 220-

251—helix; amino acid positions 253-255—turn; amino acid positions 258-260—beta strand; amino acid positions 264-266—helix; amino acid positions 267-271—beta strand; amino acid positions 279-282—helix; amino acid positions 284-287—turn; amino acid positions 294-297—turn; amino acid positions 298-300—helix; amino acid positions 304-316—helix; amino acid positions 317-319—turn; amino acid positions 327-330—helix; amino acid positions 338-340—beta strand; amino acid positions 347-352—beta strand; amino acid positions 355-359—beta strand; amino acid positions 366-384—helix; amino acid positions 385-387—turn; amino acid positions 390-392—helix; amino acid positions 400-413—helix; amino acid positions 415-420—helix; amino acid positions 422-426—turn; amino acid positions 432-446—helix; amino acid positions 449-465—helix; amino acid positions 466-468—beta strand; amino acid positions 473-483—helix; amino acid positions 486-488—beta strand; amino acid positions 499-502—helix; amino acid positions 504-507—helix; amino acid positions 514-531—helix; amino acid positions 532-534—turn; amino acid positions 539-541—helix; amino acid positions 548-558—helix; amino acid positions 559-562—turn; amino acid positions 566-574—helix; amino acid positions 575-578—beta strand; amino acid positions 582-598—helix; amino acid positions 600-602—beta strand; and amino acid positions 607-609—beta strand. The variants of ACE2 disclosed herein, including fragments of ACE2, may have or lack one or more of these structural features of ACE2.

ACE2 may include one or more of the following amino acid modifications: amino acid position 53—N-linked glycosylation; amino acid position 90—N-linked glycosylation; amino acid position 103—N-linked glycosylation; amino acid positions 133← →141—disulfide bond; amino acid position 322—N-linked glycosylation; amino acid positions 344← →361—disulfide bond; amino acid position 432—N-linked glycosylation; amino acid positions 530← →542; amino acid position 546—N-linked glycosylation; and amino acid position 690—N-linked glycosylation. The variants of ACE2 disclosed herein, including fragments of ACE2, may have or lack one or more of these amino acid modifications of ACE2 and/or may lack the amino acids thusly modified.

ACE2 regulates biological processes that may include: angiotensin catabolism processes in blood, angiotensin maturation processes, angiotensin-mediated drinking behavior processes, positive regulation of cardiac muscle contraction processes, positive regulation of gap junction assembly processes, positive regulation of reactive oxygen species metabolism processes, receptor biosynthesis processes, receptor-mediated virion attachment processes (e.g., coronaviruses), regulation of cardiac conduction processes, regulation of cell proliferation processes, regulation of cytokine production processes, regulation of inflammatory response processes, regulation of systemic arterial blood pressure by renin-angiotensin processes, regulation of vasoconstriction processes, regulation of vasodilation processes, tryptophan transport processes, and viral entry into host cell processes (e.g., coronaviruses). The variants of ACE2 disclosed herein, including fragments of ACE2, may regulate or may fail to regulate one or more of these biological processes.

The disclosed ACE2 variants may include an N-terminal methionine residue that does not occur naturally in the native amino acid for ACE2. For example, the amino acid sequence of ACE2 variants contemplated herein may include an N-terminal deletion relative to the amino acid sequence of full-length ACE2, and further, may be modified to include an N-terminal methionine residue that is not present in the amino acid sequence of full-length ACE2.

The disclosed ACE2 variants may be modified so as to comprise an amino acid sequence, or modified amino acids, or non-naturally occurring amino acids, such that the disclosed ACE2 variants cannot be said to be naturally occurring. In some embodiments, the disclosed ACE2 variants are modified and the modification is selected from the group consisting of acylation, acetylation, formylation, lipoylation, myristoylation, palmitoylation, alkylation, isoprenylation, prenylation, and amidation. An amino acid in the disclosed polypeptides may be thusly modified, but in particular, the modifications may be present at the N-terminus and/or C-terminus of the polypeptides (e.g., N-terminal acylation or acetylation, and/or C-terminal amidation). The modifications may enhance the stability of the polypeptides and/or make the polypeptides resistant to proteolysis.

The disclosed ACE2 variants may be modified to replace a natural amino acid residue by an unnatural amino acid. Unnatural amino acids may include, but are not limited to an amino acid having a D-configuration, an N-methyl-α-amino acid, a non-proteogenic constrained amino acid, or a β-amino acid.

The disclosed ACE2 variants may be modified in order to increase the stability of the ACE2 variants in plasma. For example, the disclosed peptides may be modified in order to make the peptides resistant to peptidases. The disclosed peptides may be modified to replace an amide bond between two amino acids with a non-amide bond. For example, the carbonyl moiety of the amide bond can be replaced by CH2 (i.e., to provide a reduced amino bond: —CH2-NH—). Other suitable non-amide replacement bonds for the amide bond may include, but are not limited to: an endothiopeptide, —C(S)—NH, a phosphonamide, —P(O)OH—NH—), the NH-amide bond can be exchanged by O (depsipeptide, —CO—O—), S (thioester, —CO—S—) or $CH_2$ (ketomethylene, —CO—$CH_2$—). The peptide bond can also be modified as follows: retro-inverso bond (—NH—CO—), methylene-oxy bond (—$CH_2$—), thiomethylene bond (—$CH_2$—S—), carbabond (—$CH_2$—$CH_2$—), hydroxyethylene bond (—CHOH—$CH_2$—) and so on, for example, to increase plasma stability of the peptide sequence (notably towards endopeptidases).

The disclosed ACE2 variants may include a non-naturally occurring N-terminal and/or C-terminal modification. For example, the N-terminal of the disclosed peptides may be modified to include an N-acylation or a N-pyroglutamate modification (e.g., as a blocking modification). The C-terminal end of the disclosed peptides may be modified to include a C-amidation. The disclosed peptides may be conjugated to carbohydrate chains (e.g., via glycosylation to glucose, xylose, hexose), for example, to increase plasma stability (notably, resistance towards exopeptidases).

The variants of ACE2 disclosed herein may be further modified. For example, the polypeptide fragment of ACE2 may be further modified to increase half-life in plasma and/or to enhance delivery to a target (e.g., the kidney, the lungs, the heart, etc.). In some embodiments, the polypeptide fragment is covalently attached to a polyethylene glycol polymer. In other embodiments, the polypeptide fragment may be conjugated to a nanoparticle (e.g., a biogel nanoparticle, a polymer-coated nanobin nanoparticle, and gold nanoparticles). Preferably, the polypeptide fragment of the disclosed methods of treatment and pharmaceutical compositions has a half-live in plasma of at least 6 hours, 12 hours, 1 day, 2 days, 3 days, 4 days, 5 days, 6 days, one week, two week, three weeks, four weeks, or longer. Strategies to improve plasma half-life of peptide and protein drugs are known in the art. (See Werle et al., "Strategies to improve plasma half life time of peptide and protein drugs," Amino Acids 2006 June; 30(4):351-67, the content of which is incorporated herein by reference in its entirety).

Pharmaceutical Compositions

The compositions disclosed herein may include pharmaceutical compositions comprising the presently disclosed bacterial toxins and formulated for administration to a subject in need thereof. Such compositions can be formulated and/or administered in dosages and by techniques well known to those skilled in the medical arts taking into consideration such factors as the age, sex, weight, and condition of the particular patient, and the route of administration.

The compositions may include pharmaceutical solutions comprising carriers, diluents, excipients, and surfactants, as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

The pharmaceutical compositions may be administered therapeutically. In therapeutic applications, the compositions are administered to a patient in an amount sufficient to elicit a therapeutic effect (e.g., a response which cures or at least partially arrests or slows symptoms and/or complications of disease (i.e., a "therapeutically effective dose")).

Novel Active Short ACE2 Fragments

The present inventors have discovered novel fragments of full-length ACE2, molecular weight about 110 kD, with a much shorter molecular weight (less than 70 kD) that have very high enzymatic activity. The disclosed fragments of ACE2 may be utilized in methods of treatment and pharmaceutical compositions. In some embodiments, the disclosed methods may be practiced in order to reduce AngII (1-8) levels in a subject in need thereof. Moreover , there are other substrates other than Angiotensin II that are also cleaved by the novel ACE2 fragments. In the methods, the subject may be a pharmaceutical composition comprising a polypeptide fragment of angiotensin converting enzyme 2 (ACE2, SEQ ID NO:1) in a suitable pharmaceutical carrier. Subjects suitable for the disclosed methods of treatment may include, but are not limited to, subjects having or at risk for developing diabetic and non-diabetic chronic kidney disease, acute renal failure and its prevention, chronic kidney disease, severe hypertension, scleroderma and its skin, pulmonary, kidney and hypertensive complications, malignant hypertension, renovascular hypertension secondary to renal artery stenosis, idiopathic pulmonary fibrosis, an aortic aneurysm, cardiac fibrosis and remodeling, left ventricular hypertrophy, and an acute stroke. The disclosed pharmaceutical compositions may be administered by any suitable method, including but not limited to intravenous infusion and subcutaneously where patients could inject themselves at home. The disclosed pharmaceutical compositions may be administered by inhalation as another route of administration that could be very practical for use to treat idiopathic pulmonary fibrosis and other conditions.

The polypeptide fragment of ACE2 in the disclosed methods of treatment and pharmaceutical compositions has ACE2 activity for converting AngII(1-8) to Ang(1-7). In some embodiments, the polypeptide fragment of ACE2 can be efficiently delivered to the kidneys and may have a higher ACE2 activity than full-length ACE2 which cannot be easily delivered to the kidneys.

Typically, the polypeptide fragment of ACE2 has a molecular weight that is low enough such that the polypeptide fragment of ACE2 can be filtered through the glomerulus and delivered to the kidney. In some embodiments, the polypeptide fragment has a molecular weight of less than about 70 kD, 65 kD, 60 kD, 55 kD, or 50 kD.

The disclosed polypeptide fragments of ACE2 may include a deletion relative to full-length ACE2 (SEQ ID NO:1). The disclosed polypeptide fragments may include a deletion selected from an N-terminal deletion, a C-terminal deletion, and both, relative to full-length ACE2 (SEQ ID NO:1). Further, in some embodiments the disclosed polypeptide fragments may include an internal deletion. The deletion may remove at least about 1, 2, 3, 4, 5, 10, 15, 20, 25, 50, 100, 150, 200 amino acids or more of full-length ACE. In some embodiments, the deletion removes one or more glycosylation sites, and as such, the polypeptide fragments of ACE2 may be less glycosylated than full-length ACE2, further reducing the molecular weight of the polypeptide fragments of ACE2 relative to full-length ACE2.

Illustrative Embodiments

The following embodiments are illustrative and should not be interpreted to limit the scope of the claimed subject matter.

Embodiment 1. A variant of angiotensin converting enzyme 2 (ACE2, SEQ ID NO:1), the variant of ACE2 having ACE2 activity and a molecular weight of less than about 70 kD.

Embodiment 2. The variant of ACE2 of embodiment 1, wherein the variant of ACE2 includes an N-terminal deletion, a C-terminal deletion, or both, relative to full-length ACE2 (SEQ ID NO:1), for example SEQ ID NO:3 or SEQ ID NO:4.

Embodiment 3. The variant of ACE2 of embodiment 2, wherein the deletion removes a glycosylation site present in full-length ACE2.

Embodiment 4. The variant of ACE2 of any of the foregoing embodiments, wherein the variant of ACE2 has a molecular weight of less than about 60 kD.

Embodiment 5. The variant of ACE2 of any of the foregoing embodiments, wherein the variant of ACE2 has higher ACE2 activity than full-length ACE2 (SEQ ID NO:1) for converting AngII(1-8) to Ang(1-7).

Embodiment 6. The variant of ACE2 of any of the foregoing embodiments, wherein the variant is a truncated form of ACE2 that has a half-live in plasma of at least of at least 6 hours, 12 hours, 1 day, 2 days, 3 days, 4 days, 5 days, 6 days, one week, two week, three weeks, four weeks, or longer.

Embodiment 7. A fusion protein comprising the variant of ACE2 of any of any of the foregoing embodiments, such as a truncated form, fused to a heterologous amino acid sequence that increases the half-life of the variant of ACE2 in plasma.

Embodiment 8. The fusion protein of embodiment 7, wherein the fusion protein has a half-live in plasma of at least of at least 6 hours, 12 hours, 1 day, 2 days, 3 days, 4 days, 5 days, 6 days, one week, two week, three weeks, four weeks, or longer.

Embodiment 9. The fusion protein of embodiment 7 or 8, wherein the heterologous amino acid sequence comprises an amino acid sequence selected from the group consisting of (i) an amino acid sequence of the Fc portion of an antibody or a fragment thereof, which preferably is devoid of its hinge region to prevent dimerization of the fusion polypeptide (e.g., SEQ ID NO:6, SEQ ID NO:7, or SEQ ID NO:8); (ii) an amino acid sequence of serum albumin or a fragment thereof, for example the amino acid sequence of domain III of human serum albumin or a fragment thereof (e.g., SEQ ID NO:9); and (iii) an amino acid sequence of streptococcal protein G or a fragment thereof such as the amino acid sequence of the C-terminal albumin binding domain 3 (ABD3) of streptococcal protein G (e.g., SEQ ID NO:5).

Embodiment 10. The fusion protein of any of embodiments 7-9 further comprising a linker amino acid sequence between the variant of ACE2 and the heterologous amino acid sequence (e.g., a linker sequence of 5-15 amino acids selected from glycine and serine).

Embodiment 11. The fusion protein of any of embodiments 7-10, further comprising an amino acid tag sequence such as an amino acid sequence comprising 5-10 histidine residues.

Embodiment 12. A conjugate comprising the variant of ACE2 of any of embodiments 1-6 (e.g., a truncated form of ACE2) or the fusion protein of any of embodiments 7-11, wherein the variant of ACE2 or the fusion protein is covalently attached to a polyethylene glycol polymer.

Embodiment 13. A conjugate comprising the variant of ACE2 of any of embodiments 1-6 or the fusion protein of any of embodiments 7-11, wherein the variant of ACE2 or the fusion protein is conjugated to a nanoparticle, such as a biogel, a polymer-coated nanobin, and gold nanoparticles.

Embodiment 14. The conjugate of claim 12 or 13, wherein the conjugate has a half-live in plasma of at least of at least 6 hours, 12 hours, 1 day, 2 days, 3 days, 4 days, 5 days, 6 days, one week, two week, three weeks, four weeks, or longer.

Embodiment 15. A pharmaceutical composition comprising: (i) any of the foregoing embodiments reciting variants of ACE2, fusion proteins, or conjugates thereof; and (ii) a suitable pharmaceutical carrier.

Embodiment 16. A method for reducing AngII(1-8) levels and/or increasing Ang(1-7) levels in a subject in need thereof, the method comprising administering to the subject the pharmaceutical composition of embodiment 15.

Embodiment 17. The method of embodiment 16, wherein the subject has a condition selected from the group consisting of diabetic and non-diabetic chronic kidney disease, acute renal failure and its prevention, chronic kidney disease, glomerulonephritis, severe hypertension, scleroderma and its skin, pulmonary, kidney and hypertensive complications, malignant hypertension, renovascular hypertension secondary to renal artery stenosis, idiopathic pulmonary fibrosis, liver fibrosis such as in liver cirrhosis patients, an aortic aneurysm, cardiac fibrosis and remodeling, left ventricular hypertrophy, and an acute stroke.

Embodiment 18. The method of embodiment 16 or 17, wherein the pharmaceutical composition is administered by intravenous administration, subcutaneous administration, or pulmonarily (e.g., via inhalation through an inhaler or nebulizer).

EXAMPLES

The following examples are illustrative and should not be interpreted to limit the scope of the claimed subject matter.

Example 1

Novel Active ACE2 Fragments

Introduction and Aims

Activation of the renin angiotensin system (RAS) plays a major role in the pathogenesis of diabetic kidney disease (DKD) and its progression to CKD. There are several conditions where the RAS is overactive either systemically or locally or both as in diabetic kidney disease systemic scleroderma, malignant hypertension, idiopathic pulmonary fibrosis, cardiac hypertrophy.Angiotensin Converting Enzyme 2 (ACE2) is a transmembrane monocarboxypeptidase that converts Angiotensin II (1-8) (AngII) to Angiotensin (1-7) (Ang (1-7)). Lowering AngII levels by ACE2 should prevent or attenuate the detrimental actions of excess of this peptide. In addition, Ang (1-7) formed as a result of AngII cleavage and working on its own receptor, has tissue protective functions that are generally opposite to those of AngII and thus complementary to lowering AngII. During the past funding period our lab was able to purify and produce mouse recombinant ACE2 (mrACE2) as a way to circumvent the immunogenicity of human ACE2 when given to mice. We examined the kidney effects of mrACE2 administrated systemically via daily injections mrACE2 or by DNA minicircle delivery. This resulted in a sustained and profound increase in plasma ACE2 activity that conferred enhanced ability to metabolize an acute AngII load. In mice with DKD induced by Streptozotocin (STZ) minicircle gene ACE2 delivery or rACE2 administration, however, failed to increase urinary ACE2 activity and there was no improvement in albuminuria, glomerular mesangial expansion, glomerular cellularity and glomerular hypertrophy. Thus, a profound augmentation of ACE2, confined to the circulation, failed to ameliorate the glomerular lesions and hyperfiltration characteristic of early STZ induced DKD. The reason why targeting the circulatory RAS with marked ACE2 amplification is not effective to ameliorate DKD is attributable to the fact that the systemic RAS is not overactive and blood pressure not increased in the STZ model (submitted for publication). By contrast, the therapeutic use of rACE2 to counteract RAS overactivity is supported by our preliminary data in a mouse renin transgenic model of systemic AngII excess where mouse rACE2 fused with an Fc tag to increase its duration of action lowered the elevated plasma AngII levels and markedly ameliorated albuminuria and hypertension (submitted for publication).

The large molecular size of ACE2 (~110 kDa) renders it non-filterable by a normal glomerulus or in early forms of DKD, which explains the lack of significant therapeutic benefit that we observed in the STZ model of DKD. That ACE inhibitors, are effective in this model and other models of DKD can be ascribed to the fact that these small molecules are easily filtered and thus capable of suppressing local kidney ACE and thus AngII formation. With marked increases in glomerular permeability, as seen in a col4A3−/− mouse model of Alport disease and CKD, we were able to show that infused rACE2 can be filtered as it is easily recovered in the urine. At this late stage, however, it is difficult to fully reverse kidney alterations and reverse fibrosis. We are therefore interested in engineering and testing new forms of recombinant ACE2 with reduced molecular size so that they can pass a normal or slightly compromised kidney glomerular filtration barrier. Our proposed design of a new ACE2 biologic stemmed from the observation of a specific ACE2 species that are naturally found in mouse and human urine. It is a shorter form of ACE2 at 75 kD that we found to be enzymatically more active than the intact 110 kDa protein. We have reduced the molecular size of ACE2 to facilitate kidney delivery via glomerular filtration with the main goal of treating kidney RAS overactivity in DKD. We have generated ACE2 truncates of lower molecular weight, 1-619 (71 kD), and 1-605 (69 kD), which are also active and suitable to kidney delivery via glomerular filtration. In addition, we seek to add a carrier tag to the shortest ACE2 protein that retains high enzymatic activity for extending its biological half-life to facilitate its chronic use. Enhancing the degradation of AngII using rACE2 offers the distinctive advantage of concurrent formation of Ang 1-7, a renoprotective peptide, and is a more natural physiologic approach than blocking the formation or action of AngII. Moreover, we postulate that ACE2, by continuously degrading AngII formation, when used in conjunction with ACE inhibitors, will effectively prevent the AngII escape, which attenuates the effectiveness of traditional RAS blockers. The aims of the work disclosed herein are: (1) To generate the shortest murine and human ACE2 protein fragment(s) that retains high enzymatic activity and are deliverable to the kidney via glomerular filtration, evaluate their effect on Angiotensin II degradation in vivo as well as their effect on blood pressure and purify and produce them in sufficient amounts for chronic use; This has been largely accomplished already for our short ace2 truncates referred as 1-619 and 1-605 (2) To evaluate the renoprotective effects of short rACE2 truncates in murine models of early DKD; and (3) To enhance the duration of action of the shortest ACE2 truncates using protein fusion technologies and examine their renoprotective action in murine models of DKD alone and in combination with an ACE inhibitor. Our overarching goal is to develop enzymatically active shorter ACE2 proteins with enhanced half-life that are effective to combat DKD in a way that is advantageous to existing RAS blockers. Moreover, these shorter ACE2 proteins will be tested for other conditions where the RAS is overactive such as systemic scleroderma, malignant hypertension, cardiac hypertrophy, and idiopathic pulmonary fibrosis among others.

Summary of Work to Date

Our work to date has focused on achieving ACE2 amplification as a way to increase Ang II degradation to treat kidney disease[3]. As a proof of concept a podocyte-specific transgenic mouse generated by our collaborator, Dr. Kevin Burns and his group was used to examine the effect of glomerular ACE2 over-expression on STZ induced DKD[4]. This podocyte-specific transgenic mouse had a modest increase, (2-5 fold), in ACE2 expression within the glomeruli. This relatively small increase in glomerulus-restricted ACE2 activity was nevertheless sufficient to confer significant renoprotection based on reduction of albuminuria and of mesangial expansion in the STZ model of DKD[4]. As a way to amplify endogenous ACE2 we performed studies using a small molecular compound (1-[(2-dimethylamino) ethylamine]-4-(hydroxyethyl)-7-[(4-methylphenyl) sulfonyl oxy]-9H-xanthene-9-one) (XNT) that was initially described to be an ACE2 activator. To our surprise, however, XNT exerted its effects on AngII induced hypertension in ACE2KO mice indicating that it works by a mechanism independent of ACE2[5]. Moreover, results from LC-MS/MS showed that XNT did not alter plasma Ang II, Ang (1-7) or Ang (1-5) levels, whereas rACE2, used as positive control, markedly increased Ang (1-7) and Ang (1-5) levels as a result of enhanced Ang II degradation[5].

Because we could not use XNT or DIZE, another presumed ACE2 activator, for the purpose of robust and clear cut ACE2 amplification, and the toxic nature of these compounds, we developed our own mouse recombinant ACE2[6,7]. In ex-vivo studies, we examined the actions of our mouse (mrACE2) on angiotensin peptides dynamics in the physiological environment of plasma using LC-MS/MS for concurrent measurements of 10 angiotensin peptides[7,8]. We then administered mouse rACE2 to control and diabetic mice acutely and chronically, via daily i.p injections or by ACE2 delivery using mini-circles technology[9,10]. Minicircle DNA delivery, unlike lentiviral delivery, is resistant to gene silencing, and therefore represents an attractive platform for gene replacement strategies in vivo. The cDNA of intact mouse ACE2 was cloned into a circular expression cassette and the resulting ACE2 minicircle was injected to FVB mice using i.v hydrodynamic approach[10]. Mice that received ACE2 by minicircle were followed for several weeks for monitoring blood pressure, serum ACE2 activity and plasma Ang II levels. After several months of follow up, Ang II was infused acutely. The increase in plasma Ang II in mice treated with ACE2 was significantly reduced as compared to vehicle treated mice. We next induced diabetes with STZ in mice pretreated with ACE2 via minicircle delivery. Despite the expected increase in serum ACE2 activity that was sustained for 26 weeks of follow up, there was no detectable increase in urinary and kidney ACE2 activity and the development of albuminuria and the glomerular lesions induced by STZ was not prevented.

To further examine whether urinary ACE2 activity is of circulatory or renal origin we infused murine rACE2 to control, db/db mice and Col4A3−/− mice, a model of Alport syndrome with associated CKD[10,11]. When db/m and db/db mice were infused with intact rACE2, a marked increase in serum ACE2 activity was observed but there was no increase whatsoever of urinary ACE2 activity[10]. Accordingly, we concluded that increasing ACE2 levels in plasma is not sufficient to improve DKD in the STZ or db/db models with minimal albuminuria[10] due to lack of delivery to the kidney of administered intact rACE2. It should be noted that in the STZ and other rodent models of DKD and in human DKD the RAS is overactive locally in the kidney but not in the circulation, the so-called renin paradox. Indeed, plasma renin activity levels, and by extrapolation Ang II levels, are often reduced in patients with diabetes and DKD[12-16].

Therefore, unless ACE2 can be increased at the kidney level, amplification of ACE2 in plasma alone has a limited therapeutic role unless when AngII levels are increased in plasma. We therefore have been working at the design of a new strategy for ACE2 amplification within the kidney.

Significance

The renin-angiotensin system (RAS) has been widely implicated in the pathogenesis of DKD. Circulating AngII and particularly locally produced AngII can mediate kidney disease through a series of hemodynamic and non-hemodynamic effects[16-23,24-26]. The relative effectiveness of ACE inhibitors and other RAS blockers in retarding the progression of kidney disease and reducing proteinuria in patients with DKD is further evidence of RAS over-activity playing a role in the development and progression of DKD. Activation of the RAS locally within the kidney by glucose, including AngII production, has been well documented at the cellular level in cultured podocytes and tubular cells[24-26]. Additional direct evidence comes from findings of increased RAS components in the kidney and urines from rodent models of DKD and in urine bio samples from patients with DKD[22,23,27-31]. Currently used RAS blockers provide significant but incomplete protection and variable response rates[32-35]. There is therefore a need for new approaches to counteract RAS over-activity that expand and improve on the existing approaches based on blockade of Ang II formation or action. The dissipation of AngII involves several pathways (FIG. 1). Of particular interest is the one driven by enzymes such as ACE2 that lead to the formation of Ang (1-7)[36-43]. Although there are other enzymes such as PRCP and PEP that can also form Ang (1-7) from Ang II it is generally believed that ACE2 degrades AngII to Ang (1-7) with the highest efficiency[6,36,37,42,43]. Thus, the dual effect of ACE2 lowering of AngII and increasing Ang (1-7) could be extremely effective therapeutically and would replicate the natural pathway of disposing of excess AngII.

Human intact rACE2 appears safe in the human setting as it has already successfully passed a phase 1 clinical trial[44] and there are ongoing clinical trials examining the possible benefit of hrACE2 for lung injury in a multi-center phase II trial in the U.S. and Canada. This form of rACE2, because of its large size and relatively brief half-life, however, is not suitable for the long-term treatment of a chronic disease such as DKD. Moreover in DKD circulating RAS is usually not overactive[13,15]. We have developed and propose the further development of mouse and human forms of ACE2 of lower molecular size to permit delivery to the kidney via glomerular filtration and with enhanced organ tissue penetration and markedly enhanced half-life Distinctive features of rACE2 administration that can be advantageous over RAS blockers include the continuous dissipation of AngII when the levels are increased in the circulation and/or locally within the kidney. Of note, after initiation of therapy with ACE inhibitors, plasma AngII levels return to normal or even increase above normal despite sustained and marked ACE suppression. This is referred to as the ACE or Ang II escape phenomena[45-64]. With ARB blockers the levels of AngII increase reactively from the start of this therapy as a result of blockade of the AT1 receptor and remain elevated[65]. A distinctive feature of rACE2 administration is that, concurrent to the lowering of AngII levels, Ang (1-7) is formed which is an organ protective peptide[66-70]. We postulate that therapies based on ACE2 administration are more physiological and possibly more effective than existing RAS blockers as the increase in AngII levels should be totally prevented owing to continuous AngII degradation. A short rACE2 could be used alone or in combination with either ACE inhibitors or ARBs. A new rACE2 biologic directed to down-regulating the kidney RAS pathway that is overactive in DKD, CKD, lung fibrosis and other conditions listed above could be rapidly tested for clinical use and should constitute a therapeutic "tour de force".

Innovation

Intact ACE2 has a relatively large size of 100-110 kDa and according to our experimental work and theoretical considerations precludes its delivery to the kidney by passage via glomerular filtration. We have shown that this is a key limitation of the intact ACE2 for its potential use to treat STZ-induced DKD early on when glomerular permeability is not severely altered[10]. Here, we propose to develop and test shorter forms of ACE2 that are deliverable to the kidney by glomerular filtration, and therefore can access the tubular lumen for direct control of local RAS over-activity. There is a rich RAS in the apical border of the proximal distal and collecting tubule of the kidney that mediates many of the renal actions Ang II[71-78]. Glomerular filtration of compounds involves several barriers: firstly the endothelial layer, the glomerular basement membrane, and lastly the podocyte foot processes[79]. In recent studies the role of the proximal tubule in the quantitative contribution to albuminuria has been reexamined[80]. It has been shown that the filtration of albumin was greater than previously believed which determines an increased role of the proximal tubule in reducing albuminuria by its re-absorption[80-85]. Clearly, albumin with a molecular weight of 66-kD (585 amino acids) and despite being negatively charged, gets filtered to some extent under physiologic conditions and much more with even moderate alterations in glomerular permeability[80-83].

By extrapolation, short ACE2 truncates with a molecular weight≤70 KDa should be filterable as well. In accord with this postulate we now provide data that two recently generated short ACE2 proteins with a size of 69-71 kDa (two prototype constructs that have been already sequenced, generated and purified) are filterable in mice with ACE2 genetic deficiency and in the STZ-model of early DKD. We are extending their half-life in plasma by creating fusion protein comprising their amino acid sequence fused to an amino acid sequence of a heterologous protein that increases the half-life of the fusion protein in plasma. The amino acid sequence of the heterologous protein is utilized to promote in vivo stability of short ACE2 amino acid sequence, particularly in avoiding protein catabolism by renal tubular cells[86-91]. The designs of the fusion proteins are based on the principle that renal tubular reabsorption follows two distinct pathways through separate receptors activities. Those proteins having affinities for megalin and cubilin typically are directed to lysosomal degradation[92-95]. By contrast, certain plasma proteins, such as albumin and immunoglobulins, are largely spared from renal catabolism due to their natural affinities to alternative receptors for recycling, known as FcRn[79,93,96-100]. These receptors are abundantly expressed on the apical surface of renal tubular epithelium, podocytes and endothelial cells[79]. By creating fusion proteins having high affinity tags for FcRn fused to ACE2 truncates, the half-life of the ACE2 truncates can be increased. The fusion tags are intended to increase tissue penetration/tissue uptake and promote in vivo stability and therefore extend its half-life such that it is suitable for weekly or possibly biweekly administration subcutaneously by the patient much in the same way as people with anemia inject themselves on a weekly or biweekly schedule. In addition to the kidney, targeting of the lungs as the portal for delivery by inhalation of our short ACE2 could be accomplished after Fc fusions. Indeed, it is known that Fc tagged proteins are of interest for this purpose owing to the expression of FcRn in the epithelium of the lungs[148]. For instance, delivery that exploits an active carrier system, the FcRn pathway, through the epithelial barrier in the lung of a large protein, such as EPO, fused with Fc has been reported[149].

Figure 8:
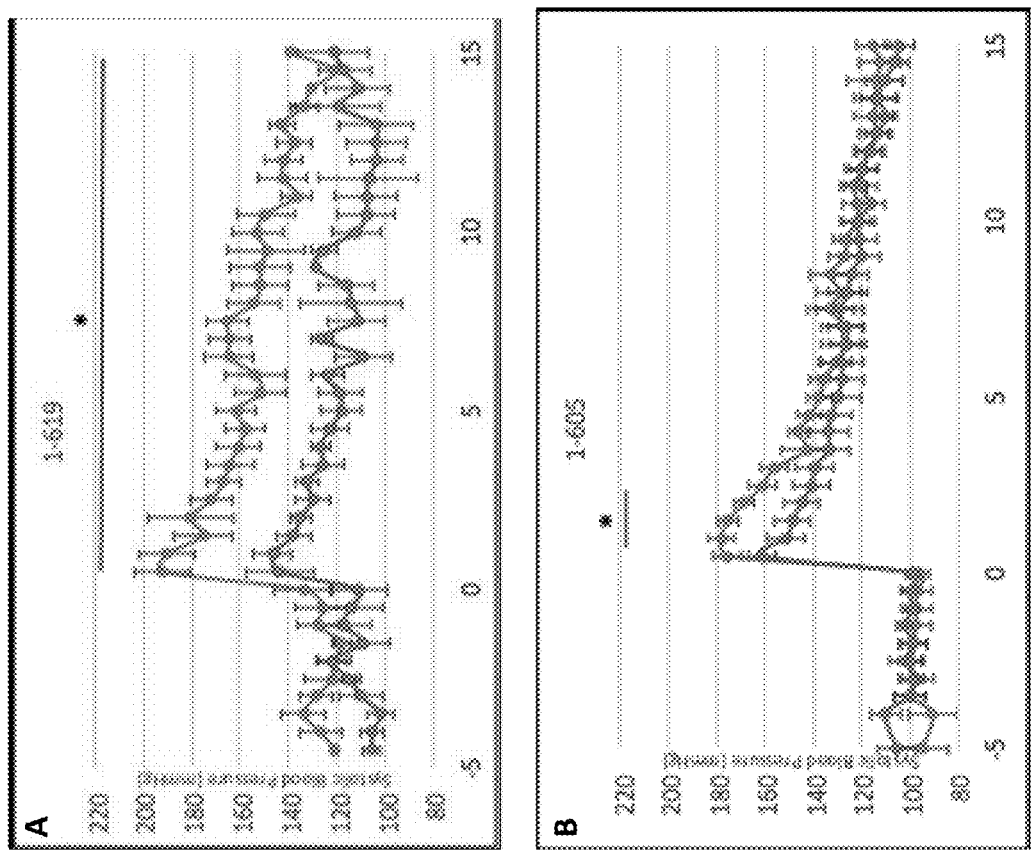
FIG. 8. Infusion of short rACE2[2] 1-619 (A) or 1-605[2] (B) causes a faster recovery from Ang II-induced hypertension as compared to respective animals non-infused with rACE2 (blue). X-axis indicates time (min.) from Ang II bolus (0.2 µg/g BW). *reflects a significant difference (see text in Examples section).

The presence of abundant RAS components and their receptors in the kidney proximal tubule and over-activity of this system in general is known to contribute to the development of DKD and progression to CKD[17]. The proposed targeted approach to the kidney RAS, however, does not mean that other extra-renal tissues and the circulation at large will not benefit from the administration of a short ACE2. In situations where Ang II is elevated in plasma, short ACE2 will help dissipate it and form Ang 1-7 and lower blood pressure. Our preliminary work with the intact ACE2 coupled to Fc demonstrates an impressive increase in duration of action, to at least 7 days, as demonstrated by persistence of its lowering blood pressure effect after acute Ang II induced hypertension (submitted for publication). But in situations when the blood pressure and plasma Ang II are not increased, it can be an advantage for safety reasons that increasing ACE2 does not lower blood pressure or only minimally lowers blood pressure. A "biobetter" form of a biologic involves taking the originator molecule and improving its therapeutic properties by making specific alterations in it to improve its parameters to make it more efficacious, less frequently dosed, and/or better tolerated[87]. In summary, we propose to construct short forms of rACE2 with access to the kidney via glomerular filtration, and having an extended in vivo half-life, as a way to increase Ang II to Ang (1-7) conversion within the kidney. This would be the first time, to our knowledge, that a large molecule is administered for direct targeting of the RAS to treat DKD. This novel bioloinc should be effective in advanced DKD but also early on in the course of DKD when only moderate alterations in glomerular permeability are present and when the RAS is overactive at the kidney level but not in the circulation, a situation that occurs often in most rodent models and in human DKD[23-25, 27-30, 101]. As noted earlier the short ACE2 truncates will be expected to be effective in treating conditions including diabetic and non-diabetic chronic kidney disease, acute renal failure and its prevention, chronic kidney disease, glomerulonephritis, severe hypertension, scleroderma and its skin, pulmonary, kidney and hypertensive complications, malignant hypertension, renovascular hypertension secondary to renal artery stenosis, idiopathic pulmonary fibrosis, liver fibrosis such as in liver cirrhosis patients, an aortic aneurysm, cardiac fibrosis and remodeling, left ventricular hypertrophy, and an acute stroke Approach Aim 1. To Generate the Shortest Murine and Human ACE2 Protein Fragment(s) that Retain High Enzymatic Activity and are Deliverable to the Kidney via Glomerular Filtration, Evaluate their Effect on Angiotensin II Degradation and Purify and Produce them in Relatively Large Amounts for Chronic Use.

Background and preliminary data: We have shown that intact mrACE2 given to mice degrades exogenous Ang II effectively and forms Ang (1-7) and is not immunogenic when given to mice for months. We also found that in diabetic mice (db/db and STZ-treated mice) urine ACE2 is increased[9]. To examine whether the increase in urinary ACE2 activity could be, in part, of circulatory origin we infused intact rACE2 (1-740 AA) to control and diabetic mice[9]. Despite a marked increase in circulating (serum) ACE2 activity there was no increase in urinary ACE2 activity. We and others therefore concluded that the source of urine ACE2 is of renal origin likely originating from shedding from the proximal tubule apical membrane[9108]. A major function of the glomerular capillary wall is to selectively restrict the trans-glomerular passage of albumin and other plasma proteins while filtration is occurring.[102]. Proteins and peptides smaller than approximately 70 kDa are more likely to be filtered than are larger proteins[103, 104]. Generally, proteins with an overall negative change are less likely to be filtered than neutral polypeptides because of repulsion by the negatively charged basement membrane of the kidney[105-107]. As noted above, infusions of intact ACE2 to normal mice and mice with STZ induced DKD failed to increase urine ACE2 activity since this is a large protein (>100 kDa) that normally cannot be filtered[10]. In Col4A3−/− mice, a model of Alport syndrome with a large glomerular permeability defect, urinary ACE2 activity increased markedly[10]. Below, we demonstrate the generation of short forms of ACE2 that can be delivered to the kidney via glomerular filtration in mice with mild elevations in AER as typically seen in the STZ and other models of DKD in rodents[7].

Our quest towards this overall goal started with the identification of two urinary ACE2-immunoreactive bands by Western blot that are ACE2-specific since they are not present in ACE2 deficient mice[9]. One band at about 110 kD corresponds to the molecular weight of intact ACE2 and likely is a shedding product from the kidney apical tubular membrane where ACE2 is abundantly expressed[9, 71, 72]. The presence in the urine of a band at 75 kD, suggested that this band is a degradation product of the 110 kDa ACE2 band (FIG. 2). Consistent with this notion when freshly isolated whole kidney lysates, in which only the 110 kDa band was detectable, were incubated for 24 hr at 37 C, a 75 kDa band appeared while the ACE2 110 kD band gradually decreased (FIG. 2).

Ultrafiltration experiments to separate the two naturally occurring bands in the urine further revealed that the level of ACE2 activity of the 75 kDa band is higher than that of the 110 kD band after correction for protein abundance (FIG. 3). We next extended incubation time of intact rACE2 in ACE2KO kidney lysates (as a way to exclude any effects from the kidney's own ACE2) and this resulted not only in the formation of a 75 kD band but also of a shorter ~60 kD ACE2 band that had significant ACE2 activity (FIG. 4). From these findings, we concluded that intact rACE2 can be shortened to a ~60 kDa fragment that retains or has an even higher specific enzymatic activity than the original 100-110 kDa intact rACE2 protein (FIG. 4). This process must be mediated by proteases that are capable of shortening ACE2 to shorter and yet enzymatically active fragments.

Using the approach described under proposed work, we already have generated and tested various versions of ACE2 deletion mutants, notably ACE2 C-terminal deletion mutants referred to as "1-619" and "1-605", that are active whereas a shorter "1-522" ACE2 deletion mutant lacks activity. ACE2 1-605 has a theoretical molecular weight of 69 kDa (by Expasy Bioinformatics) and about the same enzymatic activity as intact ACE2 (106±5% of the intact rACE2) whereas 1-619 is even more active than intact ACE2 (1-740 AA) (144±7% $p<0.01$). We have been able to produce and highly purify small amounts of these two truncates (1-619 and 1-605) for acute infusion (FIG. 5A). The i.v. infusion of 1-619 and 1-605 resulted in significant increases in urine ACE2 activity in mice with genetic ACE2 deficiency. In these ACE2-deficient animals, after the infusion of 1-605, there was a marked increase in plasma ACE2 activity (906±94 RFU/ul/hr). Western blots of urines from ACE2KO infused with A619 revealed an ACE2-immunoreactive band of ~70 kD (FIG. 5B).

Additional studies were done in an ACE2 KO mice made diabetic with STZ and studied 12-15 weeks later. Both ACE2 truncates were infused to further demonstrate that activity can be recovered in the urine of this model as well. Either truncate resulted in a clear increase in urine ACE2 activity (FIG. 6A). Like in the previous experiments, the activity found with 1-619 was higher than that observed with 1-605 but the difference did not achieve statistical significance possibly because the small number of observations. In WT mice made diabetic with STZ, urine ACE2 was already substantial (compare scales in FIG. 6B with 6A). The presence of ACE2 is the result of tubular shedding[9,108]. Because of the presence of endogenous ACE2 we used a higher dose of A1-619 (4 μg/g BW) and demonstrated an increase beyond that normally present in the urine (FIG. 6B).

To demonstrate further that the new ACE2 truncates are amenable to glomerular filtration and kidney uptake, whereas the intact ACE2 is not, we used advanced radionuclide imaging. As shown in FIG. 7, at 1 hr after i.v infusion there is a nephrogram with marked uptake in the cortical areas of both kidneys after infusion with A619 but not after infusion of the same dose of intact rACE2.

In terms of activity, we also evaluated the ability of ACE2 (1-605) to metabolize Ang II by infusing ACE2 (1-605) together with an Ang II bolus, which resulted in a rapid surge of this peptide. At 5 min post infusion the level of Ang II was markedly lower in 1-605 infused mice than in non-infused mice (104±33 vs 399±45 fmol/mL $p=0.007$). This Ang II-lowering effect is similar to the Ang II-lowering effect shown previously by us using intact ACE2[6,7,10]. In separate experiments, we evaluated blood pressure recovery as a marker of in vivo ACE2 activity after infusing ACE2 truncates together with an Ang II bolus. As shown in FIG. 8, the administration of the two ACE2 truncates enhanced the initial recovery from Ang II-induced hypertension. The effect of 1-619 on BP recovery appears more sustained than that of 1-605 (compare A to B) but both truncates had a significant effect (p value<0.02 and <0.04 respectively). In summary, our novel ACE2 truncates are active in vivo in terms of lowering infused Ang II and enhancing blood pressure recovery following administration of a bolus of Ang II. In addition, the ACE2 truncates are small enough that they can be delivered to the kidney via glomerular filtration.

Figure 4:
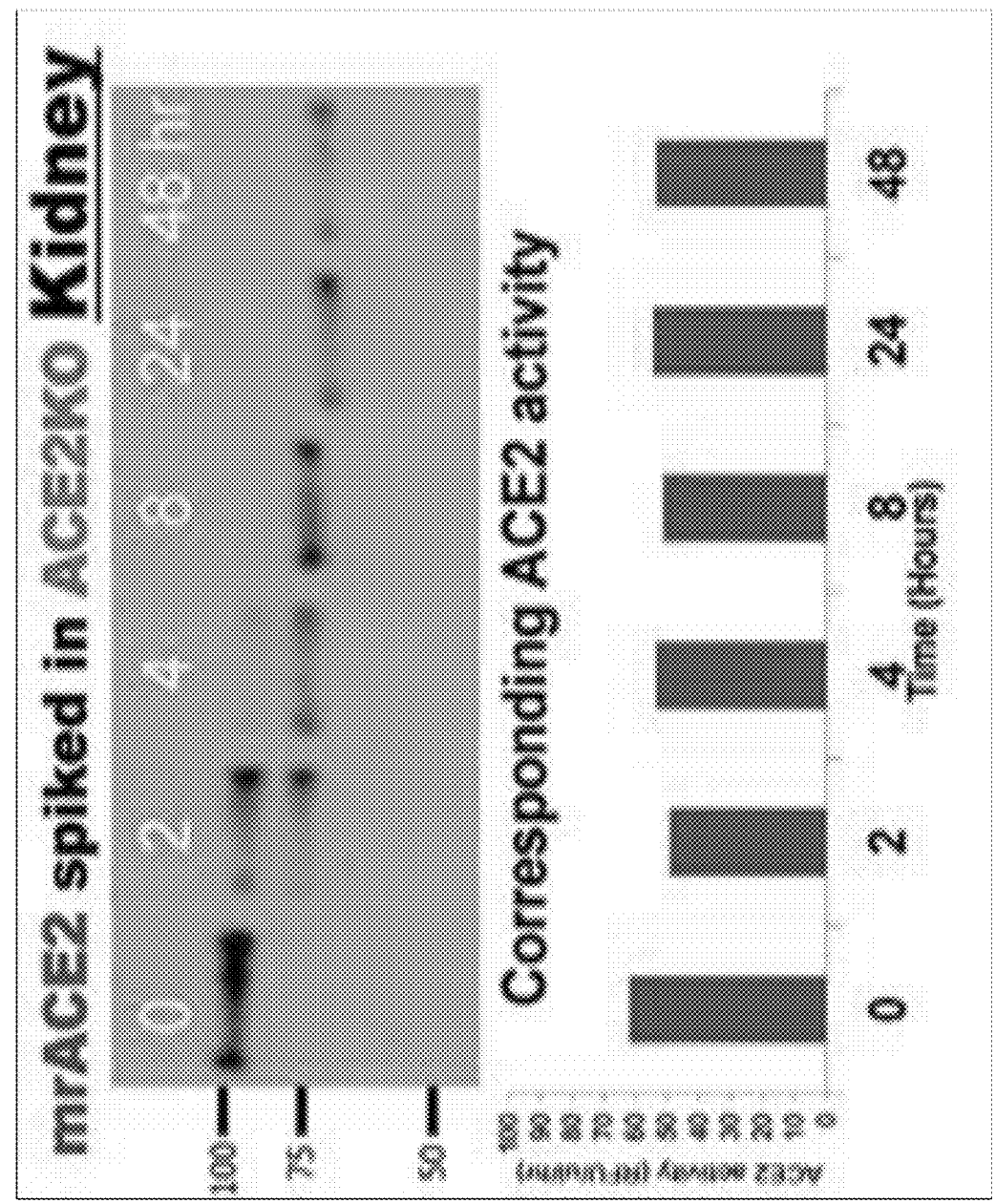
FIG. 4. Mouse recombinant[1] intact ACE2 (100-110 kD) was spiked into ACEKO kidney cortex lysate (10 nM mrACE2/~1 mg total protein of the lysate) from one ACE2KO mouse and incubated at 37 C for 48 hrs. Spiked mrACE2 samples at all incubation times were subsequently probed in Western blot. Western blot (WB) image shows disappearance of the spiked 100-110 kD mrACE2 band and first the appearance of smaller 75 kD ACE2 immunoreactive band and then ~60 kD band. In the lower panel, absolute ACE2 activity (not corrected for integrated density of the bands detected) is depicted showing similar enzyme activities of the 75 and ~60 kD bands versus the original 110 kD mrACE2 band despite weaker relative protein abundance (weaker bands at 75 kD and ~60 kD than the original 100-110 kD at 0 hr).
Figure 5:
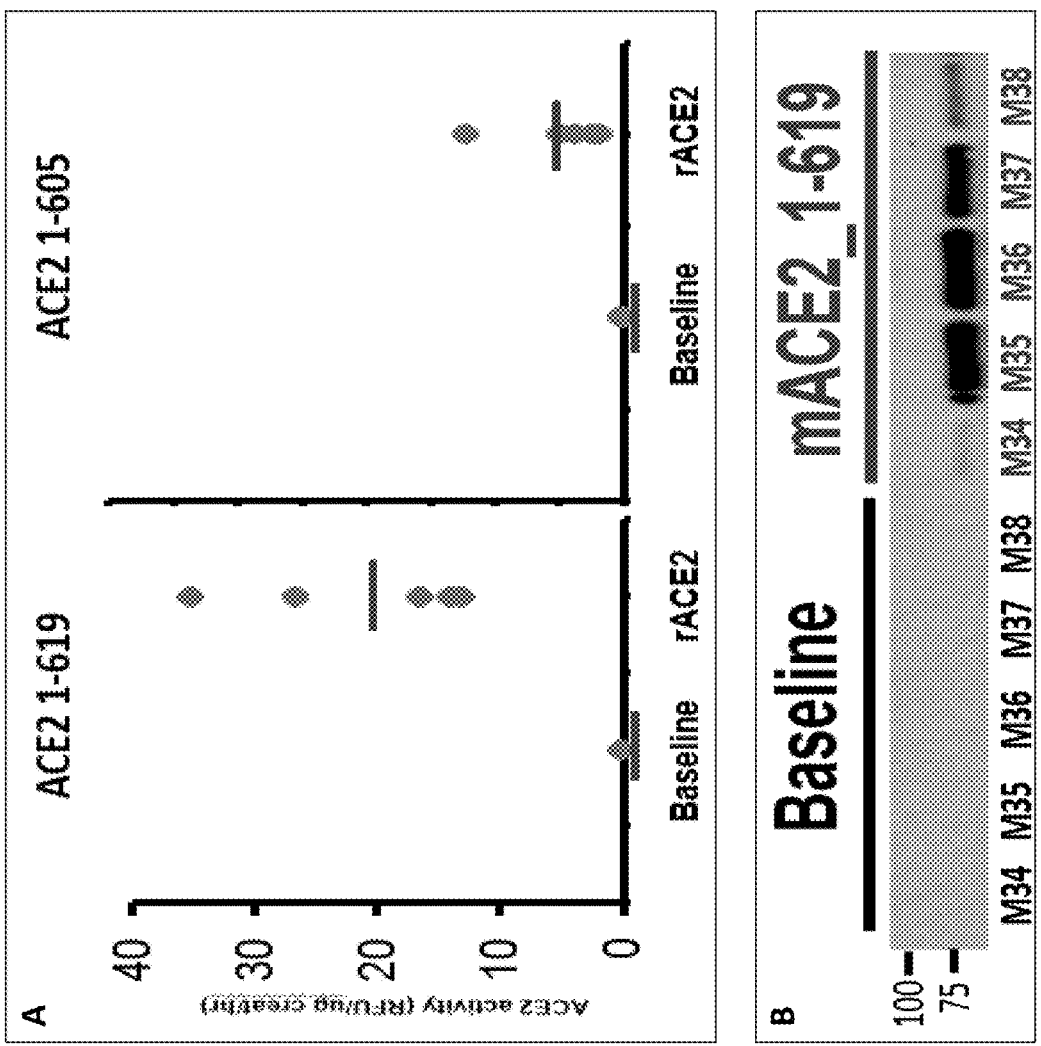
FIG. 5. Urinary ACE2 activity (A) and Western blot (B) in ACE2/PRCP dKO mice. (A) Urine ACE2 activity was not different from 0 at the baseline and increased significantly after i.v. ACE2 1-619 infusion (from −0.4±0.2 to 21.1±4.3 RFU/µg creat/hr (n=5, p<0.01). The infusion of the 1-605 truncate also resulted in a clear increase in urine ACE2 activity (from −0.1±0.2 to 5.1±1.9 RFU/µg creat/hr n=5 p<0.01). The level of ACE2 activity achieved by the 1-619 truncate was higher than that achieved with the 1-605 truncate (21.1±4.3 vs. 5.1±1.9 RFU/µg creat/hr, p<0.01, respectively). (B) WB of urines (36 ul/well) collected before (Baseline) and after i.v. bolus of ACE2 1-619 truncate (0-2 hrs) to five ACE2/PRCP dKO mice (mouse IDs M34-M38). It shows presence of an ACE2-immunoreactive band at the expected size of ~70 kD consistent with molecular size of the truncated ACE2 after but not before the infusion.
Figure 6:
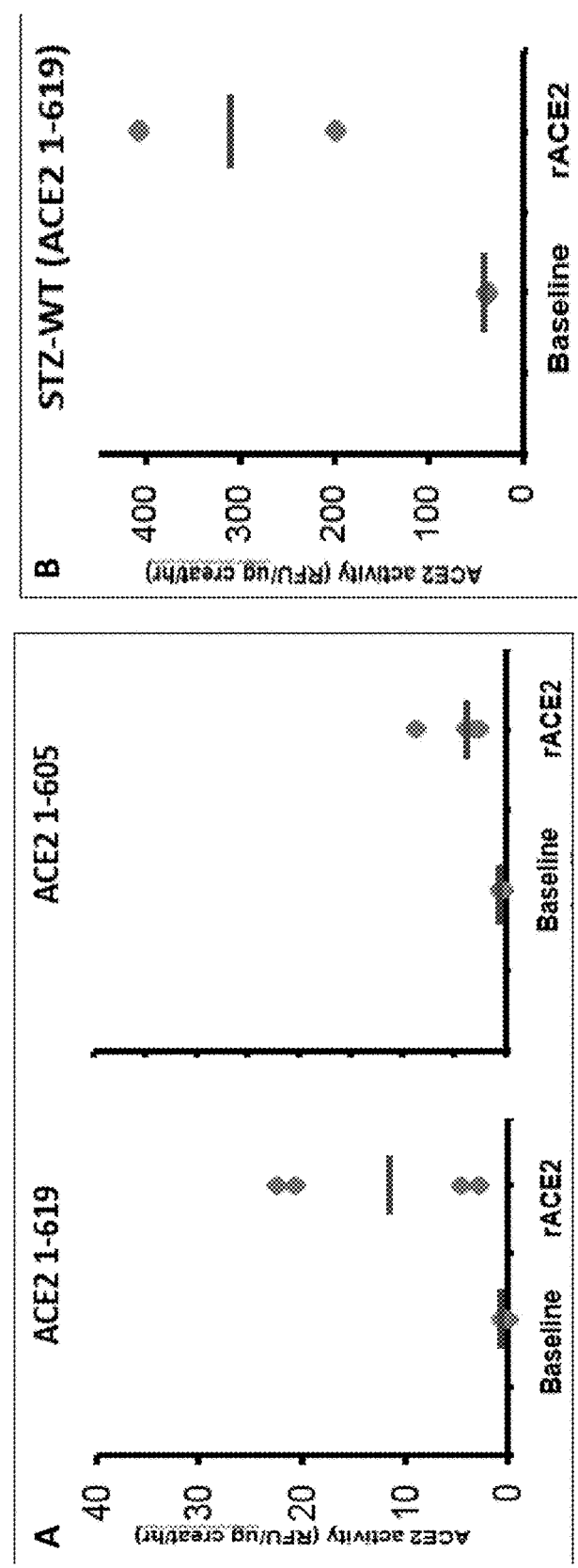
FIG. 6. Urinary ACE2 activity in STZ-treated ACE2KO mice. (A) In these studies, urine ACE2 after infusion of ACE2 1-619 (2 µg/g BW) increased from 0.3±0.1 to 12.6±5.2 RFU/µg creat/hr, p<0.05). Infusion of ACE2 1-605 (2 µg/g BW) increased urine ACE2 activity (from 0.1±0.2 to 4.5±1.4 RFU/µg creat/hr, p<0.05). As in the experiments in FIG. 5, the level of activity achieved with ACE2 1-605 was lower than with ACE2 1-619 but this difference did not reach statistical significance. (B) In two WT mice with STZ induced diabetes, where endogenous ACE2 urine activity was already substantial, the infusion of ACE2 1-619 (4 µg/g BW) also resulted in a marked increase in urinary ACE2 activity.
Figure 7:
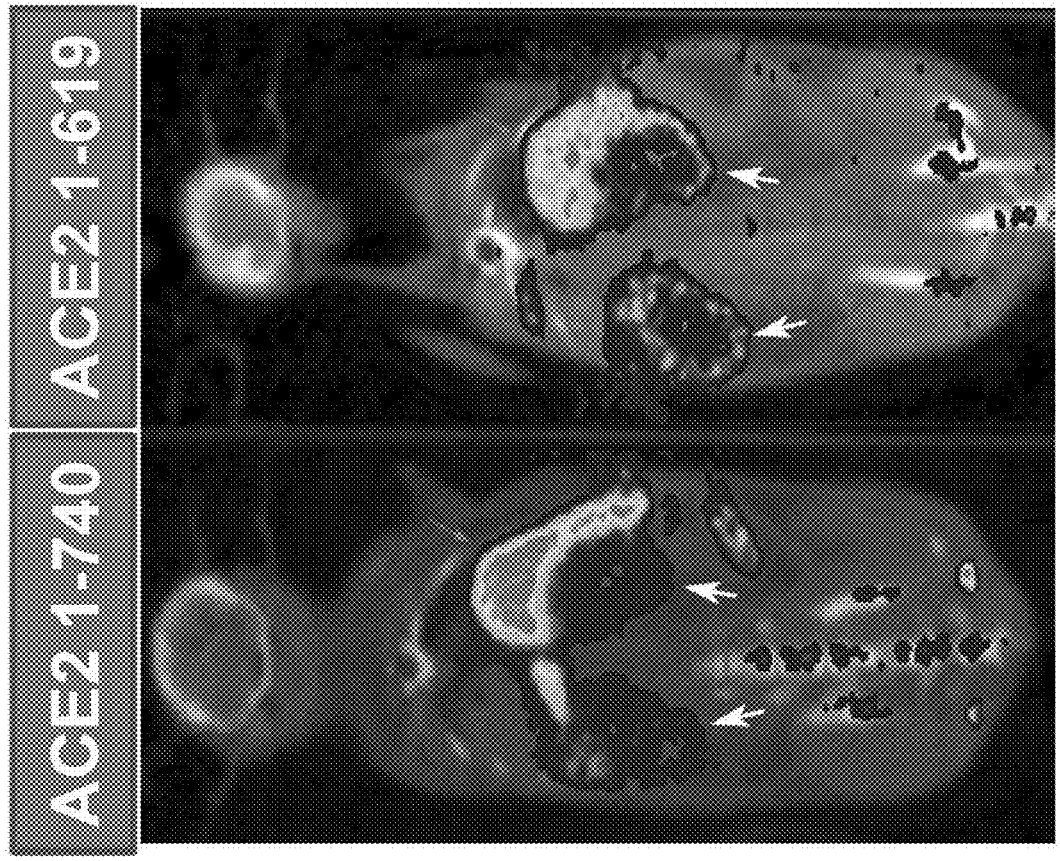
FIG. 7. In vivo images of kidneys. microSPECT (color) is overlaid on microCT (greyscale) in mice injected with $^{99m}$Tc labeled purified intact ACE2 1-740 (left) or ACE2 1-619 (right). It illustrates kidney uptake of the ACE2 1-619 and not the ACE2 1-740. The short ACE2 1-619 mainly concentrated in the renal cortex (white arrows) (compare right vs. left). Both ACE2 forms show strong liver presence (red arrows).

Proposed work. Our main objective is to construct short ACE2 fragments having a high level of ACE2 activity that can be used for therapeutic purposes. In its full-length form, ACE2 protein is an 805 amino-acid (AA) type-I transmembrane protein (110-120 kDa) that contains an extracellular[109] domain (AA 1-739), a transmembrane region (AA 740-768), and an intracellular tail (769-805)[110, 111]. The extracellular part of intact ACE2 (1-740 AA) contains the catalytic domain. To replicate the size of active short ACE2 protein obtained by proteolytic digestion we will generate a series of ACE2 deletion mutants of varying length through truncation of the C-termini and N-termini. These mutants will be expressed by HEK293 cells into the culture medium and ACE2 activities will be measured using a colorimetric substrate Mca-APK-Dpn[7]. The intact rACE2 that contains the full extracellular domain (1-740 AA) will be the positive control. We will produce short ACE2 variants and anticipate that through truncation of the C-termini and N-termini, we can reduce the size of ACE2 and identify truncates smaller than 1-619 and 1-605 that retain enzymatic activity. The goal of the procedure is to determine the boundaries of the shortest ACE2 fragments that still retain enzymatic activity. Our results from the kidney lysate study suggest that a truncated form of rACE2 at ~60 kDa is still active (FIG. 4). The cDNA of short ace2 will be generated by PCR amplification using as a template the cDNA of our intact soluble mouse ACE2 (740AA). To gradually shorten ACE2 (10 AA at a time, FIG. 9), we will use specific primers that determine the length of the shorter ace2 cDNA to be amplified and are compatible with an expression vector (i.e. pcDNA3.1). The sequence of amplified cDNA will be verified by sequencing to ensure absence of mutations.

Figure 9:
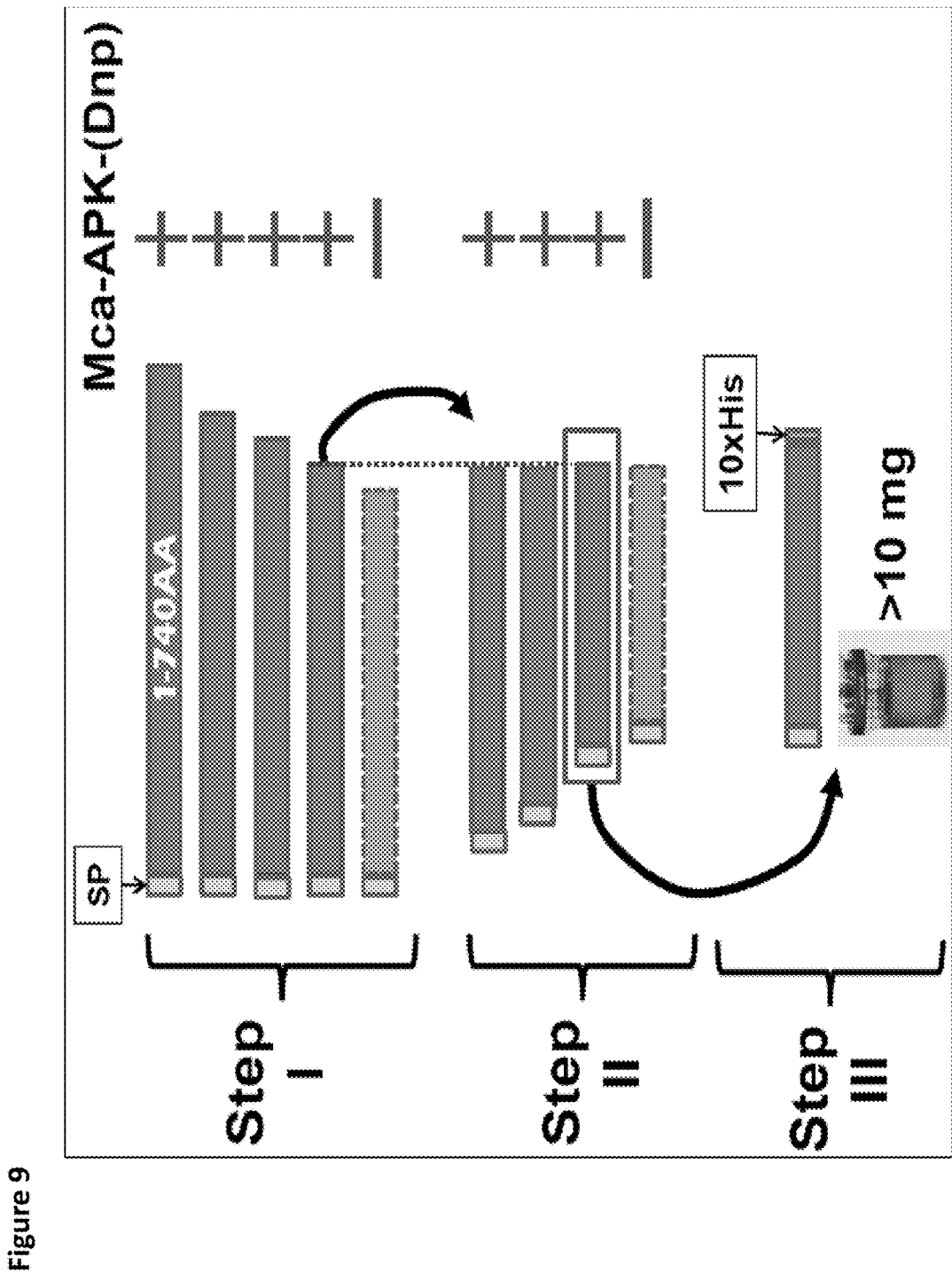
FIG. 9. Three steps for establishing the shortest enzymatically active form of ACE2. Enzymatically active (red filling) extracellular domain of intact ACE2 is 740 AA long (1-740). It contains a signal peptide (SP) that mediates extracellular secretion. Step I involves shortening ACE2 from C-terminus. For now, an ACE2 1-605 is the shortest active fragment we have produced, but we expect to proceed to shorten ACE2 1-605 from the C-terminus until no ACE2 activity (Mca-APK-Dnp-negative) is found. Step II will involve shortening the shortest C-terminally truncated ACE2 from the N-terminus (10AA at a time). SP (AA1-18) will always be attached to the N-terminally shortened ACE2. Step III: Once the C- and N-terminal boundaries of enzyme activity of ACE2 are found, the from both ends truncated ACE2 will be engineered to express C-terminal 10× His tag to facilitate purification from medium scale production (~10 mg) using a bioreactor.

We have completed the first series of deletion of the C-terminus and identified the boundary of an active enzyme (FIG. 9). The shortest construct of the series that still retains activity will be used as the starting template for the second series that focuses on the N-terminus. Here we note that the N-terminus ACE2 has a signal peptide (SP) sequence (aa 1-18) for the secretion of ACE2 during which the enzyme is also glycosylated so that it will adapt natural folding important for catalytic activities. Therefore, the N-terminal SP segment will be retained in the second series of deletion at the N-terminal end. To do that, a new NotI restriction enzyme site will be introduced after the SP sequence by site-directed mutagenesis, and primers for subsequent deletions of the N-terminus will all carry a NotI-compatible "overhang" to facilitate cloning of the intended constructs (FIG. 9). In our preliminary work, we have used a transgene transfection system mediated by pcDNA vectors to express ACE2 fragments, which all carry SP for excretion, from HEK293 cells. ACE2 activities will be measured directly from culture medium. In addition, western blot using a polyclonal antibody raised against the entire extracellular domain of ACE2 detects the transgenes and confirms molecular size.

To verify enzymatic activity of the overexpressed shorter ACE2 proteins, we will test their ability to cleave a) the synthetic fluorogenic ACE2 substrate, Mca-APK-(Dnp)[7] and b) its main natural substrate, Ang II(1-8) to form Ang (1-7) (measured by their respective ELISAs[7]). The relative enzymatic potency of the short rACE2 fragments will be determined by comparison with equivalent picomolar amounts of the intact rACE2 (740 AA long), which will be used as the benchmark. The short ACE2 fragments will be engineered to express a C-terminal poly-His tag by using a 10-His tag that we have constructed by ourselves. The His tag will allow quick and efficient purification of the ACE2 fragments using affinity purification on $Ni^{2+}$ sepharose followed by size exclusion chromatography on Superdex 300, as we have done previously[7]. The short ACE2 fragments will be stably expressed in mammalian cell lines (HEK293) in which we have already over-expressed several recombinant proteins. Using this approach, within weeks to months we were able to produce and purify sufficient amounts of two truncates (1-619 and 1-605) (~10 mg) to be able to perform in vivo studies in mice described above.

Kidney delivery by glomerular filtration of the shorter truncates will be demonstrated by acute infusions for measurements of urine ACE2 activity and by radiochemistry studies as described under preliminary data for 1-619. Knowing the sequence of the new active murine "short ACE2", we will next generate the corresponding human short ACE2 protein.

For human short ACE2 protein generation, we already have a full-length human intact ACE2 cDNA. Protein will be recombinantly expressed and purified as we have previously done with murine intact 110 kDa rACE2[7]. The enzymatic activity of the short form(s) of human ACE2 will be tested in vitro and in vivo as follows: ACE2 activities of the overexpressed human ACE2 truncates will be measured directly from culture medium (using both Mca-APK-(Dnp) substrate[7] and Ang II(1-8)[7]). Western blot analysis will be used to verify their molecular size. The ability of short ACE2 to cleave other known ACE2 substrates like apelin 13 will also be tested in vitro and in plasma as well as kidney lysates using assays routinely performed in our lab[112]. To examine in vivo Ang II degradation and the effect on Ang II-induced hypertension, short rACE2 (1 µg/g BW) will be given to mice before an Ang II bolus (0.2 µg/g BW), using a protocol previously described by us[6,7]. The relative potency of the short hrACE2 truncates will be determined by comparison with an equivalent of the intact hrACE2 (740 AA) as the standard.

Expected findings: The crystal structure of ACE2 suggests that the catalytic core of the enzyme spans between AA residues 147-555[110, 111], so it is conceivable that the minimum length requirement for enzymatic activity at least includes 147-555 AA. The 619 truncate is very active, even more than the intact ACE2. The shortest ACE2 protein that we have generated so far is 605 AA long and is enzymatically as active as the intact ACE2. (See data discussed above). Therefore the molecular size of these short ACE2 truncates: 1-619 (71 kD) and 1-605 (69 kD) is already low enough to examine their renoprotective potential. Both ACE2 truncates are amenable to glomerular filtration (FIG. 5a,6a,6b,7) and are active in vivo (FIG. 8) and therefore will be used in the studies described in Aim 2 below. However, even small molecular weight ACE2 truncates are preferred for fusing with a tag aimed at increasing the half-life of the ACE2 truncates, so that the fusion protein has a molecular size small enough for glomerular filtration. This is relevant for the proposed work under Aim 3. Although the primary goal to shorten ACE2 is for permitting glomerular filtration, it is known from proteases and peptidases participating in other systems, such as the blood coagulation enzymes, that the "extra length" in their sequences needs to be removed to optimize activity. Similarly, based on our preliminary proteolytic cleavage studies, we expect to be able to generate forms of ACE2 shorter than 605AA (~60 kDa) that retain enzymatic activity.

Similar as for mouse rACE2, for the human short rACE2, we expect that it will be as active, if not more active, than the native 110 kDa ACE2. We expect that both human and mouse short ACE2 will have similar potency in cleaving Ang II to form Ang (1-7) in vitro and ex vivo. A low molecular weight human ACE2 is the ultimate therapeutic goal. However, chronic studies will be undertaken in mouse models of DKD (see Aim 2 and 3 below) to examine the therapeutic effect of murine short ACE2 to avoid the problem of neutralizing mouse anti-human ACE2 antibodies previously demonstrated by us when human rACE2 was given to mice[6].

Aim 2. To Evaluate the Protective Effects of Short rACE2 Truncates in Murine Models of Early DKD and Other Indications.

Background and preliminary data. ACE2 amplification by minicircle delivery or administration of intact rACE2 by daily i.p. injections had no detectable effect on blood pressure, albuminuria or kidney histology in the STZ model of DKD[10]. In this model of early DKD, plasma Ang II levels and BP were not increased. By contrast, we have found that in a transgenic renin model of hypertension and Ang II excess, the administration of a modified rACE2 fused with Fc has a marked effect on plasma Ang II, blood pressure and albuminuria (Liu et al. ASN abstract SA-PO521, 2016).

In the absence of any increase in kidney/urinary ACE2 after the administration of intact ACE2 in both models, the differences in these two models can be attributed to the fact that in one model the circulatory RAS is markedly overactive (the renin transgenic) whereas in the STZ model it is not. This is evidenced by the differences in plasma Ang II levels (increased in the renin model and normal in the STZ model). Increasing plasma levels of ACE2 by ACE2-Fc administration in the renin transgenic markedly lower plasma Ang II levels which were elevated at baseline. By contrast, intact ACE2 only marginally lowered Ang II which was not elevated in the STZ model at baseline[10]. The other important consideration is the degree of altered glomerular permeability in the various models of DKD. Urinary ACE2 activity and ACE2 protein are not increased at all by administration of intact ACE2 to STZ or db/db mice[10]. Moreover, infusion of intact rACE2 or intact rACE2-Fc does not increase urine ACE2 in WT mice whereas it increases it markedly in Col4a3−/− mice[10]. Consistent with the importance of altered glomerular permeability for ACE2 kidney delivery, a recent study showed attenuation of kidney injury by intact rACE2 given by minipumps to the Col4a3−/− mice, a model of Alport syndrome with an overactive RAS and heavy proteinuria[113-115].

In this aim, we plan to demonstrate that our short ACE2 proteins, 1-619 and 1-605, and the shortest one generated during Aim 1 studies, work better than intact ACE2 in various models of early DKD where the systemic RAS is not overactive. We postulate that enhancing the degradation of Ang II within the kidney using short rACE2 offers the distinctive advantage of fostering the formation of Ang 1-7 while preventing the accumulation of Ang II locally. This is the proposed mechanism of renoprotection for our short ACE2 truncates that are deliverable to the kidney via glomerular filtration. In this view, ACE2 dissipates Ang II while its formation continues unopposed but there is prevention of excessive accumulation and therefore attenuation of activation of its receptors namely those in glomerular and tubular cells[77,116-118]. Therefore, the attendant stimulation of proinflammatory and profibrotic pathways as well as sodium retention by Ang II driven stimulation of the apical NH3 transporter is apt to be attenuated by infused short ACE2 Indeed, many RAS components in the apical border of renal tubular cells are present and the local formation of ANG II is largely responsible for an overactive kidney RAS in DKD[119]. Of note also, many of the known proinflammatory and profibrotic pathways that are overactive in a hyperglycemic ambience are amplified by excess of Ang II and hyperglycemia, in turn, appears to activate the RAS[120-126]. Thus derives the rationale for ACE2 as a therapy to downregulate the kidney RAS.

Table 1 lists selected models of DKD with a spectrum of differences in glomerular permeability, as inferred roughly by the different degrees of albuminuria. Information as to whether the RAS in the circulation is active or not in these models is also listed. While there is evidence for an active RAS at the kidney level in all these models only the renin Akita mouse has an overactive circulatory RAS[127].

TABLE 1

| | Age Range (wk) | Genetic Background | Sex | uACR Range (μg/mg) | Blood Pressure (mm Hg) | Systemic RAS |
|---|---|---|---|---|---|---|
| STZ[1] | 20-40 | C578L6/J | F | 237 ± 88 | Not elevated | Not overactive |
| STZ[2] | 20-40 | FVB/N | F | 205 ± 51 | Not elevated | Not overactive |
| db/db[3] | 8-24 | C578L6/J | M | 120-300 | Not elevated | Not overactive |
| db/db[4] | 8-24 | C578L6/J | F | 247 ± 54 | Not elevated | Not overactive |
| eNOS(−/−) db/db[5] | 8-20 | C578L6/J | N/S | 2574 ± 974 | Elevated | Not overactive |
| Renin AVV+ Akita[6] | 12-24 | 129/56 | M | 14,531 ± 3555 | Elevated | Not overactive |

[1]Soler et al. 2007
[2]Wysocki et al. 2017
[3]Sharma et al. 2003
[4]Ye et al. 2006
[5]Zhang et al. 2011
[6]Harlan et al. 2017

Proposed Work. The following models of DKD will be studied both in male and female mice and age and sex matched controls (n=10/group) (Initial studies will be conducted in mice treated with STZ for diabetes induction[128] and db/db mice[9, 71, 129]. In these models albuminuria is minimal (Table 1). To examine other models of DKD with more advanced DKD and heavier proteinuria, studies will be done in the renin Akita mice[127] and (eNOS(−/−) db/db mice[130,131]. The latter model lacks the endothelial-specific NOS-3 isoform (eNOS)[130,132]. Importantly, deletion of eNOS in db/db mice, induces an accelerated nephropathy as compared to db/db mice and is more reminiscent of human diabetic nephropathy[130]. As is frequently seen in human type 2 diabetes, in eNOS(−/−) db/db mice, blood pressure is elevated[130, 131] and there is progressive NO dysregulation[133]. Of interest, although the blood pressure control with "triple therapy" (hydralazine, reserpine, hydrocholorothiazide) slowed the progression of diabetic lesions, RAS blockade with captopril provided additional benefits leading to more profound reductions in albuminuria, glomerulosclerosis, markers of tubulointerstitial injury, and macrophage infiltration[131]. This model therefore will be particularly useful in order to establish/disprove putative beneficial effect of short ACE2 proteins and their ability to ameliorate the consequences of deleterious effects of the RAS-mediated disease progression. In this model, the circulating RAS is not overactive as determined by levels of renin and angiotensin II[130]. Thus, the renoprotective effect of short ACE2 truncates in this model should be largely attributable to downregulation of RAS within the kidney and any BP lowering effect that may or may not occur (see expected findings).

The long-term renal effects of truncated ACE2 in mice with DKD (n=10/group) will be examined using two approaches: 1) amplification of short ACE2 using minicircle (MC) DNA delivery; and 2) short rACE2 protein delivery using osmotic minipumps. These forms of therapy will start prior to induction of diabetes (STZ) or at earliest time point (8 weeks of age) in mice with spontaneous diabetes development: db/db mice, (eNOS(−/−) db/db and Renin AVV Akita. The PCR-generated cDNA of short mouse ACE2 (1-619 and 1-605) will be cloned into the pMC BESPX vector under the control of the human ubiquitin promoter and a bovine growth hormone polyadenylation signal, as previously done with intact ACE2-Mc[10]. The circular expression cassette and the resulting short ACE2 minicircle will be administered to mice (30 μg/mouse) (single injection of DNA in a large bolus (2 mL) of PBS into the tail vein) as previously reported by us with intact ACE2[10]. Subsequently, two weeks later diabetes will be induced by STZ also using a protocol previously described by us[10]. Single minicircle administration in mice results in a sustained long-term expression of gene of interest. Therefore, it will be perfectly suitable for studying effects of short ACE2 proteins on DKD, which development often takes about 3 months to be sufficiently robust without the need of recurrent administrations[10]. This is an efficient approach as we can easily inject 10 animals at a time. As an alternative and complementary approach, rACE2 1-619 will be given by osmotic minipumps implanted to mice 1 week before diabetes induction with STZ or at 8 weeks of age in other models. These studies will be done in selected models and with the most renoprotective ACE 2 truncates guided by results of the minicircle studies. The administration of short rACE2 will last for 12-16 weeks (28 d minipumps (Alzet model1004) with replacement every 4 weeks). This relatively long exposure is to show that preventing renal Ang II excess and fostering Ang1-7 chronically prevents/attenuates DKD. Both peptides will be therefore measured by ELISA in plasma, kidney lysates and urine as previously described[7, 9, 10, 134].

We will attempt to demonstrate that short ACE2 prevents/attenuates kidney injury in two models of DKD and mild albuminuria (STZ-treated and db/db mice). As a control, intact ACE2 incorporated in a minicircle will be administered as previously done by us[10] to demonstrate that it is not effective or has markedly reduced effectiveness as compared to short ACE2. Both forms of ACE2 are expected to have very high levels of plasma ACE2 activity but urine ace2 activity is expected to be markedly increased with short but not intact ACE2. The expected renoprotective effect will be assessed by the following parameters: a) light microscopy (to assess mesangial expansion, cellularity)[135] and glomerular size[136]; b) fibronectin and collagen α1 (IV) by mRNA and immunostaining[137]; c) nephrin immunostaining and podocyte count[136]; d) electron microscopy to assess thickening of the basement membrane[138]; e) GFR[10]; and f) molecular inflammatory markers[85, 113, 136]. The general scheme will consist of administering the experimental biologic by MC delivery 2 weeks after induction of diabetes by STZ at 10 weeks of age. Similarly, in db/db mice and for the renin AAV Akita mice, injections will start at 10 weeks of age and the ACE2 biologic given at the same intervals for 12 weeks of follow up. These studies are to a large extent preventative since ACE2 amplification is achieved early on prior to overt kidney damage from diabetes. Blood pressure will be measured two weeks prior to study termination using radiotelemetry. We plan on sacrificing mice at 22 to 24 weeks of age, a time when there is glomerular hypertrophy and mesangial expansion by light microscopy as well as increase thickening basement membrane by EM[127, 130, 131, 139]. Podocyte loss and increased fibronectin is also seen at that time in STZ and db/db mice at this age. The Renin AVV Akita model develops severe glomerular lesions[127] with robust proteinuria (Table 1) and severe hypertension (systolic blood pressure higher than 180 mmHg at 24 weeks of age. A description of this model has just been published[127].

Anticipated results and alternative approaches: We expect that all forms of short ACE2 will be renoprotective in all models whereas intact rACE2 will be effective only in the Renin AAV Akita model with systemic AngII excess (Table 2).

TABLE 2

| Expected Therapeutic Benefits | Intact-ACE2 | Short ACE2 |
|---|---|---|
| STZ | − | +++ |
| db/db | − | +++ |
| eNOS(−/−) db/db | + | ++++ |
| Renin AAV+ Akita | +++ | ++++ |

In the eNOS db/db model intact ACE 2 may have some protective effect if it lowers BP which is not likely since plasma renin and Ang II levels are not increased in this model[130] Markers of therapeutic response will include decreases in UAE rates, attenuation of glomerular, mesangial expansion improved podocyte number, thickness of glomerular basement membranes by EM, glomerular collagen and fibronectin deposition cores (by computerized analysis)[59] as well as a decrease in molecular inflammatory markers. Each intervention that is effective in increasing urine and ACE2 activity within the kidney should reduce kidney cortex AngII levels as well as urinary AngII. The latter is a non-invasive marker of increased intrarenal angiotensin II in situations where circulating Ang II is not increased, such as in the STZ and db/db models of DKD.[31] We do expect increased ACE2 activity, reduced Ang II and increased ANG 1-7 in kidney lysates from animals treated with short ACE2 but not with intact ACE2. The form of ACE2 that offers the best results and is the shortest will be used for the studies in Aim 3.

Aim 3. To Enhance the Duration of Action of the Shortest ACE2 Truncates Using Protein Fusion Technologies and Examine their Renoprotective Action in Models of DKD Alone or with an ACE Inhibitor.

Background and preliminary data: ACE2, as a non-blood resident protein has a limited half-life of hours. (e.g. T½ of untagged short ACE2 1-605 after i.v. injection is ~1.39 hr (n=2)). Accordingly, in the studies in Aim 2, ACE2 1-605 was given continuously by minipumps and MC. To circumvent the limited half-life of the ACE2 variants in blood we will use fusion protein approaches to enhance the half-life of the ACE2 variant and render the ACE2 variants more suitable for chronic use. An approach that has worked very well for intact ACE2 is fusion with the Fc region of human immunoglobulin IgG1 (Liu et al. ASN abstract SA-PO521, 2016). Pharmacokinetic studies confirmed that this modified rACE2 (rmACE2-Fc) has a much extended action time in mice owning to its Fc tag, from <1 hour for un-tagged ACE2 to 7-9 days for ACE2-Fc. The fusion retained the enzymatic activities of ACE2 in comparison to rACE2-Fc. Following injections to mice, the rACE2-Fc exhibited long-acting blood residence time with an improvement of AUC by ~100 fold, as compared to rmACE2.

This fused form of ACE2 with Fc moreover is very effective in controlling hypertension and improving kidney injury in a transgenic model or renin dependent hypertension. However, its larger size renders it non-filterable through the glomerular filtration barrier as it is much larger than the intact ACE2 (molecular weight, 250 kDa). The single i.v injection of rACE2-Fc showed long-lasting effect on preventing bolus AngII induced high blood pressure for more than a week (Liu et al. ASN abstract SA-PO521, 2016).

The ACE2-Fc construct is very large (~250 kD) and does not pass the glomerular filtration barrier in the Renin-TG mice, a model of robust albuminuria (1751±172 µg/mg) (see Table 1). This was demonstrated by unchanged urinary ACE2 activity in Renin-TG mice at the baseline and after intact ACE2-Fc infusion (24.6±4.7 vs. 25.9±6.2 RFU/ug creat/hr, respectively, p=NS, n=5/group). Accordingly, we are striving to develop the shortest ACE2 truncate to confer an extended half-life and yet be filterable and thus capable to exert its full renoprotective action.

Figure 10:
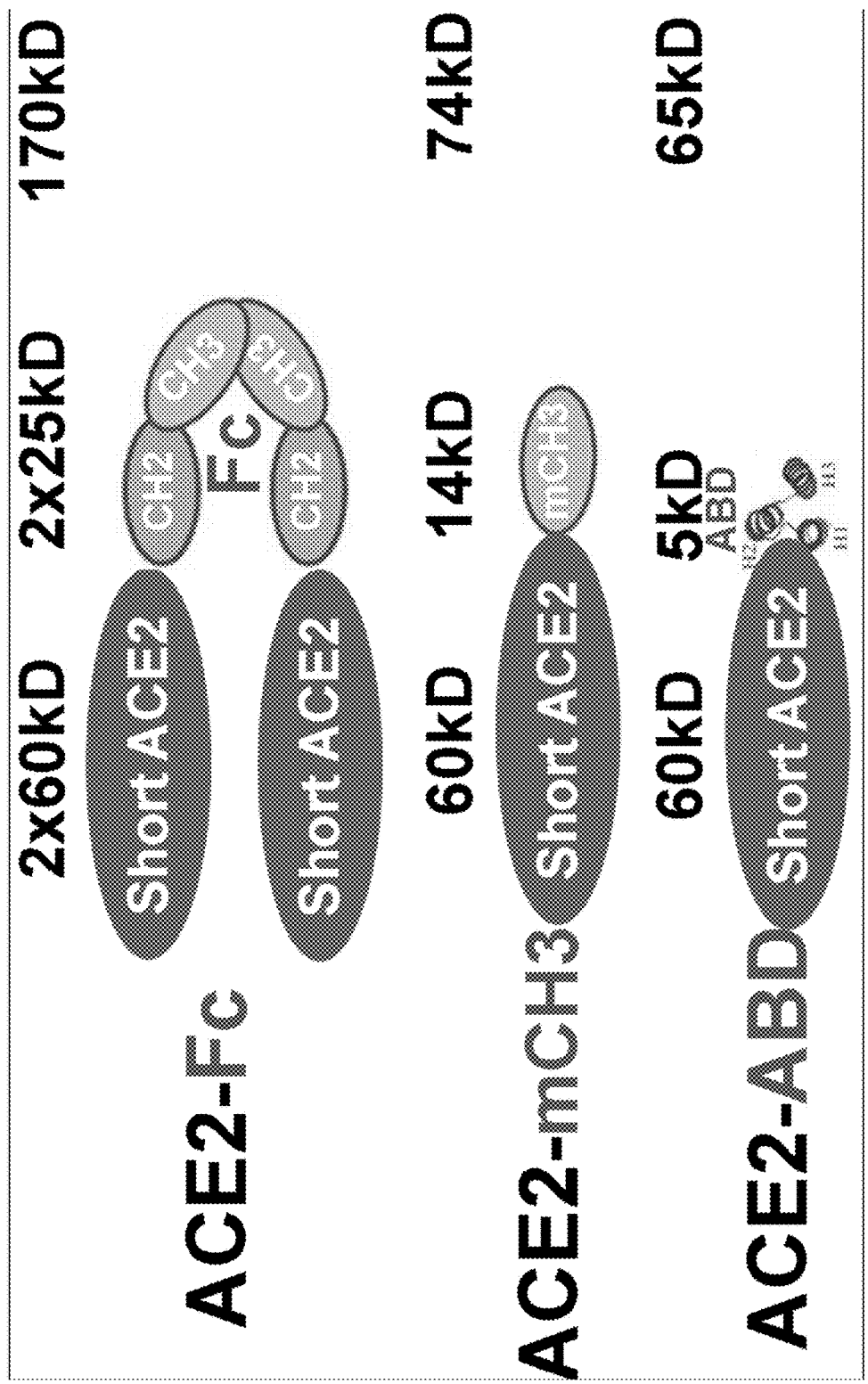
FIG. 10. Different fusion strategies to extend the in vivo half-life of short ACE2. The names of ACE2 fusion proteins are given on the left and their expected molecular sizes on the right. ACE2-Fc dimerizes through the hinge region of the conformation, (b) the charge or hydrophobicity of the molecule at the site of the substitution, and/or (c) the bulk of the side chain.

Proposed work: Our already sequenced "short ACE2" truncates, 1-619 and 1-605 are small enough to be fused with a tag that renders them long acting and yet filterable by the kidney. We have fused already 1-605 with the albumin binding domain of the *streptococcus* G protein (ABD) (see below). However, even shorter ACE2 truncates are desirable for preparing fusion proteins comprising heterologous domains that increase the half-life of the fusion proteins. Therefore, we will select the shortest ACE2 protein with high enzymatic activity and lowest molecular size (identified in Aim 1) to increase its half-life using three different approaches: fusions with Fc, monomeric CH3 and albumin-binding domain tags. (FIG. 10).

We already have made Fc-tagged intact ACE2 and demonstrated its in vivo activities following injection to mice (see above). The Fc portion (~25 kDa), however, naturally exists as a dimer, which brings the total molecular weight of ACE2-Fc to ~250 kDa. This means that if one adds Fc tag to short ACE2 of 60 kD, the expected size of ACE2 will grow to ~170 kD (FIG. 10) and will not be filterable. To achieve a markedly increased half-life of short ACE2 and yet keep molecular size of the fusion protein at a much lower level, we will fuse the shortest ACE2 truncate to two considerably smaller polypeptides: a) monomeric soluble CH3 Fc domain and b) the albumin binding domain of the *streptococcus* G protein (ABD) (FIG. 10). The Fc fragment has two functional domains: CH2 and CH3 which both interact with the Fc receptor (FcRn). It has been shown that a recently engineered soluble monomeric (m)CH3 domain with a lower size (~14 kD) was able to functionally mimic full-size Fc[140]. A shorter but functionally capable mCH3 tag as a therapeutic protein fusion partner could provide the advantage of potentially better tissue penetration, reduced steric hindrance, and increased therapeutic efficacy than Fc itself[140]. Because of its known ability to bind FcRn the soluble mCH3 will be used as an alternative approach to ACE2-Fc to generate ACE2-mCH3 protein with enhanced the half-life. Soluble mCH3 will be accomplished by generating CH3 with specific combination of four mutations which are essential to pH-dependent binding to a human FcRn,[140] mCH3 will be linked to c-terminus of the shortest ACE2 truncate through GS4 linker. Fusing our 1-605 ACE2 (~69 kD) to the soluble monomeric CH3 (~14 kDa) increases its molecular weight to ~83 kDa. This is a marked improvement over the fusion of short ACE2 with Fc (~170 kDa) but we think an even shorter ACE2 construct can be achieved with albumin binding protein (ABD).

The half-life of albumin is very long (19 to 21 days) and fusion to albumin or its structural domains has been used to prolong in vivo half-life of a number of proteins[86,87]. The long $T_{1/2}$ of albumin is believed to be due to its recycling via the neonatal Fc receptor (FcRn). The FcRn-binding site of albumin resides in domain III (DIII)[141]. Serum albumin can be engaged indirectly in half-life extension through molecules with the capacity to non-covalently and reversibly interact with albumin. One of such small molecules is the albumin-binding domain (ABD) derived from streptococcal protein G[142]. We will take advantage that ABD is a small molecule of 46 AA to fuse it with our shortest ACE2. This will translate into only ~5 kD increase in molecular weight (i.e. if the MW of ACE2 is 60 kDa, ACE2-ABD fusion protein will be 65 kDa) (FIG. 10). So far we have already synthesized an artificial gene encoding ABD035, a variant of ABD that has a highly improved albumin binding affinity (fM range) and favorable biophysical characteristics[143]. Moreover, we inserted a flexible linker (G4S3) on the N-terminus of the ABD035 cDNA which will be genetically fused to the C terminus of short ACE2 cDNA to produce an ABD-fusion short ACE2 protein (ACE2-ABD). We are now finalizing the process of generating the ACE2_1-605-ABD chimera which will be done "sewing" PCR of the G4S3-ABD cDNA with the cDNA of the ACE2_1-605. The genes encoding ACE2-ABD will be synthesized and cloned into pcDNA3 vector at the BamHI and XhoI sites and the expression and validation of the construct will be done as described in Aim 1. The ACE2-ABD (and alternatively ACE2-mCH3) will then be over expressed in mammalian cell lines and purified using either Q-Sepharose (as done with the purification of ACE2 1-605 and 1-619) and, if necessary, followed by FPLC and tangential flow filtration. Pharmacokinetics of resulting purified chimeras will be evaluated in a time series experiments where i.p and i.v injections will be done as described for the ACE2-Fc (Liu et al. ASN abstract SA-PO521, 2016). For scanning of the non-fused short rACE2 proteins, the initial approach will involve acute studies for whole body distribution over time using $^{99m}$Tc (6 hr T½) as the radioisotope. $^{99m}$Tc has a relatively short physical half-life, with well-established radiochemistry and is suitable for acute imaging studies[144]. Pharmacokinetics of the radiolabeled agent within kidney and other organs will be determined using regions of interest[53] analysis for each organ separately over time. For imaging the bio-distribution and pharmacokinetics of short rACE2 fusion proteins (with mCH3 and ABD) the proteins will be labeled using a nuclide with a longer physical half-life ($^{111}$In, $T_{1/2}$=2.8 days) which will allow longer term (2-7 days) monitoring[145]. Finally, mice will be sacrificed for kidney harvesting which will be used for immunostaining to obtain kidney cell-specific distribution (His tag antibodies will allow us to differentiate exogenous from endogenous ACE2).

For the demonstration of short ACE2 excretion and kidney uptake by the kidney we will use, in addition to STZ treated, an ACE2KO treated with STZ and a cross of a db/db and ACE2-KO that was generated in our lab. This will facilitate distinction between exogenous and endogenous ACE2. Intact rACE2 will be used for comparative purposes (n=8 per group). Three endpoints will be assessed: 1) Increase urine ACE2 as a marker of glomerular filtration 2) Immunostaining for ACE2 of harvested organs at the end of the acute infusions and 3) Radionuclide imaging for in vivo visualization of agent distribution as markers of kidney filtration and tubular uptake (retention nephrogram) (see FIG. 7). These studies should demonstrate that short ACE2 fused with the optimal tag retains full enzymatic activity in vivo and is delivered to the kidney whereas intact rACE2 is not. The therapeutic potential will be examined first using the shortest ACE2 form with extended half-life. We anticipate that this fused short ACE2 will have an expected half-life of at least 7-14 days and will be the one tested for renoprotection using the criteria described in Aim 2. Dosing will be weekly or biweekly depending on duration of action in terms of in vivo activity and enhancement of angiotensin II degradation as in Aim 1.

Studies with Ramipril (1 mg/Kg/d in drinking water) given for the same period of time will be used for comparison to evaluate the relative efficacy of short rACE2-ABD (or mCH3 as an alternative) as compared to this ACE inhibitor alone in terms of improvement of the kidney parameters outlined in Aim 2. To document the escape phenomenon, blood samples from the tail will be drawn at the start, at 2 wks, and at the end of the study to document that the levels of Ang II are not lower (or even rebound to higher levels) than those of untreated mice. A rebound increase in Ang II levels in plasma after Ramipril has been well described after two weeks of administration[146]. A third group will receive both Ramipril and short rACE2-ABD from the start to examine if this combination results in lower levels of plasma and kidney Ang II and has an additive beneficial than Ramipril alone. These studies will be done in db/db mice and db m controls and the eNOS db/db models only. This will be shown in a separate groups of male and female diabetic mice (n=10 each).

Expected outcomes and alternatives. It is expected that these fusion ACE2 proteins will be filterable through the glomerulus. The demonstration of effective renal uptake of the infused ACE2 will rely on persistence of a nephrogram by radionuclide scanning and demonstration of kidney ACE2 staining. This should be more evident in the ACE2-KO models and possibly in the WT as well where the His-tag antibody will distinguish between exogenous and endogenous ACE2. We anticipate that the uptake will be stronger in the rACE2 fused with ABD (or the alternative mCH3 tag) than short ACE2 alone because binding with the FcRn receptor present in podocytes, endothelial cells and proximal tubule renal cells[79, 147]. We do anticipate that the shorter ACE2 fusion proteins (ACE2-ABD and/or ACE2-mCH3) will be filtered at a rate comparable to that of albumin. Importantly, the FcRn-binding sites on albumin are located in domain III and I and do not overlap or interfere with binding to ABD[84, 142]. As mentioned above, mCH3 effectively binds to FcRn as well. We will exploit this to facilitate the kidney uptake of short ACE2 fused with ABD (and that of ACE2-mCH3). The expected characteristics are listed (Table 4).

TABLE 4

|  | Intact ACE2 | Intact FcACE2 | Short ACE2 | Short ACE2ABD |
|---|---|---|---|---|
| Tag Size | None | Fc (50 kD) | None | ABD (5 kD) |
| Modified ACE2 Size | 110 kD | 250 kD | <69 kD | 74 kD |
| Filterable | No | No | Yes | Yes |
| Reabsorbable | No | Yes | ? | Yes |
| Half Life | Min/Hours* | >7 days | Min/Hours | >7 days |
| Enzymatic Activity | +++ | +++ | ++++ | ++++ |

Based on their characteristics the therapeutic potential of each of the modified ACE2 proteins will exceed that of the intact unmodified ACE2. We anticipate that the long acting short rACE2 will prevent the rebound elevation in plasma AngII levels and also aldosterone seen with ACE inhibitors and this will be accompanied by improved renoprotection. In comparison to Ramipril alone, it is expected that the long acting short ACE2 will be superior in terms of renoprotection owing to the sustained reduction in Ang II and enhanced Ang 1-7 formation.

Statistical analysis: of two independent groups will be performed using unpaired t-test for normally distributed data or the Mann & Whitney test for other distribution patterns. When more than two independent groups will be compared, ANOVA will be used and followed by a Bonferroni correction. Changes over time will be analyzed by repeated-measures ANOVA followed by a post-hoc analysis. The sample size for our experiments will be 10 mice per group based on calculations using an expected difference in means of 25% and a power of 0.8.

Rigor and transparency: The experiments will be done in randomized fashion. All readings will be done in replicates. The effect of sex differences will be taken into account by using animals of both sexes and by analyzing the group sex-specifically.

BIBLIOGRAPHY AND REFERENCES CITED

1. Andersen J T, Dalhus B, Cameron J, Daba M B, Plumridge A, Evans L, Brennan S O, Gunnarsen K S, Bjoras M, Sleep D and Sandlie I. Structure-based mutagenesis reveals the albumin-binding site of the neonatal Fc receptor. Nature communications. 2012; 3:610.

2. Batlle D, Soler M J, and Wysocki, New aspects of the renin-angiotensin system: angiontensin-converting enzyme 2—a potential target for treatment of hypertension and diabetic nephropathy, Curr. Opin Nephrol. Hypertens. 2008 May; 17(3):250-7.

3. Batlle D, Wysocki J, Soler M J and Ranganath K. Angiotensin-converting enzyme 2: enhancing the degradation of angiotensin II as a potential therapy for diabetic nephropathy. Kidney Int. 2012; 81:520-8.

4. Nadarajah R, Milagres R, Dilauro M, Gutsol A, Xiao F, Zimpelmann J, Kennedy C, Wysocki J, Batlle D and Burns K D. Podocyte-specific overexpression of human angiotensin-converting enzyme 2 attenuates diabetic nephropathy in mice. Kidney Int. 2012; 82:292-303.

5. Haber P K, Ye M, Wysocki J, Maier C, Haque S K and Batlle D. Angiotensin-converting enzyme 2-independent action of presumed angiotensin-converting enzyme 2 activators: studies in vivo, ex vivo, and in vitro. Hypertension. 2014; 63:774-82.

6. Wysocki J, Ye M, Rodriguez E, Gonzalez-Pacheco F R, Barrios C, Evora K, Schuster M, Loibner H, Brosnihan K B, Ferrario C M, Penninger J M and Batlle D. Targeting the degradation of angiotensin II with recombinant angiotensin-converting enzyme 2: prevention of angiotensin II-dependent hypertension. Hypertension. 2010; 55:90-8.

7. Ye M, Wysocki J, Gonzalez-Pacheco F R, Salem M, Evora K, Garcia-Halpin L, Poglitsch M, Schuster M and Batlle D. Murine recombinant angiotensin-converting enzyme 2: effect on angiotensin II-dependent hypertension and distinctive angiotensin-converting enzyme 2 inhibitor characteristics on rodent and human angiotensin-converting enzyme 2. Hypertension. 2012; 60:730-40.

8. Wysocki J, Ye M and Baffle D. Plasma and Kidney Angiotensin Peptides: Importance of the Aminopeptidase A/Angiotensin III Axis. Am J Hypertens. 2015; 28:1418-26.

9. Wysocki J, Garcia-Halpin L, Ye M, Maier C, Sowers K, Burns K D and Batlle D. Regulation of urinary ACE2 in diabetic mice. Am J Physiol Renal Physiol. 2013; 305:F600-11.

10. Wysocki J, Ye M, Khattab A M, Fogo A, Martin A, David N V, Kanwar Y, Osborn M and Batlle D. Angiotensin-converting enzyme 2 amplification limited to the circulation does not protect mice from development of diabetic nephropathy. Kidney Int. 2017; 91:1336-1346.

11. Cosgrove D, Meehan D T, Grunkemeyer J A, Kornak J M, Sayers R, Hunter W J and Samuelson G C. Collagen COL4A3 knockout: a mouse model for autosomal Alport syndrome. Genes & development. 1996; 10:2981-92.

12. Fisher N D, Price D A, Litchfield W R, Williams G H and Hollenberg N K. Renal response to captopril reflects state of local renin system in healthy humans. Kidney Int. 1999; 56:635-41.

13. Price D A, Porter L E, Gordon M, Fisher N D, De'Oliveira J M, Laffel L M, Passan D R, Williams G H and Hollenberg N K. The paradox of the low-renin state in diabetic nephropathy. J Am Soc Nephrol. 1999; 10:2382-91.

14. Christlieb A R, Kaldany A and D'Elia J A. Plasma renin activity and hypertension in diabetes mellitus. Diabetes. 1976; 25:969-74.

15. Rosenberg M E, Smith L J, Correa-Rotter R and Hostetter T H. The paradox of the renin-angiotensin system in chronic renal disease. Kidney Int. 1994; 45:403-10.

16. Peti-Peterdi J, Kang J J and Toma I. Activation of the renal renin-angiotensin system in diabetes—new concepts. Nephrology Dialysis Transplantation. 2008; 23:3047-3049.

17. Gurley S B and Coffman T M. The renin-angiotensin system and diabetic nephropathy. Seminars in nephrology. 2007; 27:144-52.

18. Zatz R, Dunn B R, Meyer T W, Anderson S, Rennke H G and Brenner B M. Prevention of diabetic glomerulopathy by pharmacological amelioration of glomerular capillary hypertension. The Journal of clinical investigation. 1986; 77:1925-30.

19. Anderson S, Jung F F and Ingelfinger J R. Renal renin-angiotensin system in diabetes: functional, immunohistochemical, and molecular biological correlations. Am J Physiol. 1993; 265:F477-86.

20. Raij L. The pathophysiologic basis for blocking the renin-angiotensin system in hypertensive patients with renal disease. Am J Hypertens. 2005; 18:95s-99s.

21. Anderson S, Rennke H G and Brenner B M. Therapeutic advantage of converting enzyme inhibitors in arresting progressive renal disease associated with systemic hypertension in the rat. Journal of Clinical Investigation. 1986; 77:1993-2000.

22. Kobori H, Harrison-Bernard L M and Navar L G. Urinary excretion of angiotensinogen reflects intrarenal angiotensinogen production. Kidney international. 2002; 61:579-585.

23. Lo C-S, Chang S-Y, Chenier I, Filep J G, Ingelfinger J R, Zhang S L and Chan J S D. Heterogeneous Nuclear Ribonucleoprotein F Suppresses Angiotensinogen Gene Expression and Attenuates Hypertension and Kidney Injury in Diabetic Mice. Diabetes. 2012; 61:2597-2608.

24. Durvasula R V, Petermann A T, Hiromura K, Blonski M, Pippin J, Mundel P, Pichler R, Griffin S, Couser W G and Shankland S J. Activation of a local tissue angiotensin system in podocytes by mechanical strain. Kidney Int. 2004; 65:30-9.

25. Durvasula R V and Shankland S J. Activation of a local renin angiotensin system in podocytes by glucose. Am J Physiol Renal Physiol. 2008; 294:F830-9.

26. Ingelfinger J R, Zuo W M, Fon E A, Ellison K E and Dzau V J. In situ hybridization evidence for angiotensinogen messenger RNA in the rat proximal tubule. An hypothesis for the intrarenal renin angiotensin system. The Journal of clinical investigation. 1990; 85:417-23.

27. Mills K T, Kobori H, Hamm L L, Alper A B, Khan I E, Rahman M, Navar L G, Liu Y, Browne G M, Batuman V, He J and Chen J. Increased urinary excretion of angiotensinogen is associated with risk of chronic kidney disease. Nephrology Dialysis Transplantation. 2012; 27:3176-3181.

28. Kamiyama M, Zsombok A and Kobori H. Urinary angiotensinogen as a novel early biomarker of intrarenal renin-angiotensin system activation in experimental type 1 diabetes. Journal of pharmacological sciences. 2012; 119: 314-23.

29. Ye M W J, Khattab A, Issa H, Gutterman M, Molitch M, Batlle D. Urinary Angiotensinogen (AOG) is Increased in Type I Diabetes with Microalbuminuria. 2016.

30. Afkarian M, Hirsch I B, Tuttle K R, Greenbaum C, Himmelfarb J and de Boer I H. Urinary excretion of RAS, BMP, and WNT pathway components in diabetic kidney disease. Physiological reports. 2014; 2:e12010.

31. Wysocki J, Goodling A, Burgaya M, Whitlock K, Ruzinski J, Batlle D and Afkarian M. Urine RAS components in mice and people with type 1 diabetes and chronic kidney disease. Am J Physiol Renal Physiol. 2017: ajprenal 00074 2017.

32. Brenner B M, Cooper M E, de Zeeuw D, Keane W F, Mitch W E, Parving H H, Remuzzi G, Snapinn S M, Zhang Z and Shahinfar S. Effects of losartan on renal and cardiovascular outcomes in patients with type 2 diabetes and nephropathy. The New England journal of medicine. 2001; 345:861-9.

33. Fogo A B. Renal fibrosis and the renin-angiotensin system. Advances in nephrology from the Necker Hospital. 2001; 31:69-87.

34. Lewis E J, Hunsicker L G, Bain R P and Rohde R D. The effect of angiotensin-converting-enzyme inhibition on diabetic nephropathy. The Collaborative Study Group. The New England journal of medicine. 1993; 329:1456-62.

35. Lewis E J, Hunsicker L G, Clarke W R, Berl T, Pohl M A, Lewis J B, Ritz E, Atkins R C, Rohde R and Raz I. Renoprotective effect of the angiotensin-receptor antagonist irbesartan in patients with nephropathy due to type 2 diabetes. The New England journal of medicine. 2001; 345: 851-60.

36. Yamada K, Iyer S N, Chappell M C, Ganten D and Ferrario C M. Converting enzyme determines plasma clearance of angiotensin-(1-7). Hypertension. 1998; 32:496-502.

37. Santos R A, Ferreira A J, Verano-Braga T and Bader M. Angiotensin-converting enzyme 2, angiotensin-(1-7) and Mas: new players of the renin-angiotensin system. The Journal of endocrinology. 2013; 216:R1-r17.

38. Welches W R, Santos R A, Chappell M C, Brosnihan K B, Greene L J and Ferrario C M. Evidence that prolyl endopeptidase participates in the processing of brain angiotensin. Journal of hypertension. 1991; 9:631-8.

39. Grobe N, Weir N M, Leiva O, Ong F S, Bernstein K E, Schmaier A H, Morris M and Elased K M. Identification of prolyl carboxypeptidase as an alternative enzyme for processing of renal angiotensin II using mass spectrometry. American journal of physiology Cell physiology. 2013; 304:C945-53.

40. Shariat-Madar Z, Mandi F and Schmaier A H. Identification and characterization of prolylcarboxypeptidase as an endothelial cell prekallikrein activator. J Biol Chem. 2002; 277:17962-9.

41. Velez J C. Prolyl carboxypeptidase: a forgotten kidney angiotensinase. Focus on "Identification of prolyl carboxypeptidase as an alternative enzyme for processing of renal angiotensin II using mass spectrometry". American journal of physiology Cell physiology. 2013; 304:C939-40.

42. Maier C, Schadock I, Haber P K, Wysocki J, Ye M, Kanwar Y, Flask C A, Yu X, Hoit B D, Adams G N, Schmaier A H, Bader M and Batlle D. Prolylcarboxypeptidase deficiency is associated with increased blood pressure, glomerular lesions, and cardiac dysfunction independent of altered circulating and cardiac angiotensin II. Journal of molecular medicine (Berlin, Germany). 2017.

43. Vickers C, Hales P, Kaushik V, Dick L, Gavin J, Tang J, Godbout K, Parsons T, Baronas E, Hsieh F, Acton S, Patane M, Nichols A and Tummino P. Hydrolysis of biological peptides by human angiotensin-converting enzyme-related carboxypeptidase. J Biol Chem. 2002; 277:14838-43.

44. Haschke M, Schuster M, Poglitsch M, Loibner H, Salzberg M, Bruggisser M, Penninger J and Krahenbuhl S. Pharmacokinetics and pharmacodynamics of recombinant human angiotensin-converting enzyme 2 in healthy human subjects. Clinical pharmacokinetics. 2013; 52:783-92.

45. Campbell D J. The site of angiotensin production. Journal of hypertension. 1985; 3:199-207.

46. Lorenz J N. Chymase: the other ACE? Am J Physiol Renal Physiol. 2010; 298:F35-6.

47. Li M, Liu K, Michalicek J, Angus J A, Hunt J E, Dell'Italia L J, Feneley M P, Graham R M and Husain A. Involvement of chymase-mediated angiotensin II generation in blood pressure regulation. The Journal of clinical investigation. 2004; 114:112-20.

48. Park S, Bivona B J, Kobori H, Seth D M, Chappell M C, Lazartigues E and Harrison-Bernard L M. Major role for ACE-independent intrarenal ANG II formation in type II diabetes. Am J Physiol Renal Physiol. 2010; 298:F37-48.

49. Sharman D C, Morris A D and Struthers A D. Gradual reactivation of vascular angiotensin I to angiotensin II conversion during chronic ACE inhibitor therapy in patients with diabetes mellitus. Diabetologia. 2007; 50:2061-6.

50. van de Wal R M, Plokker H W, Lok D J, Boomsma F, van der Horst F A, van Veldhuisen D J, van Gilst W H and Voors A A. Determinants of increased angiotensin II levels in severe chronic heart failure patients despite ACE inhibition. International journal of cardiology. 2006; 106:367-72.

51. Berry C. Clinical implications of increased plasma angiotensin II concentrations despite ACE inhibitor therapy in patients with congestive heart failure: the issue of non-compliance with therapy. European heart journal. 2000; 21:1484-5.

52. Urata H, Healy B, Stewart R W, Bumpus F M and Husain A. Angiotensin II-forming pathways in normal and failing human hearts. Circ Res. 1990; 66:883-90.

53. Roig E, Perez-Villa F, Morales M, Jimenez W, Orus J, Heras M and Sanz G. Clinical implications of increased plasma angiotensin II despite ACE inhibitor therapy in patients with congestive heart failure. European heart journal. 2000; 21:53-7.

54. Shiigai T and Shichiri M. Late escape from the antiproteinuric effect of ace inhibitors in nondiabetic renal disease. American journal of kidney diseases: the official journal of the National Kidney Foundation. 2001; 37:477-83.

55. Athyros V G, Mikhailidis D P, Kakafika A I, Tziomalos K and Karagiannis A. Angiotensin II reactivation and aldosterone escape phenomena in renin-angiotensin-aldosterone system blockade: is oral renin inhibition the solution? Expert opinion on pharmacotherapy. 2007; 8:529-35.

56. Urata H, Kinoshita A, Misono K S, Bumpus F M and Husain A. Identification of a highly specific chymase as the major angiotensin II-forming enzyme in the human heart. J Biol Chem. 1990; 265:22348-57.

57. Wei C C, Hase N, Inoue Y, Bradley E W, Yahiro E, Li M, Naqvi N, Powell P C, Shi K, Takahashi Y, Saku K, Urata H, Dell'italia L J and Husain A. Mast cell chymase limits the cardiac efficacy of Ang I-converting enzyme inhibitor therapy in rodents. The Journal of clinical investigation. 2010; 120:1229-39.

58. Tom B, Garrelds I M, Scalbert E, Stegmann A P, Boomsma F, Saxena P R and Danser A H. ACE-versus chymase-dependent angiotensin II generation in human coronary arteries: a matter of efficiency? Arteriosclerosis, thrombosis, and vascular biology. 2003; 23:251-6.

59. Urata H, Boehm K D, Philip A, Kinoshita A, Gabrovsek J, Bumpus F M and Husain A. Cellular localization and regional distribution of an angiotensin II-forming chymase in the heart. The Journal of clinical investigation. 1993; 91:1269-81.

60. Grima M, Ingert C, Michel B, Barthelmebs M and Imbs J L. Renal tissue angiotensins during converting enzyme inhibition in the spontaneously hypertensive rat. Clinical and experimental hypertension (New York, N.Y.: 1993). 1997; 19:671-85.

61. Biollaz J, Schelling J L, Jacot Des Combes B, Brunner D B, Desponds G, Brunner H R, Ulm E H, Hichens M and Gomez H J. Enalapril maleate and a lysine analogue (MK-521) in normal volunteers; relationship between plasma drug levels and the renin angiotensin system. British journal of clinical pharmacology. 1982; 14:363-8.

62. Giani J F, Janjulia T, Kamat N, Seth D M, Blackwell W L, Shah K H, Shen X Z, Fuchs S, Delpire E, Toblli J E, Bernstein K E, McDonough A A and Gonzalez-Villalobos R A. Renal angiotensin-converting enzyme is essential for the hypertension induced by nitric oxide synthesis inhibition. J Am Soc Nephrol. 2014; 25:2752-63.

63. Ferrario C M, Jessup J, Chappell M C, Averill D B, Brosnihan K B, Tallant E A, Diz D I and Gallagher P E. Effect of angiotensin-converting enzyme inhibition and angiotensin II receptor blockers on cardiac angiotensin-converting enzyme 2. Circulation. 2005; 111:2605-10.

64. van den Meiracker A H, Man in't Veld A J, Admiraal P J, Ritsema van Eck H J, Boomsma F, Derkx F H and Schalekamp M A. Partial escape of angiotensin converting enzyme (ACE) inhibition during prolonged ACE inhibitor treatment: does it exist and does it affect the antihypertensive response? Journal of hypertension. 1992; 10:803-12.

65. Komine N, Khang S, Wead L M, Blantz R C and Gabbai F B. Effect of combining an ACE inhibitor and an angiotensin II receptor blocker on plasma and kidney tissue angiotensin II levels. American journal of kidney diseases: the official journal of the National Kidney Foundation. 2002; 39:159-64.

66. Grobe J L, Mecca A P, Lingis M, Shenoy V, Bolton T A, Machado J M, Speth R C, Raizada M K and Katovich M J. Prevention of angiotensin II-induced cardiac remodeling by angiotensin-(1-7). American journal of physiology Heart and circulatory physiology. 2007; 292:H736-42.

67. Carney E F. Diabetic nephropathy: Renoprotective effects of angiotensin 1-7. Nature reviews Nephrology. 2014; 10:240.

68. Mori J, Patel V B, Ramprasath T, Alrob O A, DesAulniers J, Scholey J W, Lopaschuk G D and Oudit G Y. Angiotensin 1-7 mediates renoprotection against diabetic nephropathy by reducing oxidative stress, inflammation, and lipotoxicity. Am J Physiol Renal Physiol. 2014; 306:F812-21.

69. Simoes e Silva A C, Silveira K D, Ferreira A J and Teixeira M M. ACE2, angiotensin-(1-7) and Mas receptor axis in inflammation and fibrosis. British journal of pharmacology. 2013; 169:477-92.

70. Simões e Silva A C and Teixeira M M. ACE inhibition, ACE2 and angiotensin-(1?7) axis in kidney and cardiac inflammation and fibrosis. Pharmacological Research. 2016; 107:154-162.

71. Ye M, Wysocki J, William J, Soler M J, Cokic I and Batlle D. Glomerular localization and expression of Angiotensin-converting enzyme 2 and Angiotensin-converting enzyme: implications for albuminuria in diabetes. J Am Soc Nephrol. 2006; 17:3067-75.

72. Ye M, Wysocki J, Naaz P, Salabat M R, LaPointe M S and Batlle D. Increased ACE 2 and decreased ACE protein in renal tubules from diabetic mice: a renoprotective combination? Hypertension. 2004; 43:1120-5.

73. Brasen J C, Burford J L, McDonough A A, Holstein-Rathlou N H and Peti-Peterdi J. Local pH domains regulate NHE3-mediated Na(+) reabsorption in the renal proximal tubule. Am J Physiol Renal Physiol. 2014; 307:F1249-62.

74. Crowley S D, Gurley S B, Herrera M J, Ruiz P, Griffiths R, Kumar A P, Kim H S, Smithies O, Le T H and Coffman T M. Angiotensin II causes hypertension and cardiac hypertrophy through its receptors in the kidney. Proceedings of the National Academy of Sciences of the United States of America. 2006; 103:17985-90.

75. Gonzalez A A, Green T, Luffman C, Bourgeois C R T, Gabriel Navar L and Prieto M C. Renal medullary cyclooxygenase-2 and (pro)renin receptor expression during angiotensin II-dependent hypertension. Am J Physiol Renal Physiol. 2014; 307:F962-70.

76. Gonzalez-Villalobos R A, Janjoulia T, Fletcher N K, Giani J F, Nguyen M T, Riquier-Brison A D, Seth D M, Fuchs S, Eladari D, Picard N, Bachmann S, Delpire E, Peti-Peterdi J, Navar L G, Bernstein K E and McDonough A A. The absence of intrarenal ACE protects against hypertension. The Journal of clinical investigation. 2013; 123: 2011-23.

77. Gurley S B, Riquier A D M, Schnermann J, Sparks M A, Allen A M, Haase V H, Snouwaert J N, Le T H, McDonough A A, Koller B H and Coffman T M. AT(1A) Angiotensin Receptors in the Renal Proximal Tubule Regulate Blood Pressure. Cell metabolism. 2011; 13:469-75.

78. Nguyen M T, Han J, Ralph D L, Veiras L C and McDonough A A. Short-term nonpressor angiotensin II infusion stimulates sodium transporters in proximal tubule and distal nephron. Physiological reports. 2015; 3.

79. Akilesh S, Huber T B, Wu H, Wang G, Hartleben B, Kopp J B, Miner J H, Roopenian D C, Unanue E R and Shaw A S. Podocytes use FcRn to clear IgG from the glomerular basement membrane. Proceedings of the National Academy of Sciences of the United States of America. 2008; 105:967-72.

80. Dickson L E, Wagner M C, Sandoval R M and Molitoris B A. The proximal tubule and albuminuria: really! J Am Soc Nephrol. 2014; 25:443-53.

81. Park C H and Maack T. Albumin absorption and catabolism by isolated perfused proximal convoluted tubules of the rabbit. The Journal of clinical investigation. 1984; 73:767-77.

82. Russo L M, Sandoval R M, McKee M, Osicka T M, Collins A B, Brown D, Molitoris B A and Comper W D. The normal kidney filters nephrotic levels of albumin retrieved by proximal tubule cells: retrieval is disrupted in nephrotic states. Kidney Int. 2007; 71:504-13.

83. Sandoval R M, Wagner M C, Patel M, Campos-Bilderback S B, Rhodes G J, Wang E, Wean S E, Clendenon S S and Molitoris B A. Multiple factors influence glomerular albumin permeability in rats. J Am Soc Nephrol. 2012; 23:447-57.

84. Chaudhury C, Brooks C L, Carter D C, Robinson J M and Anderson C L. Albumin binding to FcRn: distinct from the FcRn-IgG interaction. Biochemistry. 2006; 45:4983-90.

85. Haymann J P, Levraud J P, Bouet S, Kappes V, Hagege J, Nguyen G, Xu Y, Rondeau E and Sraer J D. Characterization and localization of the neonatal Fc receptor in adult human kidney. J Am Soc Nephrol. 2000; 11:632-9.

86. Kontermann R E. Strategies for extended serum half-life of protein therapeutics. Current opinion in biotechnology. 2011; 22:868-76.

87. Strohl W R. Fusion Proteins for Half-Life Extension of Biologics as a Strategy to Make Biobetters. BioDrugs: clinical immunotherapeutics, biopharmaceuticals and gene therapy. 2015; 29:215-39.

88. Suzuki T, Ishii-Watabe A, Tada M, Kobayashi T, Kanayasu-Toyoda T, Kawanishi T and Yamaguchi T. Importance of neonatal FcR in regulating the serum half-life of therapeutic proteins containing the Fc domain of human IgG1: a comparative study of the affinity of monoclonal antibodies and Fc-fusion proteins to human neonatal FcR. Journal of immunology (Baltimore, Md.: 1950). 2010; 184: 1968-76.

89. Schulte S. Half-life extension through albumin fusion technologies. Thrombosis research. 2009; 124 Suppl 2:S6-8.

90. Macdougall I C, Gray S J, Elston O, Breen C, Jenkins B, Browne J and Egrie J. Pharmacokinetics of novel erythropoiesis stimulating protein compared with epoetin alfa in dialysis patients. J Am Soc Nephrol. 1999; 10:2392-5.

91. Schellenberger V, Wang C W, Geething N C, Spink B J, Campbell A, To W, Scholle M D, Yin Y, Yao Y, Bogin O, Cleland J L, Silverman J and Stemmer W P. A recombinant polypeptide extends the in vivo half-life of peptides and proteins in a tunable manner. Nat Biotechnol. 2009; 27:1186-90.

92. Christensen E I and Birn H. Megalin and cubilin: multifunctional endocytic receptors. Nature reviews Molecular cell biology. 2002; 3:256-66.

93. Dolman M E, Harmsen S, Storm G, Hennink W E and Kok R J. Drug targeting to the kidney: Advances in the active targeting of therapeutics to proximal tubular cells. Advanced drug delivery reviews. 2010; 62:1344-57.

94. Moestrup S K and Verroust P J. Megalin- and cubilin-mediated endocytosis of protein-bound vitamins, lipids, and hormones in polarized epithelia. Annual review of nutrition. 2001; 21:407-28.

95. Saito A, Sato H, Iino N and Takeda T. Molecular mechanisms of receptor-mediated endocytosis in the renal proximal tubular epithelium. Journal of biomedicine & biotechnology. 2010; 2010:403272.

96. Franssen E J, Koiter J, Kuipers C A, Bruins A P, Moolenaar F, de Zeeuw D, Kruizinga W H, Kellogg R M and Meijer D K. Low molecular weight proteins as carriers for renal drug targeting. Preparation of drug-protein conjugates and drug-spacer derivatives and their catabolism in renal cortex homogenates and lysosomal lysates. J Med Chem. 1992; 35:1246-59.

97. Franssen E J, van Amsterdam R G, Visser J, Moolenaar F, de Zeeuw D and Meijer D K. Low molecular weight proteins as carriers for renal drug targeting: naproxen-lysozyme. Pharmaceutical research. 1991; 8:1223-30.

98. Haas M, Moolenaar F, Meijer D K and de Zeeuw D. Specific drug delivery to the kidney. Cardiovascular drugs and therapy. 2002; 16:489-96.

99. Kok R J, Grijpstra F, Walthuis R B, Moolenaar F, de Zeeuw D and Meijer D K. Specific delivery of captopril to the kidney with the prodrug captopril-lysozyme. The Journal of pharmacology and experimental therapeutics. 1999; 288:281-5.

100. Zhou P, Sun X and Zhang Z. Kidney-targeted drug delivery systems. Acta Pharmaceutica Sinica B. 2014; 4:37-42.

101. Wysocki J R J, Afkarian M, Batlle D. Urinary prorenin is increased in patients with type 1 diabetes and nephropathy. ASN. 2016; Kidney Week.

102. Comper W D and Glasgow E F. Charge selectivity in kidney ultrafiltration. Kidney Int. 1995; 47:1242-51.

103. Caliceti P and Veronese F M. Pharmacokinetic and biodistribution properties of poly(ethylene glycol)-protein conjugates. Advanced drug delivery reviews. 2003; 55:1261-77.

104. Jevsevar S, Kunstelj M and Porekar V G. PEGylation of therapeutic proteins. Biotechnology journal. 2010; 5:113-28.

105. Kanwar Y S and Farquhar M G. Anionic sites in the glomerular basement membrane. In vivo and in vitro localization to the laminae rarae by cationic probes. The Journal of cell biology. 1979; 81:137-53.

106. Rennke H G, Cotran R S and Venkatachalam M A. Role of molecular charge in glomerular permeability. Tracer studies with cationized ferritins. The Journal of cell biology. 1975; 67:638-46.

107. Kanwar Y S and Farquhar M G. Presence of heparan sulfate in the glomerular basement membrane. Proceedings of the National Academy of Sciences of the United States of America. 1979; 76:1303-7.

108. Salem E S, Grobe N and Elased K M. Insulin treatment attenuates renal ADAM17 and ACE2 shedding in diabetic Akita mice. Am J Physiol Renal Physiol. 2014; 306:F629-39.

109. Goorno W E, Rector F C, Jr. and Seldin D W. Relation of renal gluconeogenesis to ammonia production in the dog and rat. The American journal of physiology. 1967; 213:969-74.

110. Jiang F, Yang J, Zhang Y, Dong M, Wang S, Zhang Q, Liu F F, Zhang K and Zhang C. Angiotensin-converting enzyme 2 and angiotensin 1-7: novel therapeutic targets. Nature reviews Cardiology. 2014; 11:413-26.

111. Towler P, Staker B, Prasad S G, Menon S, Tang J, Parsons T, Ryan D, Fisher M, Williams D, Dales N A, Patane M A and Pantoliano M W. ACE2 X-ray structures reveal a large hinge-bending motion important for inhibitor binding and catalysis. J Biol Chem. 2004; 279:17996-8007.

112. Liu P, Wysocki J, Serfozo P, Ye M, Souma T, D B and J. J. A Fluorometric Method of Measuring Carboxypeptidase Activities for Angiotensin II and Apelin 13. Scientific Reports. 2017.

113. Bae E H, Fang F, Williams V R, Konvalinka A, Zhou X, Patel V B, Song X, John R, Oudit G Y, Pei Y and Scholey J W. Murine recombinant angiotensin-converting enzyme 2 attenuates kidney injury in experimental Alport syndrome. Kidney Int. 2017.

114. Ross M J and Nangaku M. ACE2 as therapy for glomerular disease: the devil is in the detail. Kidney International. 2017; 91:1269-1271.

115. Ross M J and Nangaku M. ACE2 as therapy for glomerular disease: the devil is in the detail. Kidney Int. 2017; 91:1269-1271.

116. Cheng H F, Becker B N, Burns K D and Harris R C. Angiotensin II upregulates type-1 angiotensin II receptors in renal proximal tubule. Journal of Clinical Investigation. 1995; 95:2012-2019.

117. Schelling J R, Hanson A S, Marzec R and Linas S L. Cytoskeleton-dependent endocytosis is required for apical type 1 angiotensin II receptor-mediated phospholipase C activation in cultured rat proximal tubule cells. J Clin Invest. 1992; 90:2472-80.

118. Becker B N, Cheng H-f, Hammond T G and Harris R C. The Type 1 Angiotensin II Receptor Tail Affects Receptor Targeting, Internalization, and Membrane Fusion Properties. Molecular Pharmacology. 2004; 65:362.

119. Culver S, Li C and Siragy H M. Intrarenal Angiotensin-Converting Enzyme: the Old and the New. Current hypertension reports. 2017; 19:80.

120. Border W A and Noble N A. Interactions of Transforming Growth Factor-B and Angiotensin II in Renal Fibrosis. Hypertension. 1998; 31:181-188.

121. Mezzano S A, Ruiz-Ortega M and Egido J. Angiotensin II and Renal Fibrosis. Hypertension. 2001; 38:635-638.

122. Suzuki Y, Ruiz-Ortega M, Lorenzo O, Ruperez M, Esteban V and Egido J. Inflammation and angiotensin II. The International Journal of Biochemistry & Cell Biology. 2003; 35:881-900.

123. Benigni A, Cassis P and Remuzzi G. Angiotensin II revisited: new roles in inflammation, immunology and aging. EMBO Molecular Medicine. 2010; 2:247-57.

124. Sun L, Xiao L, Nie J, Liu F, Ling G, Zhu X, Tang W, Chen W, Xia Y, Zhan M, Ma M, Peng Y, Liu H, Liu Y and Kanwar Y S. p66Shc mediates high-glucose and angiotensin II-induced oxidative stress renal tubular injury via mitochondrial-dependent apoptotic pathway. Am J Physiol Renal Physiol. 2010; 299:F1014-25.

125. Chen J, Chen J K, Nagai K, Plieth D, Tan M, Lee T C, Threadgill D W, Neilson E G and Harris R C. EGFR Signaling Promotes TGFβ-Dependent Renal Fibrosis. J Am Soc Nephrol. 2012; 23:215-24.

126. Okada H. A Look at Transactivation of the EGF Receptor by Angiotensin II. J Am Soc Nephrol. 2012; 23:183-5.

127. Harlan S M, Heinz-Taheny K M, Sullivan J M, Wei T, Baker H E, Jaqua D L, Qi Z, Cramer M S, Shiyanova T L, Breyer M D and Heuer J G. Progressive Renal Disease Established by Renin-Coding Adeno-Associated Virus-Driven Hypertension in Diverse Diabetic Models. J Am Soc Nephrol. 2017.

128. Soler M J, Wysocki J, Ye M, Lloveras J, Kanwar Y and Batlle D. ACE2 inhibition worsens glomerular injury in association with increased ACE expression in streptozotocin-induced diabetic mice. Kidney Int. 2007; 72:614-23.

129. Wysocki J, Ye M, Soler M J, Gurley S B, Xiao H D, Bernstein K E, Coffman T M, Chen S and Batlle D. ACE and ACE2 activity in diabetic mice. Diabetes. 2006; 55:2132-9.

130. Zhao H J, Wang S, Cheng H, Zhang M Z, Takahashi T, Fogo A B, Breyer M D and Harris R C. Endothelial nitric oxide synthase deficiency produces accelerated nephropathy in diabetic mice. J Am Soc Nephrol. 2006; 17:2664-9.

131. Zhang M Z, Wang S, Yang S, Yang H, Fan X, Takahashi T and Harris R C. Role of blood pressure and the renin-angiotensin system in development of diabetic nephropathy (DN) in eNOS−/− db/db mice. Am J Physiol Renal Physiol. 2012; 302:F433-8.

132. Nakagawa T, Sato W, Glushakova O, Heinig M, Clarke T, Campbell-Thompson M, Yuzawa Y, Atkinson M A, Johnson R J and Croker B. Diabetic endothelial nitric oxide synthase knockout mice develop advanced diabetic nephropathy. Journal of the American Society of Nephrology: JASN. 2007; 18:539-50.

133. Quaggin S E and Coffman T M. Toward a mouse model of diabetic nephropathy: is endothelial nitric oxide synthase the missing link? Journal of the American Society of Nephrology: JASN. 2007; 18:364-6.

134. Maier C, Schadock I, Haber P K, Wysocki J, Ye M, Kanwar Y, Flask C A, Yu X, Hoit B D, Adams G N, Schmaier A H, Bader M and Batlle D. Prolylcarboxypeptidase deficiency is associated with increased blood pressure, glomerular lesions, and cardiac dysfunction independent of altered circulating and cardiac angiotensin II. J Mol Med (Berl). 2017; 95:473-486.

135. Nagasu H, Satoh M, Kiyokage E, Kidokoro K, Toida K, Channon K M, Kanwar Y S, Sasaki T and Kashihara N. Activation of endothelial NAD(P)H oxidase accelerates early glomerular injury in diabetic mice. Lab Invest. 2016; 96:25-36.

136. Hudkins K L, Pichaiwong W, Wietecha T, Kowalewska J, Banas M C, Spencer M W, Muhlfeld A, Koelling M, Pippin J W, Shankland S J, Askari B, Rabaglia M E, Keller M P, Attie A D and Alpers C E. BTBR Ob/Ob mutant mice model progressive diabetic nephropathy. J Am Soc Nephrol. 2010; 21:1533-42.

137. Oudit G Y, Herzenberg A M, Kassiri Z, Wong D, Reich H, Khokha R, Crackower M A, Backx P H, Penninger J M and Scholey J W. Loss of angiotensin-converting enzyme-2 leads to the late development of angiotensin II-dependent glomerulosclerosis. The American journal of pathology. 2006; 168:1808-20.

138. Sung S H, Ziyadeh F N, Wang A, Pyagay P E, Kanwar Y S and Chen S. Blockade of vascular endothelial growth factor signaling ameliorates diabetic albuminuria in mice. J Am Soc Nephrol. 2006; 17:3093-104.

139. Brosius F C, 3rd, Alpers C E, Bottinger E P, Breyer M D, Coffman T M, Gurley S B, Harris R C, Kakoki M, Kretzler M, Leiter E H, Levi M, McIndoe R A, Sharma K, Smithies O, Susztak K, Takahashi N and Takahashi T. Mouse models of diabetic nephropathy. J Am Soc Nephrol. 2009; 20:2503-12.

140. Ying T, Chen W, Feng Y, Wang Y, Gong R and Dimitrov D S. Engineered soluble monomeric IgG1 CH3 domain: generation, mechanisms of function, and implications for design of biological therapeutics. J Biol Chem. 2013; 288:25154-64.

141. Sand K M K, Dalhus B, Christianson G J, Bern M, Foss S, Cameron J, Sleep D, Bjoras M, Roopenian D C, Sandlie I and Andersen J T. Dissection of the Neonatal Fc Receptor (FcRn)-Albumin Interface Using Mutagenesis and Anti-FcRn Albumin-blocking Antibodies. The Journal of biological chemistry. 2014; 289:17228-17239.

142. Levy O E, Jodka C M, Ren S S, Mamedova L, Sharma A, Samant M, D'Souza L J, Soares C J, Yuskin D R, Jin U, Parkes D G, Tatarkiewicz K and Ghosh S S. Novel exenatide analogs with peptidic albumin binding domains: potent anti-diabetic agents with extended duration of action. PloS one. 2014; 9:e87704.

143. Nilvebrant J and Hober S. The albumin-binding domain as a scaffold for protein engineering. Computational and structural biotechnology journal. 2013; 6:e201303009.

144. Baggish A L and Boucher C A. Radiopharmaceutical agents for myocardial perfusion imaging. Circulation. 2008; 118:1668-74.

145. Guo Y, Yuan H, Claudio N M, Kura S, Shakerdge N, Mempel T R, Bacskai B J and Josephson L. PEG-like nanoprobes: multimodal, pharmacokinetically and optically tunable nanomaterials. PloS one. 2014; 9:e95406.

146. Ingert C, Grima M, Michel B, Barthelmebs M and Imbs J L. [Renal tissue angiotensins during converting enzyme inhibition of angiotensin I in spontaneously hypertensive rat]. Archives des maladies du coeur et des vaisseaux. 1997; 90:1135-41.

147. Sarav M, Wang Y, Hack B K, Chang A, Jensen M, Bao L and Quigg R J. Renal FcRn reclaims albumin but facilitates elimination of IgG. J Am Soc Nephrol. 2009; 20:1941-52.

148. Spiekermann et al., Receptor-mediated immunoglobulin G transport across mucosal barriers in adult life: functional expression of FcRn in the mammalian lung. J. Exp. Med. 2002 Aug. 5; 196(3)-10.

149. Bitonti et al., Pulmonary delivery of an erythropoietin Fc fusion protein in non-human primates through an immunoglobulin transport pathway. Proc. Natl. Acad. Sci. USA 2004 Jun. 29; 101(26):9763-8.

150. Palazzo V, Provenzano A, Becherucci F, Sansavini G, Mazzinghi B, Orlandini V, Giunti L, Roperto R M, Pantaleo M, Artuso R, Andreucci E, Bargiacchi S, Traficante G, Stagi S, Murer L, Benetti E, Emma F, Giordano M, Rivieri F, Colussi G, Penco S, Manfredini E, Caruso M R, Garavelli L, Andrulli S, Vergine G, Miglietti N, Mancini E, Malaventura C, Percesepe A, Grosso E, Materassi M, Romagnani P and Giglio S. The genetic and clinical spectrum of a large cohort of patients with distal renal tubular acidosis. Kidney international. 2017.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

---

We claim:

1. A variant of angiotensin converting enzyme 2 (ACE2) comprising the amino acid sequence as set forth in SEQ ID NO: 3 or SEQ ID NO: 4; wherein the variant has ACE2 activity, and a molecular weight ranging from 60 kDa to 71 kDa, wherein the variant allows for its delivery via glomerular filtration.

2. The variant of ACE2 of claim 1, wherein the variant of ACE2 further comprises an N-terminal deletion, a C-terminal deletion, or both, relative to full-length ACE2 (SEQ ID NO:1).

3. The variant of ACE2 of claim 2, wherein the deletion removes a glycosylation site present in full-length ACE2.

4. The variant of ACE2 of claim 1, wherein the variant of ACE2 has higher ACE2 activity than full-length ACE2 (SEQ ID NO:1) for converting AngII(1-8) to Ang(1-7).

5. The variant of ACE2 of claim 1, wherein the variant of ACE2 has a half-live in plasma of at least one week.

6. A fusion protein comprising the variant of ACE2 of claim 1 fused to a heterologous amino acid sequence that increases the half-life of the variant of ACE2 in plasma.

7. The fusion protein of claim 6, wherein the fusion protein has a half-live in plasma of at least one week.

8. The fusion protein of claim 6, wherein the heterologous amino acid sequence comprises an amino acid sequence selected from the group consisting of (i) an amino acid sequence of the Fc portion of an antibody or a fragment thereof, which is devoid of its hinge region to prevent dimerization of the fusion polypeptide; (ii) an amino acid sequence of domain III of human serum albumin or a fragment thereof; and (iii) an amino acid sequence of the C-terminal albumin binding domain 3 (ABD3) of streptococcal protein G.

9. The fusion protein of claim 6 further comprising a linker amino acid sequence between the variant of ACE2 and the heterologous amino acid sequence, the linker sequence comprising 5-15 amino acids selected from glycine and serine.

10. The fusion protein of claim 6, further comprising an N-terminal or C-terminal histidine tag.

11. A conjugate comprising the variant of ACE2 of claim 1 conjugated to a polyethylene glycol polymer.

12. A conjugate comprising the variant of ACE2 of claim 1 conjugated to a nanoparticle.

13. The conjugate comprising the variant of ACE2 of claim 1 conjugated to a polyethylene glycol polymer or to a nanoparticle, wherein the conjugate has a half-live in plasma of at least one week.

14. A pharmaceutical composition comprising: (i) the variant of ACE2 of claim 1; and (ii) a suitable pharmaceutical carrier.

15. A method for reducing AngII(1-8) levels and/or increasing Ang(1-7) levels in a subject in need thereof, the method comprising administering to the subject the pharmaceutical composition of claim 14.

16. The method of claim 15, wherein the subject has a condition selected from the group consisting of diabetic kidney disease, acute renal failure, chronic kidney disease, glomerulonephritis, renal artery stenosis, idiopathic pulmonary fibrosis, liver fibrosis in liver cirrhosis patients, an aortic aneurysm, cardiac fibrosis and remodeling, left ventricular hypertrophy, and an acute stroke.

17. The method of claim 15, wherein the pharmaceutical composition is administered by intravenous administration or subcutaneous administration.

18. The method of claim 15, wherein the pharmaceutical composition is administered pulmonarily.

* * * * *